United States Patent
Kaleko et al.

(10) Patent No.: US 11,338,020 B2
(45) Date of Patent: May 24, 2022

(54) ALKALINE PHOSPHATASE AGENTS FOR TREATMENT OF NEURODEVELOPMENTAL DISORDERS

(71) Applicant: Synthetic Biologies, Inc., Rockville, MD (US)

(72) Inventors: Michael Kaleko, Rockville, MD (US); Christian Furlan Freguia, Rockville, MD (US); Sheila Connelly, Rockville, MD (US)

(73) Assignee: Synthetic Biologics, Inc., Rockville, MD (US)

( * ) Notice: Subject to any disclaimer, the term of this patent is extended or adjusted under 35 U.S.C. 154(b) by 0 days.

(21) Appl. No.: 16/960,362

(22) PCT Filed: Jan. 8, 2019

(86) PCT No.: PCT/US2019/012671
§ 371 (c)(1),
(2) Date: Jul. 7, 2020

(87) PCT Pub. No.: WO2019/139891
PCT Pub. Date: Jul. 18, 2019

(65) Prior Publication Data
US 2021/0060139 A1    Mar. 4, 2021

Related U.S. Application Data

(60) Provisional application No. 62/679,310, filed on Jun. 1, 2018, provisional application No. 62/615,227, filed on Jan. 9, 2018.

(51) Int. Cl.
| | | |
|---|---|---|
| A61K 38/45 | (2006.01) |
| A61K 38/46 | (2006.01) |
| A61P 25/00 | (2006.01) |
| A61K 9/00 | (2006.01) |

(52) U.S. Cl.
CPC .......... A61K 38/465 (2013.01); A61K 9/0053 (2013.01); A61P 25/00 (2018.01)

(58) Field of Classification Search
None
See application file for complete search history.

(56) References Cited

U.S. PATENT DOCUMENTS

| | | | |
|---|---|---|---|
| 5,773,226 A | 6/1998 | Millan |
| 5,821,095 A | 10/1998 | Hattori et al. |
| 5,891,699 A | 4/1999 | Boulain et al. |
| 5,948,410 A | 9/1999 | Van Scharrenburg et al. |
| 6,290,952 B1 | 9/2001 | Poelstra et al. |
| 6,406,899 B1 | 6/2002 | Hoelke et al. |
| 6,638,531 B1 | 10/2003 | Amerongen et al. |
| 6,649,390 B1 | 11/2003 | Sheng et al. |
| 6,686,392 B1 | 2/2004 | Avram et al. |
| 6,756,063 B2 | 6/2004 | Kiss |
| 6,793,928 B1 | 9/2004 | Van Scharrenburg et al. |
| 6,884,602 B2 | 4/2005 | Mueller et al. |
| 6,905,689 B2 | 6/2005 | Schneidinger et al. |
| 7,011,965 B2 | 3/2006 | Kiss |
| 7,014,852 B2 | 3/2006 | Kiss |
| 7,048,914 B2 | 5/2006 | Kiss |
| 7,060,677 B1 | 6/2006 | Van Berkel et al. |
| 7,312,198 B2 | 12/2007 | Kiss |
| 7,374,754 B2 | 5/2008 | Kiss |
| 7,423,029 B1 | 9/2008 | Kiss |
| 7,501,116 B2 | 3/2009 | Kiss |
| 7,557,081 B2 | 7/2009 | Kiss |
| 7,589,083 B2 | 9/2009 | Kiss |
| 7,655,620 B2 | 2/2010 | Kiss |
| 7,695,714 B2 | 4/2010 | Kiss |
| 7,718,170 B2 | 5/2010 | Kiss |
| 7,763,712 B2 | 7/2010 | Crine et al. |
| 7,781,423 B2 | 8/2010 | Kiss |
| 7,786,082 B2 | 8/2010 | Kiss |
| 7,790,685 B2 | 9/2010 | Kiss |
| 7,858,085 B2 | 12/2010 | Kiss |
| 7,943,126 B2 | 5/2011 | Tomatsu et al. |
| 7,943,606 B2 | 5/2011 | Kiss |
| 7,960,529 B2 | 6/2011 | Crine et al. |
| 7,964,188 B2 | 6/2011 | Kiss |
| 8,372,638 B2 | 2/2013 | Kiss |
| 8,460,654 B2 | 6/2013 | Kiss |
| 8,557,545 B2 | 10/2013 | Velders et al. |
| 8,574,863 B2 | 11/2013 | Brands et al. |
| 8,586,032 B2 | 11/2013 | Pickkers et al. |
| 8,603,464 B2 | 12/2013 | Kiss |

(Continued)

FOREIGN PATENT DOCUMENTS

| | | |
|---|---|---|
| EP | 1952823 A1 | 8/2008 |
| EP | 1759001 B1 | 4/2011 |

(Continued)

OTHER PUBLICATIONS

International Search Report & Written Opinion, PCT Appl. No. PCT/US19/12671, dated Apr. 15, 2019, 12 pages.
Panagos, et al., "Breastmilk from obese mothers has pro-inflammatory properties and decreased neuroprotective factors," Journal of Perinatology, 2016, pp. 1-7.
Riggle, et al., "Intestinal alkaline phosphatase prevents the systemic inflammatory response associated with necrotizing enterocolitis," Journal of Surgical Research, 180 (2013), pp. 21-26.
Alshahrani, et al., "Stability-enhanced Hot-melt Extruded Amorphous Solid Dispersions via Combinations of Soluplus® and HPMCAS-HF," American Association of Pharmaceutical Scientists, vol. 16, No. 4, pp. 824-834, Aug. 2015.

(Continued)

*Primary Examiner* — Ralph J Gitomer
(74) *Attorney, Agent, or Firm* — Morgan, Lewis & Bockius LLP

(57) ABSTRACT

Compositions and methods, including therapeutic alkaline phosphatases that find use in the treatment or prevention of various neurodevelopmental diseases or disorders, are described.

18 Claims, 18 Drawing Sheets
Specification includes a Sequence Listing.

(56) References Cited

U.S. PATENT DOCUMENTS

| | | | |
|---|---|---|---|
| 8,647,854 B2 | 2/2014 | Lee et al. | |
| 8,691,208 B2 | 4/2014 | Tomatsu et al. | |
| 8,735,087 B2 | 5/2014 | Brands et al. | |
| 8,778,674 B2 | 7/2014 | Kiss | |
| 8,784,805 B2 | 7/2014 | Brands | |
| 8,784,833 B2 | 7/2014 | Sly et al. | |
| 8,932,587 B2 | 1/2015 | Hodin et al. | |
| 9,133,446 B2 | 9/2015 | Aiba et al. | |
| 9,631,185 B2 | 4/2017 | Schyns et al. | |
| 9,926,544 B2 | 3/2018 | Raaben et al. | |
| 9,976,129 B2 | 5/2018 | Kamiya et al. | |
| 9,988,620 B2 | 6/2018 | Crine et al. | |
| 10,000,532 B2 | 6/2018 | Crine et al. | |
| 10,052,366 B2 | 8/2018 | Crine et al. | |
| 10,449,236 B2 | 10/2019 | Marozsan et al. | |
| 10,570,380 B2 | 2/2020 | Jonk et al. | |
| 10,603,361 B2 | 3/2020 | Odrljin | |
| 10,987,410 B2 * | 4/2021 | Wacher | A61K 47/38 |
| 2004/0091530 A1 | 5/2004 | Ende et al. | |
| 2007/0280922 A1 | 12/2007 | Kiss | |
| 2010/0221234 A1 | 9/2010 | Crine et al. | |
| 2010/0297119 A1 | 11/2010 | Crine et al. | |
| 2011/0206654 A1 | 8/2011 | Hodin et al. | |
| 2012/0308526 A1 | 12/2012 | Ohtake et al. | |
| 2013/0045192 A1 | 2/2013 | Movalia et al. | |
| 2013/0108635 A1 | 5/2013 | Crine et al. | |
| 2013/0280232 A1 | 10/2013 | Brands et al. | |
| 2013/0323244 A1 | 12/2013 | Crine et al. | |
| 2015/0216813 A1 | 8/2015 | Everett et al. | |
| 2016/0201110 A1* | 7/2016 | Malo | A61K 35/741 424/48 |
| 2017/0252327 A1 | 9/2017 | Hodin et al. | |
| 2021/0030686 A1* | 2/2021 | Bristol | A61K 9/2027 |
| 2021/0189358 A1* | 6/2021 | Rodrigues | C12N 5/0682 |

FOREIGN PATENT DOCUMENTS

| | | |
|---|---|---|
| EP | 2158319 B1 | 7/2011 |
| EP | 2368999 B1 | 3/2014 |
| EP | 2662448 B1 | 12/2016 |
| JP | 2017/192381 A * | 10/2017 |
| WO | WO 1999/026654 A1 | 6/1999 |
| WO | WO 1999/033955 A1 | 7/1999 |
| WO | WO 1999/037678 A2 | 7/1999 |
| WO | WO 2000/032629 A2 | 6/2000 |
| WO | WO 2001/034641 A2 | 5/2001 |
| WO | WO 2001/056627 A1 | 8/2001 |
| WO | WO 2002/060503 A1 | 8/2002 |
| WO | WO 2004/112494 A2 | 12/2004 |
| WO | WO 2005/055956 A2 | 6/2005 |
| WO | WO 2005/074978 A1 | 8/2005 |
| WO | WO 2005/103263 A1 | 11/2005 |
| WO | WO 2007/055760 A2 | 5/2007 |
| WO | WO 2007/081654 A2 | 7/2007 |
| WO | WO 2008/024103 A1 | 2/2008 |
| WO | WO 2008/094037 A1 | 8/2008 |
| WO | WO 2008/104199 A1 | 9/2008 |
| WO | WO 2008/104200 A1 | 9/2008 |
| WO | WO 2008/133511 A2 | 11/2008 |
| WO | WO 2008/138131 A1 | 11/2008 |
| WO | WO 2009/028943 A1 | 3/2009 |
| WO | WO 2009/106368 A1 | 9/2009 |
| WO | WO 2010/025267 A2 | 3/2010 |
| WO | WO 2010/151526 A1 | 12/2010 |
| WO | WO 2011/057250 A1 | 5/2011 |
| WO | WO 2011/134084 A1 | 11/2011 |
| WO | WO 2012/054057 A1 | 4/2012 |
| WO | WO 2012/169892 A2 | 12/2012 |
| WO | WO 2012/177100 A2 | 12/2012 |
| WO | WO 2013/058833 A1 | 4/2013 |
| WO | WO 2013/059491 A1 | 4/2013 |
| WO | WO 2014/007229 A1 | 1/2014 |
| WO | WO 2015/112015 A1 | 7/2015 |
| WO | WO 2015/112017 A1 | 7/2015 |
| WO | WO 2015/166045 A2 | 11/2015 |
| WO | WO 2016/090251 A1 | 6/2016 |
| WO | WO 2016/123342 A2 | 8/2016 |
| WO | WO 2017/031114 A1 | 2/2017 |
| WO | WO 2017/058822 A1 | 4/2017 |
| WO | WO 2017/074466 A1 | 5/2017 |
| WO | WO 2017/155569 A1 | 9/2017 |
| WO | WO 2017/173395 A1 | 10/2017 |
| WO | WO 2017/173413 A1 | 10/2017 |
| WO | WO 2017/214130 A1 | 12/2017 |
| WO | WO 2018/009555 A1 | 1/2018 |
| WO | WO 2018/035420 A1 | 2/2018 |
| WO | WO 2018/127363 A1 | 7/2018 |
| WO | WO 2018/164995 A1 | 9/2018 |
| WO | WO 2018/175413 A1 | 9/2018 |
| WO | WO 2018/183720 A1 | 10/2018 |
| WO | WO 2017/203426 A1 | 2/2019 |
| WO | WO 2018/183720 A9 | 7/2019 |
| WO | WO 2019/139891 A1 | 7/2019 |
| WO | WO 2019/172766 A1 | 9/2019 |
| WO | WO 2019/183208 A1 | 9/2019 |
| WO | WO 2019/183209 A1 | 9/2019 |
| WO | WO 2019/190752 A1 | 10/2019 |
| WO | WO 2019/245938 A1 | 12/2019 |
| WO | WO 2020/033867 A2 | 2/2020 |

OTHER PUBLICATIONS

Beumer, et al., "Calf Intestinal Alkaline Phosphatase, A Novel Therapeutic Drug for Lipopolysaccharide (LPS)-Mediated Diseases, Attenuates LPS Toxicity in Mice and Piglets," The Journal of Pharmacology and Experimental Therapeutics, vol. 307, No. 2, pp. 737-744 (Jul. 2003).

Buffington, et al., "Microbial Reconstitution Reverses Maternal Diet-Induced Social and Synaptic Deficits in Offspring," Cell, vol. 165, pp. 1762-1775, Jun. 16, 2016.

Chen, et al., "A Role for Intestinal Alkaline Phosphatase in the Maintenance of Local Gut Community," Dig Dis Sci. Apr. 2011; 56(4): 1020-1027 (doi:10.1007/s10620-010-1396-x).

Chen, et al. "Identification of specific targets for the gut mucosal defense factor intestinal alkaline phosphatase," American Journal of Physiology, Aug. 2010, Epub May 2012, vol. 299, No. 2 pp. G467-75.

Cui, et al., "Faecal microbiota transplantation protects against radiation-induced toxicity", EMBO Molecular Medicine vol. 9 | No. 4 | 2017, 14 pages.

Curatolo, et al., "Utility of Hydroxypropylmethylcellulose Acetate Succinate (HPMCAS) for Initiation and Maintenance of Drug Supersaturation in the GI Milieu," Pharmaceutical Research, vol. 26, No. 6, pp. 1419-1431 (Jun. 2009).

Economopoulos, et al., "Prevention of antibiotic-associated metabolic syndrome in mice by intestinal alkaline phosphatase," Diabetes, Obesity and Metabolism, vol. 18, No. 5., pp. 519-527 (May 2016).

Estaki, et al., "Interplay between intestinal alkaline phosphatase, diet, gut microbes and immunity," World Journal of Gastroenterology, 20(42), pp. 15650-15656 (Nov. 2014).

Estes, et al., "Maternal Immune activation: Implications for neuropsychiatric disorders," Science, vol. 356, No. 6301, pp. 772-777, Aug. 19, 2016.

Friesen, et al., "Hydroxypropyl Methylcellulose Acetate Succinate-Based Spray-Dried Dispersions: An Overview," Molecular Pharmaceuticals, vol. 5, No. 6, pp. 1003-1019 (Dec. 2008).

Goldberg, et al., "Intestinal alkaline phosphatase is a gut mucosal defense factor maintained by enteral nutrition," PNAS, vol. 105, No. 9, pp. 3551-3556 (Mar. 2008).

Hauer-Jensen, et al., "Radiation Enteropathy—Pathogenesis, Treatment, and Prevention", Nat Rev Gastroenterol Hepatol. Aug. 2014; 11(8): 470-479. doi:10.1038/nrgastro.2014.46, 27 pages.

International Search Report & Written Opinion, PCT/US2018/023327, dated May 25, 2018, 12 pages.

Kaliannan, et al., "Intestinal alkaline phosphatase prevents metabolic syndrome in mice," PNAS, vol. 110, No. 17, pp. 7003-7008 (Apr. 2013).

(56) References Cited

OTHER PUBLICATIONS

Lallès, "Intestinal alkaline phosphatase: novel functions and protective effects," Nutrition Reviews, vol. 72(2), pp. 82-94 (2014).
Liu, et al., "Intestinal Alkaline Phosphatase Regulates Tight Junction Protein Levels", J Am Coll Surg. Jun. 2016: 222(6): 1009-1017. doi: 10.1016/j.jamcollsurg.2015.12.006.
Malo, et al., "Intestinal alkaline phosphatase preserves the normal homeostasis of gut microbiota," Gut 2010;59:1476-1484 (doi:10.1136/gut.2010.211706).
Parlato, et al., "Human ALPI deficiency causes inflammatory bowel disease and highlights a key mechanism of gut homeostasis," EMBO Molecular Medicine, e8483, pp. 1-12 (Mar. 2018).
Peters, et al., "The Potential of Alkaline Phosphatase as a Treatment for Sepsis-Associated Acute Kidney Injury," Nephron Clin Pract 2014; 127: pp. 144-148 (Sep. 2014).
Ramasamy, et al., "Intestinal Alkaline Phosphatase Has Beneficial Effects in Mouse Models of Chronic Colitis", Inflamm Bowel Dis. Feb. 2011; 17(2): 532-542. doi:10.1002/ibd.21377.
Rentea, et al., "Radiation-induced changes in intestinal and tissue-nonspecific alkaline phosphatase: implications for recovery after radiation therapy", The American Journal of Surgery (2016) 212, 602-608, 7 pages.
Rieder, et al., "Animal models of intestinal fibrosis: new tools for the understanding of pathogenesis and therapy of human disease", Am J Physiol Gastrointest Liver Physiol 303: G786-G801, 2012, 16 pages.
Shah, et al., "Improved Human Bioavailability of Vemurafenib, a Practically Insoluble Drug, Using an Amorphous Polymer-Stabilized Solid Dispersion Prepared by a Solvent-Controlled Coprecipitation Process," Journal of Pharmaceutical Sciences, vol. 102, No. 3, pp. 967-981 (Mar. 2013).

\* cited by examiner

SEQUENCE LISTING

```
<160> NUMBER OF SEQ ID NOS: 18

<210> SEQ ID NO 1
<211> LENGTH: 528
<212> TYPE: PRT
<213> ORGANISM: Artificial Sequence
<220> FEATURE:
<223> OTHER INFORMATION: Synthetic polymer

<400> SEQUENCE: 1

Met Gln Gly Pro Trp Val Leu Leu Leu Gly Leu Arg Leu Gln Leu
1               5                   10                  15

Ser Leu Gly Val Ile Pro Ala Glu Glu Glu Asn Pro Ala Phe Trp Asn
                20                  25                  30

Arg Gln Ala Ala Glu Ala Leu Asp Ala Ala Lys Lys Leu Gln Pro Ile
            35                  40                  45

Gln Lys Val Ala Lys Asn Leu Ile Leu Phe Leu Gly Asp Gly Leu Gly
        50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
                100                 105                 110

Ala Thr Ala Thr Ala Tyr Leu Cys Gly Val Lys Ala Asn Phe Gln Thr
            115                 120                 125

Ile Gly Leu Ser Ala Ala Ala Arg Phe Asn Gln Cys Asn Thr Thr Arg
        130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
                180                 185                 190

Met Pro Ala Ser Ala Arg Gln Glu Gly Cys Gln Asp Ile Ala Thr Gln
            195                 200                 205

Leu Ile Ser Asn Met Asp Ile Asp Val Ile Leu Gly Gly Gly Arg Lys
        210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
```

```
                        245                 250                 255
Leu Ala Lys His Gln Gly Ala Trp Tyr Val Trp Asn Arg Thr Glu Leu
            260                 265                 270

Met Gln Ala Ser Leu Asp Gln Ser Val Thr His Leu Met Gly Leu Phe
        275                 280                 285

Glu Pro Gly Asp Thr Lys Tyr Glu Ile His Arg Asp Pro Thr Leu Asp
290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Leu Thr Glu Ala Val Met
            340                 345                 350

Phe Asp Asp Ala Ile Glu Arg Ala Gly Gln Leu Thr Ser Glu Glu Asp
        355                 360                 365

Thr Leu Thr Leu Val Thr Ala Asp His Ser His Val Phe Ser Phe Gly
    370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
            420                 425                 430

Ser Gly Ser Pro Asp Tyr Gln Gln Gln Ala Ala Val Pro Leu Ser Ser
        435                 440                 445

Glu Thr His Gly Gly Glu Asp Val Ala Val Phe Ala Arg Gly Pro Gln
    450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Cys Thr Thr Asp Ala Ala His Pro Val Ala Ala Ser Leu
            500                 505                 510

Pro Leu Leu Ala Gly Thr Leu Leu Leu Gly Ala Ser Ala Ala Pro
        515                 520                 525

<210> SEQ ID NO 2
<211> LENGTH: 533
<212> TYPE: PRT
<213> ORGANISM: Artificial Sequence
<220> FEATURE:
<223> OTHER INFORMATION: Synthetic polymer

<400> SEQUENCE: 2

Met Gln Gly Ala Cys Val Leu Leu Leu Gly Leu His Leu Gln Leu
1               5                   10                  15

Ser Leu Gly Leu Ile Pro Ala Glu Glu Asn Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
```

```
                         85                  90                  95
Ala Leu Ser Lys Thr Tyr Asn Val Asp Arg Gln Val Pro Asp Ser Ala
                100                 105                 110

Gly Thr Ala Thr Ala Tyr Leu Cys Gly Val Lys Gly Asn Tyr Arg Thr
                115                 120                 125

Ile Gly Val Ser Ala Ala Arg Tyr Asn Gln Cys Asn Thr Thr Arg
                130                 135                 140

Gly Asn Glu Val Thr Ser Val Ile Asn Arg Ala Lys Lys Ala Gly Lys
145                 150                 155                 160

Ala Val Gly Val Val Thr Thr Arg Val Gln His Ala Ser Pro Ala
                    165                 170                 175

Gly Ala Tyr Ala His Thr Val Asn Arg Asn Trp Tyr Ser Asp Ala Asp
                180                 185                 190

Leu Pro Ala Asp Ala Gln Lys Asn Gly Cys Gln Asp Ile Ala Ala Gln
                195                 200                 205

Leu Val Tyr Asn Met Asp Ile Asp Val Ile Leu Gly Gly Arg Met
                210                 215                 220

Tyr Met Phe Pro Glu Gly Thr Pro Asp Pro Glu Tyr Pro Asp Asp Ala
225                 230                 235                 240

Ser Val Asn Gly Val Arg Lys Asp Lys Gln Asn Leu Val Gln Glu Trp
                    245                 250                 255

Gln Ala Lys His Gln Gly Ala Gln Tyr Val Trp Asn Arg Thr Ala Leu
                260                 265                 270

Leu Gln Ala Ala Asp Asp Ser Ser Val Thr His Leu Met Gly Leu Phe
                275                 280                 285

Glu Pro Ala Asp Met Lys Tyr Asn Val Gln Gln Asp His Thr Lys Asp
                290                 295                 300

Pro Thr Leu Ala Glu Met Thr Glu Ala Ala Leu Gln Val Leu Ser Arg
305                 310                 315                 320

Asn Pro Arg Gly Phe Tyr Leu Phe Val Glu Gly Gly Arg Ile Asp His
                    325                 330                 335

Gly His His Asp Gly Lys Ala Tyr Met Ala Leu Thr Glu Ala Ile Met
                340                 345                 350

Phe Asp Asn Ala Ile Ala Lys Ala Asn Glu Leu Thr Ser Glu Leu Asp
                355                 360                 365

Thr Leu Ile Leu Val Thr Ala Asp His Ser His Val Phe Ser Phe Gly
                370                 375                 380

Gly Tyr Thr Leu Arg Gly Thr Ser Ile Phe Gly Leu Ala Pro Gly Lys
385                 390                 395                 400

Ala Leu Asp Ser Lys Ser Tyr Thr Ser Ile Leu Tyr Gly Asn Gly Pro
                    405                 410                 415

Gly Tyr Ala Leu Gly Gly Gly Ser Arg Pro Asp Val Asn Gly Ser Thr
                420                 425                 430

Ser Glu Glu Pro Ser Tyr Arg Gln Gln Ala Ala Val Pro Leu Ala Ser
                435                 440                 445

Glu Thr His Gly Gly Glu Asp Val Ala Val Phe Ala Arg Gly Pro Gln
                450                 455                 460

Ala His Leu Val His Gly Val Gln Glu Glu Thr Phe Val Ala His Ile
465                 470                 475                 480

Met Ala Phe Ala Gly Cys Val Glu Pro Tyr Thr Asp Cys Asn Leu Pro
                    485                 490                 495

Ala Pro Ala Thr Ala Thr Ser Ile Pro Asp Ala Ala His Leu Ala Ala
                500                 505                 510
```

```
Ser Pro Pro Pro Leu Ala Leu Leu Ala Gly Ala Met Leu Leu Leu
        515                 520                 525

Ala Pro Thr Leu Tyr
        530

<210> SEQ ID NO 3
<211> LENGTH: 530
<212> TYPE: PRT
<213> ORGANISM: Artificial Sequence
<220> FEATURE:
<223> OTHER INFORMATION: Synthetic polymer

<400> SEQUENCE: 3

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Arg Tyr Asn Gln Cys Asn Thr Thr Ser
    130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
    210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
    290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335
```

```
Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
            355                 360                 365

Thr Leu Ile Leu Ala Thr Ala Asp His Ser His Val Phe Ser Phe Gly
        370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Leu Arg Pro Val Asn Asp Ser Ile
            420                 425                 430

Ser Glu Asp Pro Ser Tyr Arg Gln Gln Ala Ala Val Pro Leu Ser Ser
            435                 440                 445

Glu Ser His Gly Gly Glu Asp Val Ala Val Phe Ala Arg Gly Pro Gln
450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
                485                 490                 495

Ala Pro Ser Gly Leu Ser Asp Ala Ala His Leu Ala Ala Ser Pro Pro
            500                 505                 510

Ser Leu Ala Leu Leu Ala Gly Ala Met Leu Leu Leu Leu Ala Pro Ala
        515                 520                 525

Leu Tyr
    530

<210> SEQ ID NO 4
<211> LENGTH: 503
<212> TYPE: PRT
<213> ORGANISM: Artificial Sequence
<220> FEATURE:
<223> OTHER INFORMATION: Synthetic polymer

<400> SEQUENCE: 4

Met Gln Gly Pro Trp Val Leu Leu Leu Gly Leu Arg Leu Gln Leu
1               5                   10                  15

Ser Leu Gly Val Ile Pro Ala Glu Glu Asn Pro Ala Phe Trp Asn
            20                  25                  30

Arg Gln Ala Ala Glu Ala Leu Asp Ala Ala Lys Lys Leu Gln Pro Ile
        35                  40                  45

Gln Lys Val Ala Lys Asn Leu Ile Leu Phe Leu Gly Asp Gly Leu Gly
    50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
            100                 105                 110

Ala Thr Ala Thr Ala Tyr Leu Cys Gly Val Lys Ala Asn Phe Gln Thr
        115                 120                 125

Ile Gly Leu Ser Ala Ala Ala Arg Phe Asn Gln Cys Asn Thr Thr Arg
    130                 135                 140

Gly Asn Glu Val Ile Ser Val Met Asn Arg Ala Lys Gln Ala Gly Lys
145                 150                 155                 160
```

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
            180                 185                 190

Met Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Arg Lys
    210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
            260                 265                 270

Met Gln Ala Ser Leu Asp Gln Ser Val Thr His Leu Met Gly Leu Phe
        275                 280                 285

Glu Pro Gly Asp Thr Lys Tyr Glu Ile His Arg Asp Pro Thr Leu Asp
    290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Leu Thr Glu Ala Val Met
            340                 345                 350

Phe Asp Asp Ala Ile Glu Arg Ala Gly Gln Leu Thr Ser Glu Glu Asp
        355                 360                 365

Thr Leu Thr Leu Val Thr Ala Asp His Ser His Val Phe Ser Phe Gly
    370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
            420                 425                 430

Ser Gly Ser Pro Asp Tyr Gln Gln Gln Ala Ala Val Pro Leu Ser Ser
        435                 440                 445

Glu Thr His Gly Gly Glu Asp Val Ala Val Phe Ala Arg Gly Pro Gln
    450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Gly Thr Thr Asp
            500

<210> SEQ ID NO 5
<211> LENGTH: 506
<212> TYPE: PRT
<213> ORGANISM: Artificial Sequence
<220> FEATURE:
<223> OTHER INFORMATION: Synthetic polymer

<400> SEQUENCE: 5

Met Gln Gly Ala Cys Val Leu Leu Leu Leu Gly Leu His Leu Gln Leu
1               5                   10                  15

-continued

Ser Leu Gly Leu Ile Pro Ala Glu Glu Asn Pro Ala Phe Trp Asn
        20              25              30

Arg Gln Ala Ala Gln Ala Leu Asp Val Ala Lys Lys Leu Gln Pro Ile
            35              40              45

Gln Thr Ala Ala Lys Asn Val Ile Leu Phe Leu Gly Asp Gly Met Gly
50              55              60

Val Pro Thr Val Thr Ala Thr Arg Ile Leu Lys Gly Gln Met Asn Gly
65              70              75              80

Lys Leu Gly Pro Glu Thr Pro Leu Ala Met Asp Gln Phe Pro Tyr Val
                85              90              95

Ala Leu Ser Lys Thr Tyr Asn Val Asp Arg Gln Val Pro Asp Ser Ala
            100             105             110

Gly Thr Ala Thr Ala Tyr Leu Cys Gly Val Lys Gly Asn Tyr Arg Thr
        115             120             125

Ile Gly Val Ser Ala Ala Ala Arg Tyr Asn Gln Cys Asn Thr Thr Arg
    130             135             140

Gly Asn Glu Val Thr Ser Val Ile Asn Arg Ala Lys Lys Ala Gly Lys
145             150             155             160

Ala Val Gly Val Val Thr Thr Thr Arg Val Gln His Ala Ser Pro Ala
                165             170             175

Gly Ala Tyr Ala His Thr Val Asn Arg Asn Trp Tyr Ser Asp Ala Asp
            180             185             190

Leu Pro Ala Asp Ala Gln Lys Asn Gly Cys Gln Asp Ile Ala Ala Gln
        195             200             205

Leu Val Tyr Asn Met Asp Ile Asp Val Ile Leu Gly Gly Gly Arg Met
    210             215             220

Tyr Met Phe Pro Glu Gly Thr Pro Asp Pro Glu Tyr Pro Asp Asp Ala
225             230             235             240

Ser Val Asn Gly Val Arg Lys Asp Lys Gln Asn Leu Val Gln Glu Trp
                245             250             255

Gln Ala Lys His Gln Gly Ala Gln Tyr Val Trp Asn Arg Thr Ala Leu
            260             265             270

Leu Gln Ala Ala Asp Asp Ser Ser Val Thr His Leu Met Gly Leu Phe
        275             280             285

Glu Pro Ala Asp Met Lys Tyr Asn Val Gln Gln Asp His Thr Lys Asp
    290             295             300

Pro Thr Leu Ala Glu Met Thr Glu Ala Ala Leu Gln Val Leu Ser Arg
305             310             315             320

Asn Pro Arg Gly Phe Tyr Leu Phe Val Glu Gly Gly Arg Ile Asp His
                325             330             335

Gly His His Asp Gly Lys Ala Tyr Met Ala Leu Thr Glu Ala Ile Met
            340             345             350

Phe Asp Asn Ala Ile Ala Lys Ala Asn Glu Leu Thr Ser Glu Leu Asp
        355             360             365

Thr Leu Ile Leu Val Thr Ala Asp His Ser His Val Phe Ser Phe Gly
    370             375             380

Gly Tyr Thr Leu Arg Gly Thr Ser Ile Phe Gly Leu Ala Pro Gly Lys
385             390             395             400

Ala Leu Asp Ser Lys Ser Tyr Thr Ser Ile Leu Tyr Gly Asn Gly Pro
                405             410             415

Gly Tyr Ala Leu Gly Gly Gly Ser Arg Pro Asp Val Asn Gly Ser Thr
            420             425             430

```
Ser Glu Glu Pro Ser Tyr Arg Gln Gln Ala Ala Val Pro Leu Ala Ser
            435                 440                 445

Glu Thr His Gly Gly Glu Asp Val Ala Val Phe Ala Arg Gly Pro Gln
450                 455                 460

Ala His Leu Val His Gly Val Gln Glu Thr Phe Val Ala His Ile
465                 470                 475                 480

Met Ala Phe Ala Gly Cys Val Glu Pro Tyr Thr Asp Cys Asn Leu Pro
                485                 490                 495

Ala Pro Ala Thr Ala Thr Ser Ile Pro Asp
                500                 505

<210> SEQ ID NO 6
<211> LENGTH: 503
<212> TYPE: PRT
<213> ORGANISM: Artificial Sequence
<220> FEATURE:
<223> OTHER INFORMATION: Synthetic polymer

<400> SEQUENCE: 6

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Arg Tyr Asn Gln Cys Asn Thr Thr Ser
    130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
    210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285
```

-continued

Glu Pro Ala Asp Met Lys Tyr Asn Val Gln Gln Asp Pro Thr Lys Asp
        290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
            355                 360                 365

Thr Leu Ile Leu Ala Thr Ala Asp His Ser His Val Phe Ser Phe Gly
370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Gly Leu Arg Pro Asp Val Asn Asp Ser Ile
                420                 425                 430

Ser Glu Asp Pro Ser Tyr Arg Gln Gln Ala Ala Val Pro Leu Ser Ser
            435                 440                 445

Glu Ser His Gly Gly Glu Asp Val Ala Val Phe Ala Arg Gly Pro Gln
450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
                485                 490                 495

Ala Pro Ser Gly Leu Ser Asp
            500

<210> SEQ ID NO 7
<211> LENGTH: 508
<212> TYPE: PRT
<213> ORGANISM: Artificial Sequence
<220> FEATURE:
<223> OTHER INFORMATION: Synthetic polymer

<400> SEQUENCE: 7

Met Gln Trp Ala Cys Val Leu Leu Leu Gly Leu Trp Leu Gln Leu
1               5                   10                  15

Ser Leu Thr Phe Ile Pro Ala Glu Glu Asp Pro Ala Phe Trp Asn
                20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
        50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
                100                 105                 110

Gly Thr Ala Thr Ala Tyr Leu Cys Gly Val Lys Gly Asn Tyr Lys Thr
            115                 120                 125

Ile Gly Val Ser Ala Ala Ala Arg Tyr Asn Gln Cys Asn Thr Thr Ser
        130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
            165                 170                 175

Gly Ala Tyr Ala His Thr Val Asn Arg Asn Trp Tyr Ser Asp Ala Asp
        180                 185                 190

Leu Pro Ala Asp Ala Gln Thr Tyr Gly Cys Gln Asp Ile Ala Thr Gln
    195                 200                 205

Leu Val Asn Asn Met Asp Ile Asp Val Ile Leu Gly Gly Arg Met
210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
            245                 250                 255

Gln Ala Lys His Gln Gly Ala Gln Tyr Val Trp Asn Arg Thr Glu Leu
        260                 265                 270

Leu Gln Ala Ala Asn Asp Pro Ser Val Thr His Leu Met Gly Leu Phe
    275                 280                 285

Glu Pro Ala Asp Met Lys Tyr Asn Val Gln Gln Asp Pro Thr Lys Asp
290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
            325                 330                 335

Gly His His Glu Gly Lys Ala Tyr Met Ala Leu Thr Asp Thr Val Met
        340                 345                 350

Phe Asp Asn Ala Ile Ala Lys Ala Asn Glu Leu Thr Ser Glu Leu Asp
    355                 360                 365

Thr Leu Ile Leu Ala Thr Ala Asp His Ser His Val Phe Ser Phe Gly
370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
            405                 410                 415

Gly Tyr Val Leu Gly Gly Gly Leu Arg Pro Asp Val Asn Asp Ser Ile
        420                 425                 430

Ser Glu Asp Pro Ser Tyr Arg Gln Gln Ala Ala Val Pro Leu Ser Ser
    435                 440                 445

Glu Ser His Gly Gly Glu Asp Val Ala Val Phe Ala Arg Gly Pro Gln
450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
            485                 490                 495

Ala Pro Ser Gly Leu Ser Asp Ala Ala His Leu Ala
        500                 505

<210> SEQ ID NO 8
<211> LENGTH: 754
<212> TYPE: PRT
<213> ORGANISM: Artificial Sequence
<220> FEATURE:
<223> OTHER INFORMATION: Synthetic polymer

<400> SEQUENCE: 8

-continued

```
Met Gln Gly Ala Cys Val Leu Leu Leu Gly Leu His Leu Gln Leu
  1               5                  10                  15

Ser Leu Gly Leu Ile Pro Ala Glu Glu Asn Pro Ala Phe Trp Asn
             20                  25                  30

Arg Gln Ala Ala Gln Ala Leu Asp Val Ala Lys Lys Leu Gln Pro Ile
             35                  40                  45

Gln Thr Ala Ala Lys Asn Val Ile Leu Phe Leu Gly Asp Gly Met Gly
     50                  55                  60

Val Pro Thr Val Thr Ala Thr Arg Ile Leu Lys Gly Gln Met Asn Gly
 65                  70                  75                  80

Lys Leu Gly Pro Glu Thr Pro Leu Ala Met Asp Gln Phe Pro Tyr Val
                 85                  90                  95

Ala Leu Ser Lys Thr Tyr Asn Val Asp Arg Gln Val Pro Asp Ser Ala
             100                 105                 110

Gly Thr Ala Thr Ala Tyr Leu Cys Gly Val Lys Gly Asn Tyr Arg Thr
             115                 120                 125

Ile Gly Val Ser Ala Ala Arg Tyr Asn Gln Cys Asn Thr Thr Arg
130                 135                 140

Gly Asn Glu Val Thr Ser Val Ile Asn Arg Ala Lys Lys Ala Gly Lys
145                 150                 155                 160

Ala Val Gly Val Val Thr Thr Thr Arg Val Gln His Ala Ser Pro Ala
                 165                 170                 175

Gly Ala Tyr Ala His Thr Val Asn Arg Asn Trp Tyr Ser Asp Ala Asp
             180                 185                 190

Leu Pro Ala Asp Ala Gln Lys Asn Gly Cys Gln Asp Ile Ala Ala Gln
             195                 200                 205

Leu Val Tyr Asn Met Asp Ile Asp Val Ile Leu Gly Gly Gly Arg Met
210                 215                 220

Tyr Met Phe Pro Glu Gly Thr Pro Asp Pro Glu Tyr Pro Asp Asp Ala
225                 230                 235                 240

Ser Val Asn Gly Val Arg Lys Asp Lys Gln Asn Leu Val Gln Glu Trp
                 245                 250                 255

Gln Ala Lys His Gln Gly Ala Gln Tyr Val Trp Asn Arg Thr Ala Leu
             260                 265                 270

Leu Gln Ala Ala Asp Asp Ser Ser Val Thr His Leu Met Gly Leu Phe
         275                 280                 285

Glu Pro Ala Asp Met Lys Tyr Asn Val Gln Gln Asp His Thr Lys Asp
         290                 295                 300

Pro Thr Leu Ala Glu Met Thr Glu Ala Ala Leu Gln Val Leu Ser Arg
305                 310                 315                 320

Asn Pro Arg Gly Phe Tyr Leu Phe Val Glu Gly Gly Arg Ile Asp His
                 325                 330                 335

Gly His His Asp Gly Lys Ala Tyr Met Ala Leu Thr Glu Ala Ile Met
             340                 345                 350

Phe Asp Asn Ala Ile Ala Lys Ala Asn Glu Leu Thr Ser Glu Leu Asp
         355                 360                 365

Thr Leu Ile Leu Val Thr Ala Asp His Ser His Val Phe Ser Phe Gly
     370                 375                 380

Gly Tyr Thr Leu Arg Gly Thr Ser Ile Phe Gly Leu Ala Pro Gly Lys
385                 390                 395                 400

Ala Leu Asp Ser Lys Ser Tyr Thr Ser Ile Leu Tyr Gly Asn Gly Pro
             405                 410                 415

Gly Tyr Ala Leu Gly Gly Gly Ser Arg Pro Asp Val Asn Gly Ser Thr
```

```
            420                 425                 430
Ser Glu Glu Pro Ser Tyr Arg Gln Gln Ala Ala Val Pro Leu Ala Ser
            435                 440                 445

Glu Thr His Gly Gly Glu Asp Val Ala Val Phe Ala Arg Gly Pro Gln
        450                 455                 460

Ala His Leu Val His Gly Val Gln Glu Thr Phe Val Ala His Ile
465                 470                 475                 480

Met Ala Phe Ala Gly Cys Val Glu Pro Tyr Thr Asp Cys Asn Leu Pro
                485                 490                 495

Ala Pro Ala Thr Ala Thr Ser Ile Pro Asp Gly Gly Ser Gly Gly Ser
            500                 505                 510

Gly Gly Gly Gly Ser Gly Gly Gly Ser Glu Pro Lys Ser Cys Asp
        515                 520                 525

Lys Thr His Thr Cys Pro Pro Cys Pro Ala Pro Glu Leu Leu Gly Gly
        530                 535                 540

Pro Ser Val Phe Leu Phe Pro Pro Lys Pro Lys Asp Thr Leu Met Ile
545                 550                 555                 560

Ser Arg Thr Pro Glu Val Thr Cys Val Val Val Asp Val Ser His Glu
                565                 570                 575

Asp Pro Gln Val Lys Phe Asn Trp Tyr Val Asp Gly Val Gln Val His
                580                 585                 590

Asn Ala Lys Thr Lys Pro Arg Glu Gln Gln Tyr Asn Ser Thr Tyr Arg
            595                 600                 605

Val Val Ser Val Leu Thr Val Leu His Gln Asn Trp Leu Asp Gly Lys
            610                 615                 620

Glu Tyr Lys Cys Lys Val Ser Asn Lys Ala Leu Pro Ala Pro Ile Glu
625                 630                 635                 640

Lys Thr Ile Ser Lys Ala Lys Gly Gln Pro Arg Glu Pro Gln Val Tyr
                645                 650                 655

Thr Leu Pro Pro Ser Arg Glu Glu Met Thr Lys Asn Gln Val Ser Leu
                660                 665                 670

Thr Cys Leu Val Lys Gly Phe Tyr Pro Ser Asp Ile Ala Val Glu Trp
            675                 680                 685

Glu Ser Asn Gly Gln Pro Glu Asn Asn Tyr Lys Thr Thr Pro Pro Val
            690                 695                 700

Leu Asp Ser Asp Gly Ser Phe Phe Leu Tyr Ser Lys Leu Thr Val Asp
705                 710                 715                 720

Lys Ser Arg Trp Gln Gln Gly Asn Val Phe Ser Cys Ser Val Met His
                725                 730                 735

Glu Ala Leu His Asn His Tyr Thr Gln Lys Ser Leu Ser Leu Ser Pro
            740                 745                 750

Gly Lys

<210> SEQ ID NO 9
<211> LENGTH: 751
<212> TYPE: PRT
<213> ORGANISM: Artificial Sequence
<220> FEATURE:
<223> OTHER INFORMATION: Synthetic polymer

<400> SEQUENCE: 9

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
                20                  25                  30
```

-continued

Arg Gln Ala Ala Gln Ala Leu Asp Val Ala Lys Lys Leu Gln Pro Ile
     35                  40                  45

Gln Thr Ala Ala Lys Asn Val Ile Leu Phe Leu Gly Asp Gly Met Gly
 50                  55                  60

Val Pro Thr Val Thr Ala Thr Arg Ile Leu Lys Gly Gln Met Asn Gly
 65                  70                  75                  80

Lys Leu Gly Pro Glu Thr Pro Leu Ala Met Asp Gln Phe Pro Tyr Val
                 85                  90                  95

Ala Leu Ser Lys Thr Tyr Asn Val Asp Arg Gln Val Pro Asp Ser Ala
             100                 105                 110

Gly Thr Ala Thr Ala Tyr Leu Cys Gly Val Lys Gly Asn Tyr Lys Thr
             115                 120                 125

Ile Gly Val Ser Ala Ala Ala Arg Tyr Asn Gln Cys Asn Thr Thr Ser
130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
             180                 185                 190

Leu Pro Ala Asp Ala Gln Thr Tyr Gly Cys Gln Asp Ile Ala Thr Gln
             195                 200                 205

Leu Val Asn Asn Met Asp Ile Asp Val Ile Leu Gly Gly Gly Arg Met
210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
             260                 265                 270

Leu Gln Ala Ala Asn Asp Pro Ser Val Thr His Leu Met Gly Leu Phe
             275                 280                 285

Glu Pro Ala Asp Met Lys Tyr Asn Val Gln Gln Asp Pro Thr Lys Asp
290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335

Gly His His Glu Gly Lys Ala Tyr Met Ala Leu Thr Asp Thr Val Met
             340                 345                 350

Phe Asp Asn Ala Ile Ala Lys Ala Asn Glu Leu Thr Ser Glu Leu Asp
             355                 360                 365

Thr Leu Ile Leu Ala Thr Ala Asp His Ser His Val Phe Ser Phe Gly
370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Gly Leu Arg Pro Asp Val Asn Asp Ser Ile
             420                 425                 430

Ser Glu Asp Pro Ser Tyr Arg Gln Gln Ala Ala Val Pro Leu Ser Ser
             435                 440                 445

Glu Ser His Gly Gly Glu Asp Val Ala Val Phe Ala Arg Gly Pro Gln
450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
                485                 490                 495

Ala Pro Ser Gly Leu Ser Asp Gly Ser Gly Ser Gly Gly Gly
        500                 505                 510

Gly Ser Gly Gly Gly Ser Glu Pro Lys Ser Cys Asp Lys Thr His
        515                 520                 525

Thr Cys Pro Pro Cys Pro Ala Pro Glu Leu Leu Gly Gly Pro Ser Val
530                 535                 540

Phe Leu Phe Pro Pro Lys Pro Lys Asp Thr Leu Met Ile Ser Arg Thr
545                 550                 555                 560

Pro Glu Val Thr Cys Val Val Asp Val Ser His Glu Asp Pro Gln
                565                 570                 575

Val Lys Phe Asn Trp Tyr Val Asp Gly Val Gln Val His Asn Ala Lys
                580                 585                 590

Thr Lys Pro Arg Glu Gln Gln Tyr Asn Ser Thr Tyr Arg Val Val Ser
                595                 600                 605

Val Leu Thr Val Leu His Gln Asn Trp Leu Asp Gly Lys Glu Tyr Lys
        610                 615                 620

Cys Lys Val Ser Asn Lys Ala Leu Pro Ala Pro Ile Glu Lys Thr Ile
625                 630                 635                 640

Ser Lys Ala Lys Gly Gln Pro Arg Glu Pro Gln Val Tyr Thr Leu Pro
                645                 650                 655

Pro Ser Arg Glu Glu Met Thr Lys Asn Gln Val Ser Leu Thr Cys Leu
                660                 665                 670

Val Lys Gly Phe Tyr Pro Ser Asp Ile Ala Val Glu Trp Glu Ser Asn
        675                 680                 685

Gly Gln Pro Glu Asn Asn Tyr Lys Thr Thr Pro Val Leu Asp Ser
        690                 695                 700

Asp Gly Ser Phe Phe Leu Tyr Ser Lys Leu Thr Val Asp Lys Ser Arg
705                 710                 715                 720

Trp Gln Gln Gly Asn Val Phe Ser Cys Ser Val Met His Glu Ala Leu
                725                 730                 735

His Asn His Tyr Thr Gln Lys Ser Leu Ser Leu Ser Pro Gly Lys
                740                 745                 750

<210> SEQ ID NO 10
<211> LENGTH: 539
<212> TYPE: PRT
<213> ORGANISM: Artificial Sequence
<220> FEATURE:
<223> OTHER INFORMATION: Synthetic polymer

<400> SEQUENCE: 10

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
                20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
        50                  55                  60

```
Val Pro Thr Val Thr Ala Thr Arg Ile Leu Lys Gly Gln Met Asn Gly
 65                  70                  75                  80

Lys Leu Gly Pro Glu Thr Pro Leu Ala Met Asp Gln Phe Pro Tyr Val
                 85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Arg Tyr Asn Gln Cys Asn Thr Thr Ser
    130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
        355                 360                 365

Thr Leu Ile Leu Ala Thr Ala Asp His Ser His Val Phe Ser Phe Gly
370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
        435                 440                 445

Glu Ser His Gly Gly Glu Asp Val Ala Val Phe Ala Arg Gly Pro Gln
450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Glu
```

```
                    485                 490                 495
Val Leu Phe Gln Gly Pro Ala Pro Ala Gly Thr Thr Asp Ala Ala
                500                 505                 510

His Pro Gly Arg Ser Val Val Pro Ala Leu Leu Pro Leu Arg Ala Gly
            515                 520                 525

Thr Leu Leu Leu Glu Thr Ala Thr Ala Pro
    530                 535

<210> SEQ ID NO 11
<211> LENGTH: 534
<212> TYPE: PRT
<213> ORGANISM: Artificial Sequence
<220> FEATURE:
<223> OTHER INFORMATION: Synthetic polymer

<400> SEQUENCE: 11

Met Gln Trp Ala Cys Val Leu Leu Leu Gly Leu Trp Leu Gln Leu
1               5                   10                  15

Ser Leu Thr Phe Ile Pro Ala Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Ala Arg Tyr Asn Gln Cys Asn Thr Thr Ser
    130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
    210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
    290                 295                 300

Pro Thr Leu Glu Glu Met Thr Glu Ala Ala Leu Gln Val Leu Ser Arg
```

```
            305                 310                 315                 320
Asn Pro Gln Gly Phe Tyr Leu Phe Val Glu Gly Gly Arg Ile Asp His
                325                 330                 335
Gly His His Glu Gly Lys Ala Tyr Met Ala Leu Thr Asp Thr Val Met
            340                 345                 350
Phe Asp Asn Ala Ile Ala Lys Ala Asn Glu Leu Thr Ser Glu Leu Asp
                355                 360                 365
Thr Leu Ile Leu Ala Thr Ala Asp His Ser His Val Phe Ser Phe Gly
    370                 375                 380
Gly Tyr Thr Leu Arg Gly Thr Ser Ile Phe Gly Leu Ala Pro Ser Lys
385                 390                 395                 400
Ala Ser Asp Asn Lys Ser Tyr Thr Ser Ile Leu Tyr Gly Asn Gly Pro
                405                 410                 415
Gly Tyr Val Leu Gly Gly Leu Arg Pro Asp Val Asn Asp Ser Ile
            420                 425                 430
Ser Glu Asp Pro Ser Tyr Arg Gln Gln Ala Ala Val Pro Leu Ser Ser
                435                 440                 445
Glu Ser His Gly Gly Glu Asp Val Ala Val Phe Ala Arg Gly Pro Gln
    450                 455                 460
Ala His Leu Val His Gly Val Gln Glu Glu Thr Phe Val Ala His Val
465                 470                 475                 480
Met Ala Phe Ala Gly Cys Val Glu Pro Tyr Thr Asp Cys Asn Leu Ala
                485                 490                 495
Pro Pro Ala Gly Thr Thr Asp Ala Ala His Pro Ile Glu Gly Arg Ser
                500                 505                 510
Val Val Pro Ala Leu Leu Pro Leu Arg Ala Gly Thr Leu Leu Leu Leu
            515                 520                 525
Glu Thr Ala Thr Ala Pro
    530

<210> SEQ ID NO 12
<211> LENGTH: 1669
<212> TYPE: DNA
<213> ORGANISM: Artificial Sequence
<220> FEATURE:
<223> OTHER INFORMATION: Synthetic polymer

<400> SEQUENCE: 12 atgcagggc cctgggtgct gctgctgctg ggcctgaggc tacagctctc cctgggcgtc      60
atcccaggta atgaggctcc ccaagctgtt ccacacacag gcacccccct cagccaggct    120
gacctgatct ctactctccc cctggccagc tgaggaggag aacccggcct tctggaaccg    180
ccaggcagct gaggccctgg atgctgccaa gaagctgcag cccatccaga aggtcgccaa    240
gaacctcatc ctcttcctgg gcgatgggtt ggggggtgccc acggtgacag ccaccaggat    300
cctaaagggg cagaagaatg caaactgggg gcctgagacg cccctggcca tggaccgctt    360
cccatacctg gctctgtcca agacatacaa tgtggacaga caggtgccag acagcgcagc    420
cacagccacg gcctacctgt gcggggtcaa ggccaacttc agaccatcg gcttgagtgc    480 agccgcccgc tttaaccagt gcaacacgac acgcggcaat gaggtcatct ccgtgatgaa    540
ccgggccaag caagcaggaa agtcagtagg agtggtgacc accacacggg tgcagcacgc    600
ctcgccagcc ggcacctacg cacacacagt gaaccgcaac tggtactcag atgctgacat    660
gcctgcctca gcccgccagg aggggtgcca ggacatcgcc actcagctca tctccaacat    720
ggacattgac gtgatccttg gcggaggccg caagtacatg tttcccatgg ggaccccaga    780
```

```
ccctgagtac  ccagctgatg  ccagccagaa  tggaatcagg  ctggacggga  agaacctggt     840
gcaggaatgg  ctggcaaagc  accagggtgc  ctggtatgtg  tggaaccgca  ctgagctcat     900
gcaggcgtcc  ctggaccagt  ctgtgaccca  tctcatgggc  ctctttgagc  ccggagacac     960
gaaatatgag  atccaccgag  accccacact  ggacccctcc  ctgatggaga  tgacagaggc    1020
tgccctgcgc  ctgctgagca  ggaaccccg   cggcttctac  ctctttgtgg  agggcggccg    1080
catcgaccat  ggtcatcatg  agggtgtggc  ttaccaggca  ctcactgagg  cggtcatgtt    1140
cgacgacgcc  attgagaggg  cgggccagct  caccagcgag  gaggacacgc  tgaccctcgt    1200
caccgctgac  cactcccatg  tcttctcctt  tggtggctac  accttgcgag  ggagctccat    1260 cttcggggttg gccccagca   aggctcagga  cagcaaagcc  tacacgtcca  tcctgtacgg    1320
caatggcccg  ggctacgtgt  tcaactcagg  cgtgcgacca  gacgtgaatg  agagcgagag    1380
cgggagcccc  gattaccagc  agcaggcggc  ggtgcccctg  tcgtccgaga  cccacggagg    1440
cgaagacgtg  gcggtgtttg  cgcgcggccc  gcaggcgcac  ctggtgcatg  tgtgcagga    1500 gcagagcttc  gtagcgcatg  tcatggcctt  cgctgcctgt  ctggagccct  acacggcctg    1560
cgacctggcg  cctcccgcct  gcaccaccga  cgccgcgcac  ccagttgccg  cgtcgctgcc    1620
actgctggcc  gggaccctgc  tgctgctggg  ggcgtccgct  gctccctga                 1669

<210> SEQ ID NO 13
<211> LENGTH: 1671
<212> TYPE: DNA
<213> ORGANISM: Artificial Sequence
<220> FEATURE:
<223> OTHER INFORMATION: Synthetic polymer

<400> SEQUENCE: 13
atgcaggggc  cctgggtgct  gctgctgctg  ggcctgaggc  tacagctctc  cctgggcgtc      60
atcccagctg  aggaggagaa  cccggccttc  tggaaccgcc  aggcagctga  ggccctggat     120
gctgccaaga  agctgcagcc  catccagaag  gtcgccaaga  acctcatcct  cttcctgggc     180
gatgggttgg  gggtgcccac  ggtgacagca  accaggatcc  taaagggca   gaagaatggc     240 aaactggggc  ctgagacgcc  cctggccatg  gaccgcttcc  cataccctggc tctgtccaag     300 acatacaatg  tggacagaca  ggtgccagac  agcgcagcca  cagccacggc  ctacctgtgc     360
ggggtcaagg  ccaacttcca  gaccatcggc  ttgagtgcag  ccgcccgctt  taaccagtgc     420
aacacgacac  gcggcaatga  ggtcatctcc  gtgatgaacc  gggccaagca  agcaggaaag     480
tcagtaggag  tggtgaccac  cacacgggtg  cagcacgcct  cgccagccgg  cacctacgca     540
cacacagtga  accgcaactg  gtactcagat  gctgacatgc  ctgcctcagc  ccgccaggag     600
gggtgccagg  acatcgccac  tcagctcatc  tccaacatgg  acattgacgt  gatccttggc    660
ggaggccgca  agtacatgtt  tcccatgggg  accccagacc  ctgagtaccc  agctgatgcc    720
agccagaatg  gaatcaggct  ggacgggaag  aacctggtgc  aggaatggct  ggcaaagcac    780
cagggtgcct  ggtatgtgtg  gaaccgcact  gagctcatgc  aggcgtccct  ggaccagtct    840
gtgacccatc  tcatgggcct  ctttgagccc  ggagacacga  aatatgagat  ccaccgagac    900
cccacactgg  acccctccct  gatggagatg  acagaggctg  ccctgcgcct  gctgagcagg    960 aaccccgcg   gcttctacct  ctttgtggag  ggcggccgca  tcgaccatgg  tcatcatgag   1020
ggtgtggctt  accaggcact  cactgaggcg  gtcatgttcg  acgacgccat  tgagagggcg   1080
ggccagctca  ccagcgagga  ggacacgctg  accctcgtca  ccgctgacca  ctcccatgtc   1140
```

| | |
|---|---|
| ttctcctttg gtggctacac cttgcgaggg agctccatct tcgggttggc ccccagcaag | 1200 |
| gctcaggaca gcaaagccta cacgtccatc ctgtacggca atggcccggg ctacgtgttc | 1260 |
| aactcaggcg tgcgaccaga cgtgaatgag agcgagagcg ggagccccga ttaccagcag | 1320 |
| caggcggcgg tgcccctgtc gtccgagacc cacggaggcg aagacgtggc ggtgttttgcg | 1380 |
| cgcggcccgc aggcgcacct ggtgcatggt gtgcaggagc agagcttcgt agcgcatgtc | 1440 |
| atggccttcg ctgcctgtct ggagccctac acggcctgcg acctggcgcc tcccgcctgc | 1500 |
| accaccgacg ccgcgcaccc agttgccgcg tcgctgccac tgctggccgg gaccctgctg | 1560 |
| ctgctggggg cgtccgctgc tccctgattt actaaaacct tgaaataaaa ttgtaaaaca | 1620 |
| tcagtttgaa ggcctgactc tcagggtagt tcttttttaa ttctgggttt t | 1671 |

<210> SEQ ID NO 14
<211> LENGTH: 1672
<212> TYPE: DNA
<213> ORGANISM: Artificial Sequence
<220> FEATURE:
<223> OTHER INFORMATION: Synthetic polymer

<400> SEQUENCE: 14

| | |
|---|---|
| atgcagtggg cctgtgtgct gctgctgctg ggcctgtggc tacagctctc cctcaccttc | 60 |
| atcccaggta atcaggcggc tcccagcagc cctactcac aggggcggct ctaggctgac | 120 |
| ctgaccaaca ctctcccctt gggcagctga ggaggaagac cccgccttct ggaaccgcca | 180 |
| ggcagcccag gcccttgatg tagccaagaa gttgcagccg atccagacag ctgccaagaa | 240 |
| tgtcatcctc ttcttggggg atgggatggg ggtgcctacg gtgacagcca ctcggatcct | 300 |
| aaaggggcag atgaatggta agctgggacc tgagacaccc ctggccatgg accagttccc | 360 |
| atacgtggct ctgtccaaga catcaacgt ggacagacag tgccagaca gcgcaggcac | 420 |
| tgccactgcc tacctgtgtg gggtcaaggg caactacaaa accattggtg taagtgcagc | 480 |
| cgcccgctac aaccagtgca acacaacaag tggcaatgag gtcacgtctg tgatgaaccg | 540 |
| ggccaagaaa gcaggaaagt cagtgggagt ggtgaccacc tccagggtgc agcatgcctc | 600 |
| cccagccggt gcttatgcac acacggtgaa ccgaaactgg tactcagatg ccgacctgcc | 660 |
| tgccgatgca cagacgtatg gctgccagga tcgccaca caactggtca caacatgga | 720 |
| tattgacgtg atcctgggtg gaggccgaat gtacatgttt cctgagggga ccccggatcc | 780 |
| tgaataccca tacgatgtca atcagactgg agtccggaag acaagcgga atctggtgca | 840 |
| ggagtggcag gccaagcacc agggagccca gtatgtgtgg aaccgcacgg agctccttca | 900 |
| ggcagccaat gaccccagtg taacacacct catgggcctc tttgagccgg cagacatgaa | 960 |
| gtataatgtt cagcaagacc ccaccaagga cccgaccctg aggagatga cggaggcggc | 1020 |
| cctgcaagtg ctgagcagga accccagggg cttctacctc ttcgtggagg aggccgcat | 1080 |
| tgaccacggt caccatgaag gcaaagctta tggcactg actgatacag tcatgtttga | 1140 |
| caatgccatc gccaaggcta acgagctcac tagcgaactg acacgctga tccttgccac | 1200 |
| tgcagaccac tcccatgtct tctcttttgg tggctacaca ctgcgtggga cctccatttt | 1260 |
| cggtctggcc cccagcaagg cctcagacaa caagtcctac acctccatcc tctatggcaa | 1320 |
| tggccctggc tacgtgcttg gtgggggctt aaggcccgat gttaatgaca gcataagcga | 1380 |
| ggaccctcg taccgcagc aggcggccgt gccctgtct agtgagtccc acggggcga | 1440 |
| ggacgtggcg gtgttcgcgc gaggcccgca ggcgcacctg gtgcacgcg tgcaggagga | 1500 |
| gaccttcgtg gcgcacgtca tggccttttgc gggctgcgtg gagccctaca ccgactgcaa | 1560 |

```
tctgccggcc ccctctggcc tctccgacgc cgcgcacctg gcggccagcc cgccttcgct    1620
ggcgctgctg gccggggcga tgctgctgct gctggcgcct gccttgtact ga           1672

<210> SEQ ID NO 15
<211> LENGTH: 1869
<212> TYPE: DNA
<213> ORGANISM: Artificial Sequence
<220> FEATURE:
<223> OTHER INFORMATION: Synthetic polymer

<400> SEQUENCE: 15
atgcagtggg cctgtgtgct gctgctgctg ggctgtggc tacagctctc cctcaccttc      60
atcccagctg aggaggaaga ccccgccttc tggaaccgcc aggcagccca ggcccttgat    120
gtagccaaga agttgcagcc gatccagaca gctgccaaga atgtcatcct cttcttgggg    180
gatgggatgg gggtgcctac ggtgacagcc actcggatcc taaaggggca gatgaatggt    240
aagctgggac ctgagacacc cctggccatg accagttcc catacgtggc tctgtccaag     300
acatacaacg tggacagaca ggtgccagac agcgcaggca ctgccactgc ctacctgtgt    360
ggggtcaagg gcaactacaa aaccattggt gtaagtgcag ccgcccgcta caaccagtgc    420
aacacaacaa gtggcaatga ggtcacgtct gtgatgaacc gggccaagaa agcaggaaag    480
tcagtgggag tggtgaccac ctccagggtg cagcatgcct ccccagccgg tgcttatgca    540
cacacggtga accgaaactg gtactcagat gccgacctgc ctgccgatgc acagacgtat    600
ggctgccagg acatcgccac acaactggtc aacaacatgg atattgacgt gatcctgggt    660
ggaggccgaa tgtacatgtt tcctgagggg accccggatc ctgaataccc atacgatgtc    720
aatcagactg gagtccggaa ggacaagcgg aatctggtgc aggagtggca ggccaagcac    780
cagggagccc agtatgtgtg gaaccgcacg gagctccttc aggcagccaa tgaccccagt    840
gtaacacacc tcatgggcct ctttgagccg gcagacatga gtataatgt tcagcaagac    900 cccaccaagg acccgaccct ggaggagatg acggaggcgg ccctgcaagt gctgagcagg    960 aaccccagg gcttctacct cttcgtggag ggaggccgca ttgaccacgg tcaccatgaa   1020
ggcaaagctt atatggcact gactgataca gtcatgtttg acaatgccat cgccaaggct   1080
aacgagctca ctagcgaact ggacacgctg atccttgcca ctgcagacca ctcccatgtc   1140 ttctctttg gtggctacac actgcgtggg acctccattt tcggtctggc ccccagcaag   1200
gcctcagaca caagtcctca cacctccatc ctctatggca atggccctgg ctacgtgctt   1260 ggtggggct aaggcccga tgttaatgac agcataagcg aggaccctc gtaccggcag     1320 caggcggccg tgcccctgtc tagtgagtcc cacggggcg aggacgtggc ggtgttcgcg   1380
cgaggcccgc aggcgcacct ggtgcacggc gtgcaggagg agaccttcgt ggcgcacgtc   1440
atggcctttg cgggctgcgt ggagccctac accgactgca atctgccggc ccctctggcc   1500
ctctccgacg ccgcgcacct ggcggccagc ccgccttcgc tggcgctgct ggccggggcg   1560
atgctgctgc tgctggcgcc tgccttgtac tgaggggacc cggggtgggg gacacaggcc   1620
ccgccctccc tgggaggcag gaagcagctc tcaaataaac tgttctaagt atgatacagg   1680
agtgatacat gtgtgaagag aagcccttag gtgggggcac agagtgtctg ggtgaggggg   1740
gtcagggtca catcaggagg ttagggaggg gttgatgaag gctgacgtt gagcaaagac    1800 caaaggcaac tcagaaggac agtggtgcag gactgggtgt ggtcagcagg gggactggtt   1860
gggggatcc                                                           1869
```

<210> SEQ ID NO 16
<211> LENGTH: 1260
<212> TYPE: DNA
<213> ORGANISM: Artificial Sequence
<220> FEATURE:
<223> OTHER INFORMATION: Synthetic polymer

<400> SEQUENCE: 16

```
aaaaaacaag acaaagctga gatcagaaat gtcattgtga tgataggcga cggcatgggg      60
acgccttaca taagagccta ccgttccatg aaaaataacg gtgacacacc gaataacccg     120
aagttaacag aatttgaccg gaacctgaca ggcatgatga tgacgcatcc ggatgaccct     180
gactataata ttacagattc agcagcagcc ggaacagcat tagcgacagg cgttaagaca     240
tataacaatg caattggcgt cgataaaaac ggaaaaaaag tgaaatctgt acttgaagag     300
gccaaacagc aaggcaagtc aacagggctt gtcgccacgt ctgaaattaa ccacgccact     360
ccagccgcat atggcgccca caatgaatca cggaaaaaca tggaccaaat cgccaacagc     420
tatatggatg acaagataaa aggcaaacat aaaatagacg tgctgctcgg cggcggaaaa     480
tcttatttta accgcaagaa cagaaacttg acaaaggaat tcaaacaagc cggctacagc     540
tatgtgacaa ctaaacaagc attgaaaaaa ataaagatc agcaggtgct cgggcttttc     600
gcagatggag ggcttgctaa agcgctcgac cgtgacagta aaacaccgtc tctcaaagac     660
atgacggttt cagcaattga tcgcctgaac caaaataaaa aaggatttt cttgatggtc     720
gaagggagcc agattgactg ggcggcccat gacaatgata cagtaggagc catgagcgag     780
gttaaagatt tgaacaggc ctataaagcc gcgattgaat tgcgaaaaa agacaaacat     840
acacttgtga ttgcaactgc tgaccataca accggcggct ttaccattgg cgcaaacggg     900
gaaaagaatt ggcacgcaga accgattctc tccgctaaga aaacacctga attcatggcc     960
aaaaaaatca gtgaaggcaa gccggttaaa gatgtgctcg cccgctatgc caatctgaaa    1020
gtcacatctg aagaaatcaa aagcgttgaa gcagctgcac aggctgacaa agcaaaggg    1080
gcctccaaag ccatcatcaa gatttttaat acccgctcca cagcggatg gacgagtacc    1140
gatcataccg gcgaagaagt accggtatac gcgtacggcc ccggaaaaga aaaattccgc    1200
ggattgatta caatacgga ccaggcaaac atcatatta agattttaaa aactggaaaa    1260
```

<210> SEQ ID NO 17
<211> LENGTH: 420
<212> TYPE: PRT
<213> ORGANISM: Artificial Sequence
<220> FEATURE:
<223> OTHER INFORMATION: Synthetic polymer

<400> SEQUENCE: 17

```
Lys Lys Gln Asp Lys Ala Glu Ile Arg Asn Val Ile Val Met Ile Gly
 1               5                  10                  15

Asp Gly Met Gly Thr Pro Tyr Ile Arg Ala Tyr Arg Ser Met Lys Asn
            20                  25                  30

Asn Gly Asp Thr Pro Asn Asn Pro Lys Leu Thr Glu Phe Asp Arg Asn
        35                  40                  45

Leu Thr Gly Met Met Met Thr His Pro Asp Pro Asp Tyr Asn Ile
    50                  55                  60

Thr Asp Ser Ala Ala Ala Gly Thr Ala Leu Ala Thr Gly Val Lys Thr
65                  70                  75                  80

Tyr Asn Asn Ala Ile Gly Val Asp Lys Asn Gly Lys Lys Val Lys Ser
                85                  90                  95
```

Val Leu Glu Glu Ala Lys Gln Gln Gly Lys Ser Thr Gly Leu Val Ala
            100                 105                 110

Thr Ser Glu Ile Asn His Ala Thr Pro Ala Ala Tyr Gly Ala His Asn
        115                 120                 125

Glu Ser Arg Lys Asn Met Asp Gln Ile Ala Asn Ser Tyr Met Asp Asp
130                 135                 140

Lys Ile Lys Gly Lys His Lys Ile Asp Val Leu Leu Gly Gly Gly Lys
145                 150                 155                 160

Ser Tyr Phe Asn Arg Lys Asn Arg Asn Leu Thr Lys Glu Phe Lys Gln
                165                 170                 175

Ala Gly Tyr Ser Tyr Val Thr Thr Lys Gln Ala Leu Lys Asn Lys
            180                 185                 190

Asp Gln Gln Val Leu Gly Leu Phe Ala Asp Gly Gly Leu Ala Lys Ala
        195                 200                 205

Leu Asp Arg Asp Ser Lys Thr Pro Ser Leu Lys Asp Met Thr Val Ser
210                 215                 220

Ala Ile Asp Arg Leu Asn Gln Asn Lys Lys Gly Phe Phe Leu Met Val
225                 230                 235                 240

Glu Gly Ser Gln Ile Asp Trp Ala Ala His Asp Asn Asp Thr Val Gly
                245                 250                 255

Ala Met Ser Glu Val Lys Asp Phe Gln Ala Tyr Lys Ala Ala Ile
            260                 265                 270

Glu Phe Ala Lys Lys Asp Lys His Thr Leu Val Ile Ala Thr Ala Asp
        275                 280                 285

His Thr Thr Gly Gly Phe Thr Ile Gly Ala Asn Gly Glu Lys Asn Trp
290                 295                 300

His Ala Glu Pro Ile Leu Ser Ala Lys Lys Thr Pro Glu Phe Met Ala
305                 310                 315                 320

Lys Lys Ile Ser Glu Gly Lys Pro Val Lys Asp Val Leu Ala Arg Tyr
                325                 330                 335

Ala Asn Leu Lys Val Thr Ser Glu Glu Ile Lys Ser Val Glu Ala Ala
            340                 345                 350

Ala Gln Ala Asp Lys Ser Lys Gly Ala Ser Lys Ala Ile Ile Lys Ile
        355                 360                 365

Phe Asn Thr Arg Ser Asn Ser Gly Trp Thr Ser Thr Asp His Thr Gly
370                 375                 380

Glu Glu Val Pro Val Tyr Ala Tyr Gly Pro Gly Lys Glu Lys Phe Arg
385                 390                 395                 400

Gly Leu Ile Asn Asn Thr Asp Gln Ala Asn Ile Ile Phe Lys Ile Leu
                405                 410                 415

Lys Thr Gly Lys
            420

<210> SEQ ID NO 18
<211> LENGTH: 776
<212> TYPE: PRT
<213> ORGANISM: Artificial Sequence
<220> FEATURE:
<223> OTHER INFORMATION: Synthetic polymer

<400> SEQUENCE: 18

Met Gln Gly Pro Trp Val Leu Leu Leu Gly Leu Arg Leu Gln Leu
1               5                   10                  15

Ser Leu Gly Val Ile Pro Ala Glu Glu Asn Pro Ala Phe Trp Asn
            20                  25                  30

```
Arg Gln Ala Ala Glu Ala Leu Asp Ala Ala Lys Lys Leu Gln Pro Ile
             35                  40                  45
Gln Lys Val Ala Lys Asn Leu Ile Leu Phe Leu Gly Asp Gly Leu Gly
 50                  55                  60
Val Pro Thr Val Thr Ala Thr Arg Ile Leu Lys Gly Gln Lys Asn Gly
 65                  70                  75                  80
Lys Leu Gly Pro Glu Thr Pro Leu Ala Met Asp Arg Phe Pro Tyr Leu
                 85                  90                  95
Ala Leu Ser Lys Thr Tyr Asn Val Asp Arg Gln Val Pro Asp Ser Ala
                100                 105                 110
Ala Thr Ala Thr Ala Tyr Leu Cys Gly Val Lys Ala Asn Phe Gln Thr
            115                 120                 125
Ile Gly Leu Ser Ala Ala Arg Phe Asn Gln Cys Asn Thr Thr Arg
            130                 135                 140
Gly Asn Glu Val Ile Ser Val Met Asn Arg Ala Lys Gln Ala Gly Lys
145                 150                 155                 160
Ser Val Gly Val Val Thr Thr Thr Arg Val Gln His Ala Ser Pro Ala
                165                 170                 175
Gly Thr Tyr Ala His Thr Val Asn Arg Asn Trp Tyr Ser Asp Ala Asp
            180                 185                 190
Met Pro Ala Ser Ala Arg Gln Glu Gly Cys Gln Asp Ile Ala Thr Gln
            195                 200                 205
Leu Ile Ser Asn Met Asp Ile Asp Val Ile Leu Gly Gly Gly Arg Lys
210                 215                 220
Tyr Met Phe Pro Met Gly Thr Pro Asp Pro Glu Tyr Pro Ala Asp Ala
225                 230                 235                 240
Ser Gln Asn Gly Ile Arg Leu Asp Gly Lys Asn Leu Val Gln Glu Trp
            245                 250                 255
Leu Ala Lys His Gln Gly Ala Trp Tyr Val Trp Asn Arg Thr Glu Leu
            260                 265                 270
Met Gln Ala Ser Leu Asp Gln Ser Val Thr His Leu Met Gly Leu Phe
            275                 280                 285
Glu Pro Gly Asp Thr Lys Tyr Glu Ile His Arg Asp Pro Thr Leu Asp
290                 295                 300
Pro Ser Leu Met Glu Met Thr Glu Ala Ala Leu Arg Leu Leu Ser Arg
305                 310                 315                 320
Asn Pro Arg Gly Phe Tyr Leu Phe Val Glu Gly Gly Arg Ile Asp His
            325                 330                 335
Gly His His Glu Gly Val Ala Tyr Gln Ala Leu Thr Glu Ala Val Met
            340                 345                 350
Phe Asp Asp Ala Ile Glu Arg Ala Gly Gln Leu Thr Ser Glu Glu Asp
            355                 360                 365
Thr Leu Thr Leu Val Thr Ala Asp His Ser His Val Phe Ser Phe Gly
370                 375                 380
Gly Tyr Thr Leu Arg Gly Ser Ser Ile Phe Gly Leu Ala Pro Ser Lys
385                 390                 395                 400
Ala Gln Asp Ser Lys Ala Tyr Thr Ser Ile Leu Tyr Gly Asn Gly Pro
            405                 410                 415
Gly Tyr Val Phe Asn Ser Gly Val Arg Pro Asp Val Asn Glu Ser Glu
            420                 425                 430
```

-continued

```
Ser Gly Ser Pro Asp Tyr Gln Gln Gln Ala Ala Val Pro Leu Ser Ser
        435                 440                 445

Glu Thr His Gly Gly Glu Asp Val Ala Val Phe Ala Arg Gly Pro Gln
450             455                 460

Ala His Leu Val His Gly Val Gln Glu Gln Ser Phe Val Ala His Val
465             470                 475                 480

Met Ala Phe Ala Ala Cys Leu Glu Pro Tyr Thr Ala Cys Asp Leu Ala
            485                 490                 495

Pro Pro Ala Cys Thr Asp Ala Ala His Pro Val Ala Ala Ser Leu
            500             505             510

Pro Leu Leu Ala Gly Thr Leu Leu Leu Gly Ala Ser Ala Ala Pro
        515             520             525

Gly Gly Ser Gly Gly Ser Gly Gly Gly Ser Gly Gly Gly Gly Ser
        530             535             540

Glu Pro Lys Ser Cys Asp Lys Thr His Thr Cys Pro Pro Cys Pro Ala
545             550             555             560

Pro Glu Leu Leu Gly Gly Pro Ser Val Phe Leu Phe Pro Pro Lys Pro
            565             570             575

Lys Asp Thr Leu Met Ile Ser Arg Thr Pro Glu Val Thr Cys Val Val
            580             585             590

Val Asp Val Ser His Glu Asp Pro Gln Val Lys Phe Asn Trp Tyr Val
            595             600             605

Asp Gly Val Gln Val His Asn Ala Lys Thr Lys Pro Arg Glu Gln Gln
        610             615             620

Tyr Asn Ser Thr Tyr Arg Val Val Ser Val Leu Thr Val Leu His Gln
625             630             635             640

Asn Trp Leu Asp Gly Lys Glu Tyr Lys Cys Lys Val Ser Asn Lys Ala
            645             650             655

Leu Pro Ala Pro Ile Glu Lys Thr Ile Ser Lys Ala Lys Gly Gln Pro
            660             665             670

Arg Glu Pro Gln Val Tyr Thr Leu Pro Pro Ser Arg Glu Glu Met Thr
        675             680             685

Lys Asn Gln Val Ser Leu Thr Cys Leu Val Lys Gly Phe Tyr Pro Ser
        690             695             700

Asp Ile Ala Val Glu Trp Glu Ser Asn Gly Gln Pro Glu Asn Asn Tyr
705             710             715             720

Lys Thr Thr Pro Pro Val Leu Asp Ser Asp Gly Ser Phe Phe Leu Tyr
            725             730             735

Ser Lys Leu Thr Val Asp Lys Ser Arg Trp Gln Gln Gly Asn Val Phe
            740             745             750

Ser Cys Ser Val Met His Glu Ala Leu His Asn His Tyr Thr Gln Lys
        755             760             765

Ser Leu Ser Leu Ser Pro Gly Lys
770             775
```

ALKALINE PHOSPHATASE AGENTS FOR TREATMENT OF NEURODEVELOPMENTAL DISORDERS

CROSS-REFERENCE TO RELATED APPLICATIONS

This application is a National Stage Entry of International Patent Application No. PCT/US2019/012671, filed Jan. 8, 2019, which claims the benefit of U.S. Provisional Application No. 62/679,310, filed Jun. 1, 2018, and U.S. Provisional Application No. 62/615,227, filed Jan. 9, 2018, the contents of which are hereby incorporated by reference in their entireties.

TECHNICAL FIELD

The present invention relates, inter alia, to therapeutic alkaline phosphatases. The present invention further relates to compositions comprising the therapeutic alkaline phosphatases and use of the compositions in the treatment or prevention of neurodevelopmental disorders.

SEQUENCE LISTING

The instant application contains a Sequence Listing which has been submitted in ASCII format via EFS-Web and is hereby incorporated by reference in its entirety. The ASCII copy, created on Dec. 27, 2018, is 74.1 KB in size and is named SYN-034PC_ST25.txt.

BACKGROUND

Alkaline phosphatase ("APs," EC 3.1.3.1) is a hydrolase enzyme that can remove phosphate groups from various targets including nucleotides and proteins. Alkaline phosphatases are found in prokaryotic as well as eukaryotic organisms ranging from *E. coli* to mammals. In particular, mammalian APs have been shown to play important roles in gut hemostasis, mucosal barrier function, promotion of commensal bacteria, and defense from pathogens. Mammalian APs exert their properties by primarily targeting LPS (a TLR4 agonist), flagellin (a TLR5 agonist) and CpG DNA (a TLR9 agonist). APs also degrade intestine luminal NTPs (e.g., ATP, GTP, etc.), which promote the growth of good bacteria and reverses dysbiosis.

Neurodevelopmental disorders suffer from lack of treatments. Autism is a neurodevelopmental disorder characterized by impaired social interaction, verbal and non-verbal communication, and restricted and repetitive behavior. Globally, autism is estimated to affect 21.7 million people as of 2013. As of 2010, the number of people affected is estimated at about 1-2 per 1,000 worldwide. It occurs four to five times more often in boys than girls. About 1.5% of children in the United States (1 in 68) are diagnosed with Autism Spectrum Disorder (ASD) as of 2014, a 30% increase from one in 88 in 2012. There are currently no FDA-approved treatment for autism.

Currently, there are no approved AP-based therapeutics on the market. As such, there remains a need for novel AP-based therapeutic compositions for the prevention and treatment of neurodevelopmental diseases.

SUMMARY

Accordingly, in some aspects, the present invention provides various AP constructs ("AP-based agents") and therapeutic uses thereof. In various embodiments, the AP-based agent is a mammalian or bacterial alkaline phosphatase. In some embodiments, the AP-based agent is a mammalian alkaline phosphatase. In an embodiment, the AP-based agent is an intestinal alkaline phosphatase. In some embodiments, the AP-based agent is a bacterial alkaline phosphatase. In some embodiments, the bacterial alkaline phosphatase has catalytic activity comparable to that of a mammalian phosphatase. In some embodiments, the AP-based agent is secreted from the host cell.

In some aspects, the present invention provides methods for the therapeutic use of an AP-based agent. In an embodiment, the present invention provides methods for the treatment or prevention of one or more neurodevelopmental disorders.

DETAILED DESCRIPTION

Figure 1:
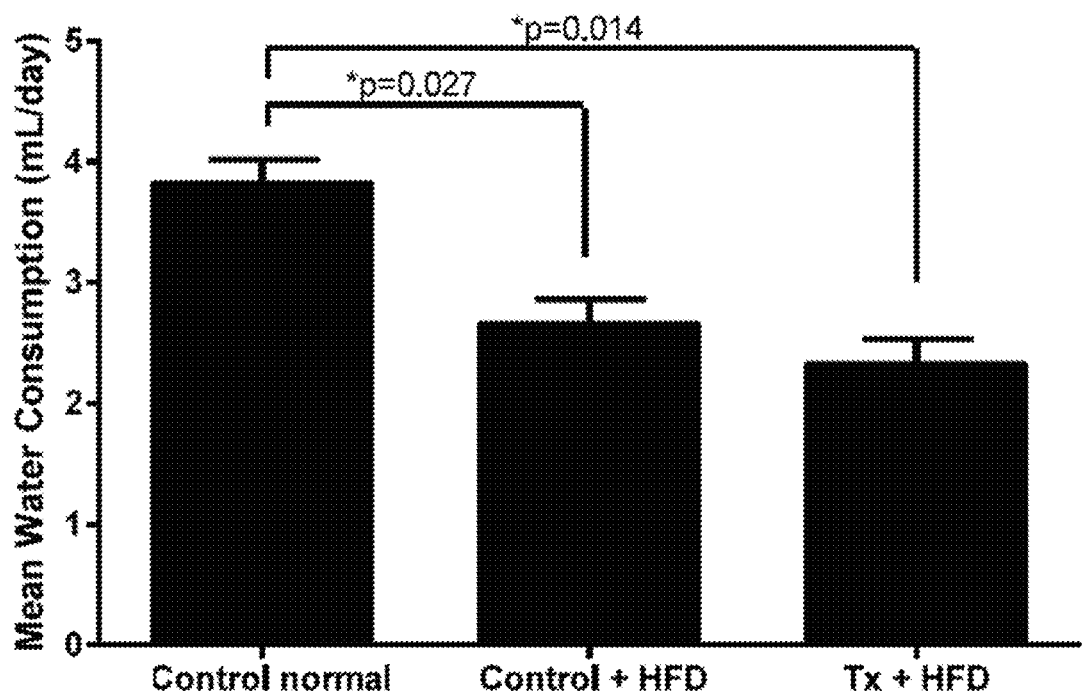
FIG. 1 depicts the mean water consumption over the first 8 weeks of dam feeding.

The present invention is based, in part, on the discovery that AP-based agents can be used in the treatment or prevention of one or more neurodevelopmental disorders, including ASD. For instance, the present invention relates, in part, to use of an AP-based agent, such as, without limitation, orally administered intestinal alkaline phosphatase (IAP), to prevent ASD in the offspring of a pregnant woman at risk for having a child afflicted with ASD (e.g. a pregnant woman having one or more risk factors for having a child with ASD, such as with one or more of gastrointestinal dysbiosis, obesity, metabolic syndrome, gut-mediated systemic inflammation, and leaky gut).

In various embodiments, the present invention relates to the treatment or prevention of a neurodevelopmental disorder, e.g., ASD, in an unborn child or newly born child. For instance, in various embodiments, the present AP-based agent is administered to a mother or expecting mother, where the mother is afflicted with one or more of gastrointestinal dysbiosis, obesity, metabolic syndrome, gut-mediated systemic inflammation, and leaky gut and/or the mother or expecting mother has a high fat diet. In various embodiments, the mother or expecting mother is at risk for having a child with a neurodevelopmental disorder, e.g., ASD, by being afflicted with one or more of gastrointestinal dysbiosis, obesity, metabolic syndrome, gut-mediated systemic inflammation, and leaky gut and/or having a high fat diet, and the present method reduces the likelihood or severity of the neurodevelopmental disorder, e.g., ASD, in the unborn child or newly born child of the mother or expecting mother. In various embodiments, the unborn child is in the first, or second, or third trimester. For example, the administration of the present AP-based agent occurs in the first, or second, or third trimester. In various embodiments, the newly born child is less than 1, or 1, or 2, or 3, or 6, or 9 or 12, or 15, or 18, or 21, or 24 months old. In various embodiments, the newly born child is receiving nutrition from the mother via breast milk (e.g. breast feeding). For example, the administration of the present AP-based agent occurs 1, or 1, or 2, or 3, or 6, or 9 or 12, or 15, or 18, or 21, or 24 months after delivery of the child.

Alkaline Phosphatase-Based Agents and Pharmaceutical Compositions

The present invention is directed, in part, to pharmaceutical compositions, formulations, and uses of one or more alkaline phosphatase-based agents (AP-based agents). Alkaline phosphatases are dimeric metalloenzymes that catalyze the hydrolysis of phosphate esters and dephosphoryl ate a variety of target substrates at physiological and higher pHs. Alkaline phosphatases are found in prokaryotic as well as in eukaryotic organisms (e.g., in *E. coli* and mammals). Illustrative AP-based agents that may be utilized in the present invention include, but are not limited to, intestinal alkaline phosphatase (IAP; e.g., calf IAP or bovine IAP, chicken IAP, goat IAP), placental alkaline phosphatase (PLAP), placental-like alkaline phosphatase, germ cell alkaline phosphatase (GCAP), tissue non-specific alkaline phosphatase (TNAP; which is primarily found in the liver, kidney, and bone), bone alkaline phosphatase, liver alkaline phosphatase, kidney alkaline phosphatase, bacterial alkaline phosphatase, fungal alkaline phosphatase, shrimp alkaline phosphatase, modified IAP, recombinant IAP, or any polypeptide comprising alkaline phosphatase activity.

In various embodiments, the present invention contemplates the use of mammalian alkaline phosphatases including, but are not limited to, intestinal alkaline phosphatase (IAP), placental alkaline phosphatase (PLAP), germ cell alkaline phosphatase (GCAP), and the tissue non-specific alkaline phosphatase (TNAP).

In some embodiments, the AP-based agent is IAP. IAP is produced in the proximal small intestine and is bound to the enterocytes via a GPI anchor. Some IAP is released into the intestinal lumen in conjunction with vesicles shed by the cells and as soluble protein stripped from the cells via phospholipases. The enzyme then traverses the small and large intestine such that some active enzyme can be detected in the feces. In an embodiment, the IAP is human IAP (hIAP). In an embodiment, the IAP is calf IAP (cIAP), also known as bovine IAP (bIAP). There are multiple isozymes of bIAP, for example, with bIAP II and IV having higher specific activity than bIAP I. In an embodiment, the IAP is any one of the cIAP or bIAP isozymes (e.g., bIAP I, II, and IV). In an embodiment, the IAP is bIAP II. In another embodiment, the IAP is bIAP IV.

In various embodiments, the AP-based agent is hIAP or a variant thereof. In some embodiments, the AP-based agent is hIAP comprising the amino acid sequence of SEQ ID NO:1 as depicted below.

```
HIAP
                                                              SEQ ID NO: 1
  1 mqgpwvllll glrlqlslgv ipaeeenpaf wnrqaaeald aakklqpiqk vaknlilflg 61 dglgvptvta trilkgqkng klgpetplam drfpylalsk tynvdrqvpd saatataylc 121 gvkanfqtig lsaaarfnqc nttrgnevis vmnrakqagk svgvvtttrv qhaspagtya 181 htvnrnwysd admpasarqe gcgdiatqli snmdidvilg ggrkymfpmg tpdpeypada 241 sqngirldgk nlvqewlakh qgawyvwnrt elmgasldqs vthlmglfep gdtkyeihrd 301 ptldpslmem teaalrllsr nprgfylfve ggridhghhe gvayqaltea vmfddaiera 361 gqltseedtl tlvtadhshv fsfggytlrg ssifglapsk aqdskaytsi lygngpgyvf 421 nsgvrpdvne sesgspdygq qaavplsset hggedvavfa rgpqahlvhg vqeqsfvahv 481 mafaaclepy tacdlappac ttdaahpvaa slpllagtll llgasaap
```

Without wishing to be bound by theory, it is believed that a cysteine at the carboxy terminus of the AP-based agent (e.g., at position 500 of SEQ ID NO:1) may interfere with protein folding. Accordingly, in some embodiments, the AP-based agent includes a mutation of the cysteine (e.g., at position 500 of SEQ ID NO:1). In some embodiments, the cysteine is replaced with glycine.

In various embodiments, the AP-based agent is bIAP II or a variant thereof. In an embodiment, the bIAP II comprises the signal peptide and carboxy terminus of bIAP I. In an embodiment, the bIAP II comprises an aspartate and position 248 (similar to bIAP IV). In an embodiment, the bIAP II comprises the amino acid sequence of SEQ ID NO: 2:

```
BIAP II with 248D assignment - SEQ ID NO: 2. The signal peptide and
sequence past 480 are derived from bIAP I
  1 mqgacvllll glhlqlslgl ipaeeenpaf wnrqaaqald vakklqpiqt aaknvilflg 61 dgmgvptvta trilkgqmng klgpetplam dqfpyvalsk tynvdrqvpd sagtataylc 121 gvkgnyrtig vsaaarynqc nttrgnevts vinrakkagk avgvvtttrv qhaspagaya 181 htvnrnwysd adlpadaqkn gcqdiaaqlv ynmdidvilg ggrmymfpeg tpdpeypdda
```

```
-continued
241 svngvrkdkq nlvqewqakh qgaqyvwnrt allqaaddss vthlmglfep admkynvqqd 301 htkdptlaem teaalqvlsr nprgfylfve ggridhghhd gkaymaltea imfdnaiaka 361 neltseldtl ilvtadhshv fsfggytlrg tsifglapgk aldsksytsi lygngpgyal 421 gggsrpdvng stseepsyrq qaavplaset hggedvavfa rgpqahlvhg vqeetfvahi
```

481 mafagcvepy tdcnlpapat atsipdaahl aasppplall agamlll-laptly

In various embodiments, the AP-based agent is bIAP IV or a variant thereof. In an embodiment, the bIAP IV comprises the amino acid sequence of SEQ ID NO: 3:

```
BIAP IV
                                                           SEQ ID NO: 3
  1 mgwacvllll glwlqlsltf ipaeeedpaf wnrgaagald vakklqpiqt aaknvilflg 61 dgmgyptvta trilkgqmng klgpetplam dqfpyvalsk tynydrqvpd sagtataylc 121 gvkgnyktig vsaaarynqc nttsgnevts vmnrakkagk svgyyttsrv qhaspagaya 181 htvnrnwysd adlpadaqty gcgdiatqly nnmdidvilg ggrmymfpeg tpdpeypydv 241 nqtgyrkdkr nlygewqakh qgagyvwnrt ellqaandps vthlmglfep admkynvqqd 301 ptkdptleem teaalqvlsr npqgfylfve ggridhghhe gkaymaltdt vmfdnaiaka 361 neltseldtl ilatadhshv fsfggytlrg tsifglapsk asdnksytsi lygngpgyvl 421 ggglrpdynd sisedpsyrq qaavplsses hggedvavfa rgpqahlvhg vgeetfyahv 481 mafagcvepy tdcnlpapsg lsdaahlaas ppslallaga mllllapaly
```

Mammalian alkaline phosphatases are glycosylphosphatidyl-inositol (GPI) anchored proteins. They have signal peptides and are translated into the secretory pathway. Once in the endoplasmic reticulum (ER), the proteins are glycosylated and folded. There are two disulfide bonds as well as a single free cysteine that is apparently not accessible on the surface. In the late ER, the carboxy terminus is removed and the GPI anchor is appended. GPI anchoring is therefore a process that occurs at the carboxy terminus of the alkaline phosphatase. The inclusion of stop codons at the anchor site enables secretion of biologically active protein (presumably the homodimer). While there is no consensus sequence, the carboxy terminus includes three amino acids, termed omega, omega+1, and omega+2 which are followed by a short stretch of hydrophilic amino acids and then a stretch of hydrophobic amino acids. Without wishing to be bound by theory, it is believed that the hydrophobicity is critical for embedding the carboxy terminus in the ER membrane. Then an enzymatic reaction replaces the carboxy terminus with the GPI anchor.

Within hPLAP, the GPI anchor is attached at an aspartate in the sequence, DAAH. Similarly hIAP, bIAP II, and bIAP IV also have this DAAH sequence conserved, potentially serving as the GPI anchor site. Mutational studies with hPLA indicate that preventing GPI anchoring results in intracellular retention. In addition, mutations around the anchor site or in the hydrophobic domain either 1) prevent anchor attachment leading to intracellular retention or 2) do not block anchor attachment. Without wishing to be bound by theory, it is believed that the hydrophobic domain serves as a signal for GPI anchor attachment. Truncating or eliminating the hydrophobic domain leads to secretion. Finally, there is a single mutation in the hydrophobic domain that, in hPLAP, enables secretion of a protein with its hydrophobic domain intact.

In various embodiments, the AP-based agent of the invention is GPI anchored to a host cell. For example, the AP-based agent may be GPI anchored to the cell membrane of the host cell. In other embodiments, the AP-based agent of the invention is a secreted rather than an anchored protein. In some embodiments, the AP-based agent is not GPI anchored. In some embodiments, the AP-based agent may lack the GPI anchor site. In some embodiments, the AP-based agent comprises a stop codon that is inserted immediately after the GPI anchor site. In an embodiment, the AP-based agent comprises a stop codon after the aspartate in the DAAH consensus site (e.g., at amino acid 503 of hIAP and bIAP IV or amino acid 506 of bIAP II).

```
HIAP with stop codon
                                                           (SEQ ID NO: 4)
  1 mqgpwvllll glrlqlslgv ipaeeenpaf wnrqaaeald aakklqpiqk vaknlilflg 61 dglgvptvta trilkgqkng klgpetplam drfpylalsk tynvdrqvpd saatataylc 121 gvkanfqtig lsaaarfnqc nttrgnevis vmnrakqagk svgvvtttrv qhaspagtya 181 htvnrnwysd admpasarqe gcgdiatqli snmdidvilg ggrkymfpmg tpdpeypada 241 sqngirldgk nlvqewlakh qgawyvwnrt elmgasldqs vthlmglfep gdtkyeihrd
```

-continued

```
301 ptldpslmem teaalrllsr nprgfylfve ggridhghhe gvayqaltea vmfddaiera 361 gqltseedtl tlvtadhshv fsfggytlrg ssifglapsk aqdskaytsi lygngpgyvf 421 nsgvrpdvne sesgspdygq qaavplsset hggedvavfa rgpqahlvhg vqeqsfvahv 481 mafaaclepy tacdlappag ttd
```

BIAP II with stop codon
(SEQ ID NO: 5)

```
  1 mqgacvllll glhlqlslgl ipaeeenpaf wnrgaagald vakklqpiqt aaknvilflg 61 dgmgvptvta trilkgqmng klgpetplam dqfpyvalsk tynvdrqvpd sagtataylc 121 gvkgnyrtig vsaaarynqc nttrgnevts vinrakkagk avgvvtttrv qhaspagaya 181 htvnrnwysd adlpadaqkn gcgdiaaglv ynmdidvilg ggrmymfpeg tpdpeypdda 241 svngvrkdkq nlvqewqakh qgagyvwnrt allqaaddss vthlmglfep admkynvqqd 301 htkdptlaem teaalqvlsr nprgfylfve ggridhghhd gkaymaltea imfdnaiaka 361 neltseldtl ilvtadhshv fsfggytlrg tsifglapgk aldsksytsi lygngpgyal 421 gggsrpdvng stseepsyrq qaavplaset hggedvavfa rgpqahlvhg vqeetfvahi 481 mafagcvepy tdcnlpapat atsipd
```

BIAP IV with stop codon
(SEQ ID NO: 6)

```
  1 mgwacvllll glwlqlsltf ipaeeedpaf wnrgaagald vakklqpiqt aaknvilflg 61 dgmgvptvta trilkgqmng klgpetplam dqfpyvalsk tynvdrqvpd sagtataylc 121 gvkgnyktig vsaaarynqc nttsgnevts vmnrakkagk svgvvttsrv qhaspagaya 181 htvnrnwysd adlpadaqty gcqdiatqlv nnmdidvilg ggrmymfpeg tpdpeypydv 241 nqtgvrkdkr nlvqewqakh qgagyvwnrt ellqaandps vthlmglfep admkynvqqd 301 ptkdptleem teaalqvlsr npqgfylfve ggridhghhe gkaymaltdt vmfdnaiaka 361 neltseldtl ilatadhshv fsfggytlrg tsifglapsk asdnksytsi lygngpgyvl 421 ggglrpdvnd sisedpsyrq qaavplsses hggedvavfa rgpqahlvhg vqeetfvahv 481 mafagcvepy tdcnlpapsg lsd
```

In an embodiment, the AP-based agent is bIAP IV and includes a stop codon after amino acid 508 to mimic a secreted PLAP construct as depicted below:

BIAP IV with stop codon after amino acid 508
(SEQ ID NO: 7)

```
  1 mgwacvllll glwlqlsltf ipaeeedpaf wnrgaagald vakklqpiqt aaknvilflg 61 dgmgvptvta trilkgqmng klgpetplam dqfpyvalsk tynvdrqvpd sagtataylc 121 gvkgnyktig vsaaarynqc nttsgnevts vmnrakkagk svgvvttsrv qhaspagaya 181 htvnrnwysd adlpadaqty gcqdiatqlv nnmdidvilg ggrmymfpeg tpdpeypydv 241 nqtgvrkdkr nlvqewqakh qgagyvwnrt ellqaandps vthlmglfep admkynvqqd 301 ptkdptleem teaalqvlsr npqgfylfve ggridhghhe gkaymaltdt vmfdnaiaka 361 neltseldtl ilatadhshv fsfggytlrg tsifglapsk asdnksytsi lygngpgyvl 421 ggglrpdvnd sisedpsyrq qaavplsses hggedvavfa rgpqahlvhg vqeetfvahv 481 mafagcvepy tdcnlpapsg lsdaahla
```

In various embodiments, the AP-based agent of the invention is a fusion protein. In some embodiments, the AP-based agent comprises an alkaline phosphatase fused to a protein domain that replaces the GPI anchor sequence. In some embodiments, the alkaline phosphatase is fused to a protein domain that promotes protein folding and/or protein purification and/or protein dimerization and/or protein stability. In various embodiments, the AP-based agent fusion protein has an extended serum half-life.

In an embodiment, the alkaline phosphatase is fused to an immunoglobulin Fc domain and/or hinge region. In various embodiments, the immunoglobulin Fc domain and/or hinge region is derived from the Fc domain and/or hinge region of an antibody (e.g., of IgG, IgA, IgD, and IgE, inclusive of subclasses (e.g. IgG1, IgG2, IgG3, and IgG4, and IgA1 and IgA2)). In an embodiment, the AP-based agent of the invention comprises an alkaline phosphatase fused to the hinge region and/or Fc domain of IgG.

In various embodiments, the AP-based agent is fused to a Fc domain of IgG comprising one or more mutations. In some embodiments, the one or more mutations in the Fc domain of IgG function to increase serum half-life and longevity. In some embodiments, the Fc domain of IgG comprises one or more mutations at amino acid residues 251-256, 285-290, 308-314, 385-389 and 428-436, numbered according to the EU index as in Kabat (see Kabat et al., (1991) Sequences of Proteins of Immunological Interest, U.S. Public Health Service, National Institutes of Health, Washington, DC). In some embodiments, at least one of the amino acid substitutions is at amino acid residue 252, 254, 256, 309, 311, 433 or 434. In an embodiment, the amino acid substitution at amino acid residue 252 is a substitution with tyrosine, phenylalanine, tryptophan or threonine. In an embodiment, the amino acid substitution at amino acid residue 254 is a substitution with threonine. In an embodiment, the amino acid substitution at amino acid residue 256 is a substitution with serine, arginine, glutamine, glutamic acid, aspartic acid, or threonine. In an embodiment, the amino acid substitution at amino acid residue 309 is a substitution with proline. In an embodiment, the amino acid substitution at amino acid residue 311 is a substitution with serine. In an embodiment, the amino acid substitution at amino acid residue 385 is a substitution with arginine, aspartic acid, serine, threonine, histidine, lysine, alanine or glycine. In an embodiment, the amino acid substitution at amino acid residue 386 is a substitution with threonine, proline, aspartic acid, serine, lysine, arginine, isoleucine, or methionine. In an embodiment, the amino acid substitution at amino acid residue 387 is a substitution with arginine, proline, histidine, serine, threonine, or alanine. In an embodiment, the amino acid substitution at amino acid residue 389 is a substitution with proline, serine or asparagine. In an embodiment, the amino acid substitution at amino acid residue 433 is a substitution with arginine, serine, isoleucine, proline, or glutamine. In an embodiment, the amino acid substitution at amino acid residue 434 is a substitution with histidine, phenylalanine, or tyrosine.

In some embodiments, the Fc domain of IgG comprises one or more mutations at amino acid residue 252, 254, 256, 433, 434, or 436. In an embodiment, the Fc domain of IgG includes a triple M252Y/S254T/T256E mutation or YTE mutation. In another embodiment, the Fc domain of IgG includes a triple H433K/N434F/Y436H mutation or KFH mutation. In a further embodiment, the Fc domain of IgG includes a YTE and KFH mutation in combination.

In some embodiments, the Fc domain of IgG contains one or more mutations at amino acid residues 250, 253, 307, 310, 380, 428, 433, 434, and 435. Exemplary mutations include T250Q, M428L, T307A, E380A,I253A, H310A, M428L, H433K, N434A, N434F, N434S, and H435A. In an embodiment, the Fc domain of IgG comprises a M428L/N434S mutation or LS mutation. In another embodiment, the Fc domain of IgG comprises a T250Q/M428L mutation or QL mutation. In another embodiment, the Fc domain of IgG comprises an N434A mutation. In another embodiment, the Fc domain of IgG comprises a T307A/E380A/N434A mutation or AAA mutation. In another embodiment, the Fc domain of IgG comprises an I253A/H310A/H435A mutation or IHH mutation. In another embodiment, the Fc domain of IgG comprises a H433K/N434F mutation. In another embodiment, the Fc domain of IgG region comprises a M252Y/S254T/T256E and a H433K/N434F mutation in combination.

Exemplary mutations in the Fc domain of IgG are described, for example, in Robbie, et al., Antimicrobial Agents and Chemotherapy (2013), 57(12):6147-6153, Dall'Acqua et al, JBC (2006), 281(33):23514-24, Dall'Acqua et al, Journal of Immunology (2002), 169:5171-80, Ko et al. Nature (2014) 514:642-645, Grevys et al Journal of Immunology. (2015), 194(11):5497-508, and U.S. Pat. No. 7,083,784, the entire contents of which are hereby incorporated by reference.

In various embodiments, the one or more mutations in the Fc domain of IgG increases affinity for the neonatal Fc receptor (FcRn). In some embodiments, the one or more mutations in the Fc domain of IgG increases affinity for FcRn at a pH of about 6.0, about 6.1, about 6.2, about 6.3, about 6.4, or about 6.5.

In various embodiments, the alkaline phosphatase is fused to one or more of PEG, XTENylation (e.g., as rPEG), polysialic acid (POLYXEN), albumin, elastin-like protein, elastin like protein (ELP), PAS, HAP, GLK, CTP, and transferrin. In various embodiments, the alkaline phosphatase is fused to one or more of the agents described in BioDrugs (2015) 29:215-239, the entire contents of which are hereby incorporated by reference.

In an embodiment, the alkaline phosphatase is fused to a protein domain (e.g., an immunoglobulin Fc domain) via a linker to the GPI anchor site. For example, the alkaline phosphatase may be fused to a protein domain via the aspartate at the GPI anchor sequence. The invention contemplates the use of a variety of linker sequences. In various embodiments, the linker may be derived from naturally-occurring multi-domain proteins or are empirical linkers as described, for example, in Chichili et al, (2013), Protein Sci. 22(2):153-167, Chen et al, (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present AP-based agent. In another example, the linker may function to target the AP-based agent to a particular cell type or location.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). In an embodiment, the linker sequence is GGSGGSGGGGSGGGGS. Additional illustrative linkers include, but are not limited to, linkers having the sequence LE, GGGGS, (GGGGS)$_n$ (n=1-4), (Gly)$_8$, (Gly)$_6$, (EAAAK)$_n$ (n=1-3), A(EAAAK)$_n$A (n=2-5), AEAAAKEAAAKA, A(EAAAK)$_4$ALEA(EAAAK)$_4$A, PAPAP, KESGSVSSEQLAQFRSLD, EGKSSGSGS-ESKST, GSAGSAAGSGEF, and (XP)$_n$, with X designating any amino acid, e.g., Ala, Lys, or Glu. In various embodiments, the linker is GGS.

In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

According to crystallographic studies, the immunoglobulin hinge region can be further subdivided functionally into three regions: the upper hinge region, the core region, and the lower hinge region. See Shin et al., 1992 *Immunological Reviews* 130:87. The upper hinge region includes amino acids from the carboxyl end of $C_{H1}$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. The core hinge region of wild-type human IgG1 contains the sequence Cys-Pro-Pro-Cys which, when dimerized by disulfide bond formation, results in a cyclic octapeptide believed to act as a pivot, thus conferring flexibility. In various embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In various embodiments, the linker of the present invention comprises one or more glycosylation sites.

In some embodiments, the linker is a synthetic linker such as PEG.

Illustrative Fc fusion constructs of the invention include:

```
BIAP II with Fc Fusion (SEQ ID NO: 8) - Fc domain is underlined
  1 mqgacvllll glhlqlslgl ipaeeenpaf wnrgaagald vakklqpiqt aaknvilflg 61 dgmgvptvta trilkgqmng klgpetplam dqfpyvalsk tynvdrqvpd sagtataylc 121 gvkgnyrtig vsaaarynqc nttrgnevts vinrakkagk avgvvtttrv qhaspagaya 181 htvnrnwysd adlpadaqkn gcgdiaaglv ynmdidvilg ggrmymfpeg tpdpeypdda 241 svngvrkdkq nlvqewqakh qgagyvwnrt allqaaddss vthlmglfep admkynvqqd 301 htkdptlaem teaalqvlsr nprgfylfve ggridhghhd gkaymaltea imfdnaiaka 361 neltseldtl ilvtadhshv fsfggytlrg tsifglapgk aldsksytsi lygngpgyal 421 gggsrpdvng stseepsyrq qaavplaset hggedvavfa rgpqahlvhg vqeetfvahi 481 mafagcvepy tdcnlpapat atsipdGGSGGSGGGGSGGGGSEPKSCDKTHTCPPCPAPE

LLGGPSVFLFPPKPKDTLMI SRTPEVICVVVDVSHEDPQV KFNWYVDGVQVHNAKTKPRE

QQYNSTYRVVSVLTVLHQNW LDGKEYKCKVSNKALPAPIE KTISKAKGQPREPQVYTLPP

SREEMTKNQVSLTCLVKGFY PSDIAVEWESNGQPENNYKT TPPVLDSDGSFFLYSKLTVD

KSRWQQGNVFSCSVMHEALH NHYTQKSLSLSPGK
```

-continued

BIAP IV with Fc Fusion (SEQ ID NO: 9) - Fc domain is underlined
```
  1 mgwacvllll glwlqlsltf ipaeeedpaf wnrgaagald vakklqpiqt aaknvilflg
 61 dgmgvptvta trilkgqmng klgpetplam dqfpyvalsk tynvdrqvpd sagtataylc
121 gvkgnyktig vsaaarynqc nttsgnevts vmnrakkagk svgvvttsrv qhaspagaya
181 htvnrnwysd adlpadaqty gcqdiatqlv nnmdidvilg ggrmymfpeg tpdpeypydv
241 nqtgvrkdkr nlvqewqakh qgagyvwnrt ellqaandps vthlmglfep admkynvqqd
301 ptkdptleem teaalqvlsr npqgfylfve ggridhghhe gkaymaltdt vmfdnaiaka
361 neltseldtl ilatadhshv fsfggytlrg tsifglapsk asdnksytsi lygngpgyvl
421 ggglrpdvnd sisedpsyrq qaavplsses hggedvavfa rgpqahlvhg vqeetfvahv
481 mafagcvepy tdcnlpapsg lsdGGSGGSGGGGSGGGGSEPKSCDKTHTCPPCPAPE
    LLGGPSVFLFPPKPKDTLMI SRTPEVICVVVDVSHEDPQV KFNWYVDGVQVHNAKTKPRE
    QQYNSTYRVVSVLTVLHQNW LDGKEYKCKVSNKALPAPIE KTISKAKGQPREPQVYTLPP
    SREEMTKNQVSLTCLVKGFY PSDIAVEWESNGQPENNYKT TPPVLDSDGSFFLYSKLTVD
    KSRWQQGNVFSCSVMHEALH NHYTQKSLSLSPGK
```

HIAP with Fc Fusion (SEQ ID NO: 18) - Fc domain is underlined
```
  1 mqgpwvllll glrlqlslgv ipaeeenpaf wnraaeeald aakklqpiqk vaknlilflg
 61 dglgvptvta trilkgqkng klgpetplam drfpylalsk tynvdrqvpd saatataylc
121 gvkanfqtig lsaaarfnqc nttrgnevis vmnrakqagk svgvvtttrv qhaspagtya
181 htvnrnwysd admpasarqe gcgdiatqli snmdidvilg ggrkymfpmg tpdpeypada
241 sqngirldgk nlvqewlakh qgawyvwnrt elmgasIdqs vthlmglfep gdtkyeihrd
301 ptldpslmem teaalrlIsr nprgfylfve ggridhghhe gvayqaltea vmfddaiera
361 gqltseedtl tivtadhshv fsfggytlrg ssifglapsk aqdskaytsi lygngpgyvf
421 nsgvrpdvne sesgspdygq qaavplsset hggedvavfa rgpqahlvhg vqeqsfvahv
481 mafaaclepy tacdlappac ttdaahpvaa slpllagtll llgasaap
    GGSGGSGGGGSGGGGSEPKSCDKTHTCPPCPAPE LLGGPSVFLFPPKPKDTLMI
    SRTPEVICVVVDVSHEDPQV KFNWYVDGVQVHNAKTKPRE QQYNSTYRVVSVLTVLHQNW
    LDGKEYKCKVSNKALPAPIE KTISKAKGQPREPQVYTLPP SREEMTKNQVSLTCLVKGFY
    PSDIAVEWESNGQPENNYKT TPPVLDSDGSFFLYSKLTVD KSRWQQGNVFSCSVMHEALH
    NHYTQKSLSLSPGK
```

In various embodiments, the linker can be substituted with any other linker disclosed herein.

A Saccharomyces alkaline phosphatase, Pho8, is produced as an inactive pro-enzyme. It is not GPI anchored, but is a transmembrane protein with its amino terminus extending out of a lysosome into the cytoplasm. Within the lysosome, an enzyme, PEP4, cleaves the carboxy terminus to activate the enzyme. Without wishing to be bound by theory, it is believed that mammalian alkaline phosphatases may also be generated as inactive pro-enzymes. This is because alkaline phosphatases can dephosphorylate ATP, so that activity in the ER could drain the ER of its major energy source. Without wishing to be bound by theory, it is believed that the inhibitory function is located to the carboxy terminus that would be relieved upon GPI anchor addition. Alternatively, other activities such as folding or metal (Zn or Mg) inclusion could control activity.

In various embodiments, the AP-based agent of the invention is a pro-enzyme. In an embodiment, the activity of the proenzyme is suppressed by a carboxy terminus. In an embodiment, protease removal of the carboxy terminus reactivates the enzymatic activity of the alkaline phosphatase. In an embodiment, the pro-enzyme is more efficiently secreted than the enzyme without the carboxy terminus.

In some embodiments, for generation of the pro-enzyme, the native carboxy terminus of the alkaline phosphatase is replaced with the analogous sequence from hPLAP. In some embodiments, a mutation is made in the hydrophobic carboxy tail to promote protein secretion without cleavage of the carboxy terminus. In an illustrative embodiment, a single point mutation such as a substitution of leucine with e.g., arginine is generated in the hydrophobic carboxy terminus (e.g. allpllagtl is changed to e.g., allplragtl) to result in secretion of the enzyme without removal of the carboxy terminus.

In an embodiment, the AP-based agent is altered to include a specific enzyme cleavage site which allows subsequent removal of the carboxy terminus. In an embodiment, the AP-based agent includes a protease cleavage site. Illustrative protease cleavage sites include, but are not limited to, cleavage sites recognized by furin, Rhinovirus 16 3C protease, factor Xa protease, trpysin, chymotrypsin, elastase, pepsin, papain subtilisin, thermolysin, V-8 protease, submaxillaris protease, clostripain, thrombin, collagenase, and any other endoproteases. In an alternative embodiment, the AP-based agent includes a cleavage site recognized by a digestive enzyme present in the GI tract. In such embodiments, the AP-based agent may be administered as a prodrug that is subsequently activated in the GI tract.

In an illustrative embodiment, the proenzyme is a proenzyme of bIAP IV having the following sequences:

```
BIAP IV with the hPLAP Carboxy Terminus and Mutation for
Unprocessed Secretion and RV3C Cleavage (at . . . LEVLFQGP . . . ):
                                                        SEQ ID NO: 10
    1 mgwacvllll glwlqlsltf ipaeeedpaf wnrgaagald vakklqpiqt aaknvilflg 61 dgmgvptvta trilkgqmng klgpetplam dqfpyvalsk tynvdrqvpd sagtataylc 121 gvkgnyktig vsaaarynqc nttsgnevts vmnrakkagk svgvvttsrv qhaspagaya 181 htvnrnwysd adlpadaqty gcqdiatqlv nnmdidvilg ggrmymfpeg tpdpeypydv 241 nqtgvrkdkr nlvqewqakh qgagyvwnrt ellqaandps vthlmglfep admkynvqqd 301 ptkdptleem teaalqvlsr npqgfylfve ggridhghhe gkaymaltdt vmfdnaiaka 361 neltseldtl ilatadhshv fsfggytlrg tsifglapsk asdnksytsi lygngpgyvl 421 ggglrpdvnd sisedpsyrq qaavplsses hggedvavfa rgpqahlvhg vqeetfvahv 481 mafagcvepy tdcnlevlfq gpappagttd aahpgrsvvp allplragtl llletatap BIAP IV with hPLAP Carboxy Terminus and Mutation for Unprocessed
Secretion and FXa Cleavage (at . . . IEGR . . . ):
                                                        SEQ ID NO: 11
    1 mgwacvllll glwlqlsltf ipaeeedpaf wnrgaagald vakklqpiqt aaknvilflg 61 dgmgvptvta trilkgqmng klgpetplam dqfpyvalsk tynvdrqvpd sagtataylc 121 gvkgnyktig vsaaarynqc nttsgnevts vmnrakkagk svgvvttsrv qhaspagaya 181 htvnrnwysd adlpadaqty gcqdiatqlv nnmdidvilg ggrmymfpeg tpdpeypydv 241 nqtgvrkdkr nlvqewqakh qgagyvwnrt ellqaandps vthlmglfep admkynvqqd 301 ptkdptleem teaalqvlsr npqgfylfve ggridhghhe gkaymaltdt vmfdnaiaka 361 neltseldtl ilatadhshv fsfggytlrg tsifglapsk asdnksytsi lygngpgyvl 421 ggglrpdvnd sisedpsyrq qaavplsses hggedvavfa rgpqahlvhg vqeetfvahv 481 mafagcvepy tdcnlappag ttdaahpgieg rsvvpallpl ragtllllet atap
```

In various embodiments, the AP-based agent of the invention is efficiently expressed and secreted from a host cell. In an embodiment, the AP-based agent of the invention is efficiently transcribed in the host cell. In another embodiment, the AP-based agent exhibits enhanced RNA stability and/or transport in the host cell. In another embodiment, the AP-based agent is efficiently translated in the host cell. In a further embodiment, the AP-based agent is efficiently folded and/or transits efficiently through the ER, pre-golgi, and golgi. In another embodiment, the AP-based agent exhibits enhanced protein stability.

In various embodiments, the AP-based agent of the invention is GPI anchored to the cell membrane of a host cell. In other embodiments, the AP-based agent is secreted from the host cell. In such embodiments, the AP-based agent may include a protease cleavage site just upstream from the GPI anchor site. Illustrative protease cleavage sites are described previously. In an embodiment, the protease cleavage site is a furin cleavage site. In another embodiment, the AP-based agent may include a cleavage site recognized by a digestive enzyme in the GI tract just upstream from the GPI anchor site. In these embodiments, the AP-based agent is anchored in the ER and released in the late golgi and secreted.

In various embodiments, the AP-based agents are efficiently expressed in a host cell. In an embodiment, the Kozak sequence of the DNA construct encoding the AP-based agent is optimized. The Kozak sequence is the nucleotide sequence flanking the ATG start codon that instructs the ribosome to start translation. There is flexibility in the design of a Kozak sequence, but one canonical sequence is GCCGCCACCATGG. The purine in the −3 position and the G in the +4 position are the most important bases for translation initiation. For hIAP, bIAP II, and bIAP IV, the second amino acid, that is, the one after the initiator methionine, is glutamine. Codons for glutamine all have a C in the first position. Thus, their Kozak sequences all have an ATGC sequence. Accordingly, in various embodiments, the ATGC sequence is changed to ATGG. This can be achieved by changing the second amino acid to a glycine, alanine, valine, aspartate, or glutamic acid, all of whose codons have a G in the first position. These amino acids may be compatible with signal peptide function. In alternative embodiments, the entire signal peptide is substituted for peptide having a canonical Kozak sequence and is derived from a highly expressed protein such as an immunoglobulin.

In various embodiments, the signal peptide of the AP-based agent may be deleted and/or substituted. For example, the signal peptide may be deleted, mutated, and/or substituted (e.g., with another signal peptide) to ensure optimal protein expression.

In some embodiments, The DNA construct encoding the AP-based agent of the invention comprises untranslated DNA sequences. Such sequences include an intron, which may be heterologous to the IAP protein or native to the IAP protein including the native first and/or second intron and/or a native 3' UTR. Without wishing to be bound by theory, it is believed that include of these sequences enhance protein expression by stabilizing the mRNA. Accordingly, in various embodiments, the DNA construct encoding the AP-based agent of the invention comprises the 5'UTR and/or the 3'UTR.

Provided below are illustrative IAP DNA sequences with a first intron and a 3'UTR:

```
hIAP with native first intron (shown as bolded and
underlined)
                                       SEQ ID NO: 12
ATGCAGGGGCCCTGGGTGCTGCTGCTGCTGGGCCTGAGGCTACAGCTCTC

CCTGGGCGTCATCCCAGGTAATGAGGCTCCCCAAGCTGTTCCACACACAG

GGCACCCCCTCAGCCAGGCTGACCTGATCTCTACTCTCCCCCTGGCCAGC

TGAGGAGGAGAACCCGGCCTTCTGGAACCGCCAGGCAGCTGAGGCCCTGG

ATGCTGCCAAGAAGCTGCAGCCCATCCAGAAGGTCGCCAAGAACCTCATC

CTCTTCCTGGGCGATGGGTTGGGGGTGCCCACGGTGACAGCCACCAGGAT

CCTAAAGGGGCAGAAGAATGGCAAACTGGGGCCTGAGACGCCCCTGGCCA

TGGACCGCTTCCCATACCTGGCTCTGTCCAAGACATACAATGTGGACAGA

CAGGTGCCAGACAGCGCAGCCACAGCCACGGCCTACCTGTGCGGGGTCAA

GGCCAACTTCCAGACCATCGGCTTGAGTGCAGCCGCCCGCTTTAACCAGT

GCAACACGACACGCGGCAATGAGGTCATCTCCGTGATGAACCGGGCCAAG

CAAGCAGGAAAGTCAGTAGGAGTGGTGACCACCACACGGGTGCAGCACGC

CTCGCCAGCCGGCACCTACGCACACACAGTGAACCGCAACTGGTACTCAG

ATGCTGACATGCCTGCCTCAGCCCGCCAGGAGGGTGCCAGGACATCGCC

ACTCAGCTCATCTCCAACATGGACATTGACGTGATCCTTGGCGGAGGCCG

CAAGTACATGTTTCCCATGGGGACCCCAGACCCTGAGTACCCAGCTGATG

CCAGCCAGAATGGAATCAGGCTGGACGGGAAGAACCTGGTGCAGGAATGG

CTGGCAAAGCACCAGGGTGCCTGGTATGTGTGGAACCGCACTGAGCTCAT

GCAGGCGTCCCTGGACCAGTCTGTGACCCATCTCATGGGCCTCTTTGAGC

CCGGAGACACGAAATATGAGATCCACCGAGACCCCACACTGGACCCCTCC

CTGATGGAGATGACAGAGGCTGCCCTGCGCCTGCTGAGCAGGAACCCCCG

CGGCTTCTACCTCTTTGTGGAGGGCGGCCGCATCGACCATGGTCATCATG

AGGGTGTGGCTTACCAGGCACTCACTGAGGCGGTCATGTTCGACGACGCC

ATTGAGAGGGCGGGCCAGCTCACCAGCGAGGAGGACACGCTGACCCTCGT

CACCGCTGACCACTCCCATGTCTTCTCCTTTGGTGGCTACACCTTGCGAG

GGAGCTCCATCTTCGGGTTGGCCCCCAGCAAGGCTCAGGACAGCAAAGCC

TACACGTCCATCCTGTACGGCAATGGCCCGGGCTACGTGTTCAACTCAGG

CGTGCGACCAGACGTGAATGAGAGCGAGAGCGGGAGCCCCGATTACCAGC

AGCAGGCGGCGGTGCCCCTGTCGTCCGAGACCCACGGAGGCGAAGACGTG

GCGGTGTTTGCGCGCGGCCCGCAGGCGCACCTGGTGCATGGTGTGCAGGA

GCAGAGCTTCGTAGCGCATGTCATGGCCTTCGCTGCCTGTCTGGAGCCCT

ACACGGCCTGCGACCTGGCGCCTCCCGCCTGCACCACCGACGCCGCGCAC

CCAGTTGCCGCGTCGCTGCCACTGCTGGCCGGGACCCTGCTGCTGCTGGG

GGCGTCCGCTGCTCCCTGA hIAP with native 3'UTR (shown as bolded and
underlined)
                                       SEQ ID NO: 13
ATGCAGGGGCCCTGGGTGCTGCTGCTGCTGGGCCTGAGGCTACAGCTCTC

CCTGGGCGTCATCCCAGCTGAGGAGGAGAACCCGGCCTTCTGGAACCGCC

AGGCAGCTGAGGCCCTGGATGCTGCCAAGAAGCTGCAGCCCATCCAGAAG

GTCGCCAAGAACCTCATCCTCTTCCTGGGCGATGGGTTGGGGGTGCCCAC

GGTGACAGCCACCAGGATCCTAAAGGGGCAGAAGAATGGCAAACTGGGGC

CTGAGACGCCCCTGGCCATGGACCGCTTCCCATACCTGGCTCTGTCCAAG

ACATACAATGTGGACAGACAGGTGCCAGACAGCGCAGCCACAGCCACGGC

CTACCTGTGCGGGGTCAAGGCCAACTTCCAGACCATCGGCTTGAGTGCAG

CCGCCCGCTTTAACCAGTGCAACACGACACGCGGCAATGAGGTCATCTCC

GTGATGAACCGGGCCAAGCAAGCAGGAAAGTCAGTAGGAGTGGTGACCAC

CACACGGGTGCAGCACGCCTCGCCAGCCGGCACCTACGCACACACAGTGA

ACCGCAACTGGTACTCAGATGCTGACATGCCTGCCTCAGCCCGCCAGGAG

GGGTGCCAGGACATCGCCACTCAGCTCATCTCCAACATGGACATTGACGT

GATCCTTGGCGGAGGCCGCAAGTACATGTTTCCCATGGGGACCCCAGACC

CTGAGTACCCAGCTGATGCCAGCCAGAATGGAATCAGGCTGGACGGGAAG

AACCTGGTGCAGGAATGGCTGGCAAAGCACCAGGGTGCCTGGTATGTGTG

GAACCGCACTGAGCTCATGCAGGCGTCCCTGGACCAGTCTGTGACCCATC

TCATGGGCCTCTTTGAGCCCGGAGACACGAAATATGAGATCCACCGAGAC

CCCACACTGGACCCCTCCCTGATGGAGATGACAGAGGCTGCCCTGCGCCT

GCTGAGCAGGAACCCCCGCGGCTTCTACCTCTTTGTGGAGGGCGGCCGCA

TCGACCATGGTCATCATGAGGGTGTGGCTTACCAGGCACTCACTGAGGCG

GTCATGTTCGACGACGCCATTGAGAGGGCGGGCCAGCTCACCAGCGAGGA

GGACACGCTGACCCTCGTCACCGCTGACCACTCCCATGTCTTCTCCTTTG

GTGGCTACACCTTGCGAGGGAGCTCCATCTTCGGGTTGGCCCCCAGCAAG

GCTCAGGACAGCAAAGCCTACACGTCCATCCTGTACGGCAATGGCCCGGG

CTACGTGTTCAACTCAGGCGTGCGACCAGACGTGAATGAGAGCGAGAGCG

GGAGCCCCGATTACCAGCAGCAGGCGGCGGTGCCCCTGTCGTCCGAGACC

CACGGAGGCGAAGACGTGGCGGTGTTTGCGCGCGGCCCGCAGGCGCACCT

GGTGCATGGTGTGCAGGAGCAGAGCTTCGTAGCGCATGTCATGGCCTTCG

CTGCCTGTCTGGAGCCCTACACGGCCTGCGACCTGGCGCCTCCCGCCTGC

ACCACCGACGCCGCGCACCCAGTTGCCGCGTCGCTGCCACTGCTGGCCGG

GACCCTGCTGCTGCTGGGGGCGTCCGCTGCTCCCTGATTTACTAAAACCT

TGAAATAAAATTGTAAAACATCAGTTTGAAGGCCTGACTCTCAGGGTAGT

TCTTTTTTAATTCTGGGTTTT
``` bIAP IV with the first intron from bIAP I (shown
as bolded and underlined)
SEQ ID NO: 14
ATGCAGTGGGCCTGTGTGCTGCTGCTGCTGGGCCTGTGGCTACAGCTCTC

CCTCACCTTCATCCCAGGTAATCAGGCGGCTCCCAGCAGCCCCTACTCAC

AGGGGCGGCTCTAGGCTGACCTGACCAACACTCTCCCCTTGGGCAGCTGA

GGAGGAAGACCCCGCCTTCTGGAACCGCCAGGCAGCCCAGGCCCTTGATG

TAGCCAAGAAGTTGCAGCCGATCCAGACAGCTGCCAAGAATGTCATCCTC

TTCTTGGGGGATGGATGGGGGTGCCTACGGTGACAGCCACTCGGATCCT

AAAGGGGCAGATGAATGGTAAGCTGGGACCTGAGACACCCCTGGCCATGG

ACCAGTTCCCATACGTGGCTCTGTCCAAGACATACAACGTGGACAGACAG

GTGCCAGACAGCGCAGGCACTGCCACTGCCTACCTGTGTGGGGTCAAGGG

CAACTACAAAACCATTGGTGTAAGTGCAGCCGCCCGCTACAACCAGTGCA

ACACAACAAGTGGCAATGAGGTCACGTCTGTGATGAACCGGGCCAAGAAA

GCAGGAAAGTCAGTGGGAGTGGTGACCACCTCCAGGGTGCAGCATGCCTC

CCCAGCCGGTGCTTATGCACACACGGTGAACCGAAACTGGTACTCAGATG

CCGACCTGCCTGCCGATGCACAGACGTATGGCTGCCAGGACATCGCCACA

CAACTGGTCAACAACATGGATATTGACGTGATCCTGGGTGGAGGCCGAAT

GTACATGTTTCCTGAGGGGACCCCGGATCCTGAATACCCATACGATGTCA

ATCAGACTGGAGTCCGGAAGGACAAGCGGAATCTGGTGCAGGAGTGGCAG

GCCAAGCACCAGGGAGCCCAGTATGTGTGGAACCGCACGGAGCTCCTTCA

GGCAGCCAATGACCCCAGTGTAACACACCTCATGGGCCTCTTTGAGCCGG

CAGACATGAAGTATAATGTTCAGCAAGACCCCACCAAGGACCCGACCCTG

GAGGAGATGACGGAGGCGGCCCTGCAAGTGCTGAGCAGGAACCCCCAGGG

CTTCTACCTCTTCGTGGAGGGAGGCCGCATTGACCACGGTCACCATGAAG

GCAAAGCTTATATGGCACTGACTGATACAGTCATGTTTGACAATGCCATC

GCCAAGGCTAACGAGCTCACTAGCGAACTGGACACGCTGATCCTTGCCAC

TGCAGACCACTCCCATGTCTTCTCTTTTGGTGGCTACACACTGCGTGGGA

CCTCCATTTTCGGTCTGGCCCCAGCAAGGCCTCAGACAACAAGTCCTAC

ACCTCCATCCTCTATGGCAATGGCCCTGGCTACGTGCTTGGTGGGGCTT

AAGGCCCGATGTTAATGACAGCATAAGCGAGGACCCCTCGTACCGGCAGC

AGGCGGCCGTGCCCCTGTCTAGTGAGTCCCACGGGGCGAGGACGTGGCG

GTGTTCGCGCGAGGCCCGCAGGCGCACCTGGTGCACGGCGTGCAGGAGGA

GACCTTCGTGGCGCACGTCATGGCCTTTGCGGGCTGCGTGGAGCCCTACA

CCGACTGCAATCTGCCGGCCCCCTCTGGCCTCTCCGACGCCGCGCACCTG

GCGGCCAGCCCGCCTTCGCTGGCGCTGCTGGCCGGGGCGATGCTGCTGCT

GCTGGCGCCTGCCTTGTACTGA bIAP IV with the 3' UTR from bIAP I (shown
as bolded and underlined)
SEQ ID NO: 15
ATGCAGTGGGCCTGTGTGCTGCTGCTGCTGGGCCTGTGGCTACAGCTCTC

CCTCACCTTCATCCCAGCTGAGGAGGAAGACCCCGCCTTCTGGAACCGCC

AGGCAGCCCAGGCCCTTGATGTAGCCAAGAAGTTGCAGCCGATCCAGACA

GCTGCCAAGAATGTCATCCTCTTCTTGGGGGATGGGATGGGGGTGCCTAC

GGTGACAGCCACTCGGATCCTAAAGGGGCAGATGAATGGTAAGCTGGGAC

CTGAGACACCCCTGGCCATGGACCAGTTCCCATACGTGGCTCTGTCCAAG

ACATACAACGTGGACAGACAGGTGCCAGACAGCGCAGGCACTGCCACTGC

CTACCTGTGTGGGGTCAAGGGCAACTACAAAACCATTGGTGTAAGTGCAG

CCGCCCGCTACAACCAGTGCAACACAACAAGTGGCAATGAGGTCACGTCT

GTGATGAACCGGGCCAAGAAAGCAGGAAAGTCAGTGGGAGTGGTGACCAC

CTCCAGGGTGCAGCATGCCTCCCCAGCCGGTGCTTATGCACACACGGTGA

ACCGAAACTGGTACTCAGATGCCGACCTGCCTGCCGATGCACAGACGTAT

GGCTGCCAGGACATCGCCACACAACTGGTCAACAACATGGATATTGACGT

GATCCTGGGTGGAGGCCGAATGTACATGTTTCCTGAGGGGACCCCGGATC

CTGAATACCCATACGATGTCAATCAGACTGGAGTCCGGAAGGACAAGCGG

AATCTGGTGCAGGAGTGGCAGGCCAAGCACCAGGGAGCCCAGTATGTGTG

GAACCGCACGGAGCTCCTTCAGGCAGCCAATGACCCCAGTGTAACACACC

TCATGGGCCTCTTTGAGCCGGCAGACATGAAGTATAATGTTCAGCAAGAC

CCCACCAAGGACCCGACCCTGGAGGAGATGACGGAGGCGGCCCTGCAAGT

GCTGAGCAGGAACCCCCAGGGCTTCTACCTCTTCGTGGAGGGAGGCCGCA

TTGACCACGGTCACCATGAAGGCAAAGCTTATATGGCACTGACTGATACA

GTCATGTTTGACAATGCCATCGCCAAGGCTAACGAGCTCACTAGCGAACT

GGACACGCTGATCCTTGCCACTGCAGACCACTCCCATGTCTTCTCTTTTG

GTGGCTACACACTGCGTGGGACCTCCATTTTCGGTCTGGCCCCCAGCAAG

GCCTCAGACAACAAGTCCTACACCTCCATCCTCTATGGCAATGGCCCTGG

CTACGTGCTTGGTGGGGCTTAAGGCCCGATGTTAATGACAGCATAAGCG

AGGACCCCTCGTACCGGCAGCAGGCGGCCGTGCCCCTGTCTAGTGAGTCC

CACGGGGCGAGGACGTGGCGGTGTTCGCGCGAGGCCCGCAGGCGCACCT

GGTGCACGGCGTGCAGGAGGAGACCTTCGTGGCGCACGTCATGGCCTTTG

CGGGCTGCGTGGAGCCCTACACCGACTGCAATCTGCCGGCCCCCTCTGGC

CTCTCCGACGCCGCGCACCTGGCGGCCAGCCCGCCTTCGCTGGCGCTGCT

GGCCGGGGCGATGCTGCTGCTGCTGGCGCCTGCCTTGTACTGAGGGGACC

CGGGGGTGGGGACACAGGCCCCGCCCTCCCTGGGAGGCAGGAAGCAGCTC

TCAAATAAACTGTTCTAAGTATGATACAGGAGTGATACATGTGTGAAGAG

AAGCCCTTAGGTGGGGGCACAGAGTGTCTGGGTGAGGGGGGTCAGGGTCA

CATCAGGAGGTTAGGGAGGGGTTGATGAAGGGCTGACGTTGAGCAAAGAC

CAAAGGCAACTCAGAAGGACAGTGGTGCAGGACTGGGTGTGGTCAGCAGG

GGGACTGGTTGGGGGATCC

In various embodiments, the present invention contemplates the use of bacterial alkaline phosphatases. In some embodiments, the AP-based agent of the invention is derived from *Bacillus subtilis*. *Bacillus subtilis* is a Gram-positive bacterium found in soil and the gastrointestinal tract of humans. *Bacillus subtilis* secretes high levels of proteins into the environment and in the human GI tract that are properly folded. Without wishing to be bound by theory, it is believed that *Bacillus subtilis* secreted proteins in the GI tract may be resistant to degradation by common gastrointestinal proteases. *Bacillus subtilis* expresses at high levels an alkaline phosphatase multigene family. Among those isozymes, alkaline phosphatase IV is responsible for the majority of total alkaline phosphatase expression and activity in *B. subtilis*. In some embodiments, the AP-based agent of the invention is derived from *Bacillus licheniformis*. In some embodiments, the AP-based agent of the invention is derived from *Escherichia coli*.

Accordingly, in an illustrative embodiment, the AP-based agent of the invention is derived from alkaline phosphatase IV of *Bacillus subtilis*. In an embodiment, the bacterial alkaline phosphatase may have the following nucleotide and amino acid sequences:

```
Bacillus subtilis JH642 alkaline phosphatase IV,
mature protein nucleotide sequence
                                       SEQ ID NO: 16
AAAAAACAAGACAAAGCTGAGATCAGAAATGTCATTGTGATGATAGGCGA

CGGCATGGGGACGCCTTACATAAGAGCCTACCGTTCCATGAAAAATAACG

GTGACACACCGAATAACCCGAAGTTAACAGAATTTGACCGGAACCTGACA

GGCATGATGATGACGCATCCGGATGACCCTGACTATAATATTACAGATTC

AGCAGCAGCCGGAACAGCATTAGCGACAGGCGTTAAGACATATAACAATG

CAATTGGCGTCGATAAAAACGGAAAAAAAGTGAAATCTGTACTTGAAGAG

GCCAAACAGCAAGGCAAGTCAACAGGGCTTGTCGCCACGTCTGAAATTAA

CCACGCCACTCCAGCCGCATATGGCGCCCACAATGAATCACGGAAAAACA

TGGACCAAATCGCCAACAGCTATATGGATGACAAGATAAAAGGCAAACAT

AAAATAGACGTGCTGCTCGGCGGCGGAAAATCTTATTTTAACCGCAAGAA

CAGAAACTTGACAAAGGAATTCAAACAAGCCGGCTACAGCTATGTGACAA

CTAAACAAGCATTGAAAAAAATAAAGATCAGCAGGTGCTCGGGCTTTTC

GCAGATGGAGGGCTTGCTAAAGCGCTCGACCGTGACAGTAAAACACCGTC

TCTCAAAGACATGACGGTTTCAGCAATTGATCGCCTGAACCAAAATAAAA

AAGGATTTTCTTGATGGTCGAAGGGAGCCAGATTGACTGGGCGGCCCAT

GACAATGATACAGTAGGAGCCATGAGCGAGGTTAAAGATTTTGAACAGGC

CTATAAAGCCGCGATTGAATTTGCGAAAAAAGACAAACATACACTTGTGA

TTGCAACTGCTGACCATACAACCGGCGGCTTTACCATTGGCGCAAACGGG

GAAAAGAATTGGCACGCAGAACCGATTCTCTCCGCTAAGAAAACACCTGA

ATTCATGGCCAAAAAAATCAGTGAAGGCAAGCCGGTTAAAGATGTGCTCG

CCCGCTATGCCAATCTGAAAGTCACATCTGAAGAAATCAAAAGCGTTGAA

GCAGCTGCACAGGCTGACAAAAGCAAAGGGGCCTCCAAAGCCATCATCAA

GATTTTTAATACCCGCTCCAACAGCGGATGGACGAGTACCGATCATACCG

GCGAAGAAGTACCGGTATACGCGTACGGCCCCGGAAAAGAAAAATTCCGC

GGATTGATTAACAATACGGACCAGGCAAACATCATATTTAAGATTTTAAA

AACTGGAAAA

Bacillus subtilis JH642 alkaline phosphatase IV,
mature protein amino acid sequence
                                       SEQ ID NO: 17
KKQDKAEIRNVIVMIGDGMGTPYIRAYRSMKNNGDTPNNPKLTEFDRNLT

GMMMTHPDDPDYNITDSAAAGTALATGVKTYNNAIGVDKNGKKVKSVLEE

AKQQGKSTGLVATSEINHATPAAYGAHNESRKNMDQIANSYMDDKIKGKH
```

```
-continued

KIDVLLGGGKSYFNRKNRNLTKEFKQAGYSYVTTKQALKKNKDQQVLGLF

ADGGLAKALDRDSKTPSLKDMTVSAIDRLNQNKKGFFLMVEGSQIDWAAH

DNDTVGAMSEVKDFEQAYKAAIEFAKKDKHTLVIATADHTTGGFTIGANG

EKNWHAEPILSAKKTPEFMAKKISEGKPVKDVLARYANLKVTSEEIKSVE

AAAQADKSKGASKAIIKIFNTRSNSGWTSTDHTGEEVPVYAYGPGKEKFR

GLINNTDQANIIFKILKTGK
```

In some embodiments, the AP-based agent includes bacterial alkaline phosphatases that has one or more mutations that alter catalytic activity. In some embodiments, the bacterial alkaline phosphatases include one or more mutations such that their catalytic activity is similar or higher than mammalian alkaline phosphatases. In some embodiments, the bacterial alkaline phosphatases include one or more mutations that alter their de-phosphorylation profile. In an embodiment, the bacterial alkaline phosphatases of the invention exhibit similar de-phosphorylation profile as mammalian alkaline phosphatases. In some embodiments, the bacterial alkaline phosphatases include one or more mutations that alter their activity at higher pH. In an embodiment, the bacterial alkaline phosphatases of the invention exhibit similar activity at higher pH as mammalian alkaline phosphatases. In some embodiments, the bacterial alkaline phosphatases include one or more mutations that alter their metal requirements. In an embodiment, the bacterial alkaline phosphatases of the invention exhibits metal requirements (e.g., Mg) as mammalian alkaline phosphatases.

For example, in certain embodiments, the AP-based agent of the invention is derived from *Bacillus subtilis* JH642 alkaline phosphatase IV, and has one or more mutations at positions 101, 328, A330, and 374. For example, the AP-based agent may include one or more of the following mutations: D101A, W328H, A330N and G374C.

In various embodiments, the AP-based agent of the invention comprises a nucleotide sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the sequences disclosed herein.

In some embodiments, the AP-based agent of the invention comprises a amino sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the sequences disclosed herein.

In various embodiments, the AP-based agent of the invention may comprise an amino acid sequence having one or more amino acid mutations relative any of the protein sequences described herein. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as βmethyl amino acids, C α-methyl amino acids, N α-methyl amino acids, and amino acid analogs in general).

Mutations may also be made to the nucleotide sequences of the alkaline phosphatases by reference to the genetic code, including taking into account codon degeneracy. In various embodiments, the DNA construct encoding the AP-based agent is codon optimized for optimal protein expression in the host cell.

Mutations may be made to the AP-based agent of the invention to select for agents with desired characteristics. For examples, mutations may be made to generate AP-based agents with enhanced catalytic activity or protein stability. In various embodiments, directed evolution may be utilized to generate AP-based agents of the invention. For example, error-prone PCR and DNA shuffling may be used to identify mutations in the bacterial alkaline phosphatases that confer enhanced activity.

In various embodiments, the AP-based agent of the invention possesses desirable characteristics, including, for example, high specific activity. In various embodiments, the alkaline phosphatase of the invention possesses a specific activity of at least about 100 U/mg to about 20,000 U/mg. In various embodiments, the alkaline phosphatase of the invention possesses a specific activity of at least about 100 U/mg, about 200 U/mg, about 300 U/mg, about 400 U/mg, about 500 U/mg, about 600 U/mg, about 700 U/mg, about 800 U/mg, about 900 U/mg, about 1,000 U/mg, about 2,000 U/mg, about 3,000 U/mg, about 4,000 U/mg, about 5,000 U/mg, about 6,000 U/mg, about 7,000 U/mg, about 8,000 U/mg, about 9,000 U/mg, about 10,000 U/mg, about 11,000 U/mg, about 12,000 U/mg, about 13,000 U/mg, about 14,000 U/mg, about 15,000 U/mg, about 16,000 U/mg, about 17,000 U/mg, about 18,000 U/mg, about 19,000 U/mg, or about 20,000 U/mg.

In various embodiments, the AP-based agent of the invention is stable and/or active in the GI tract, e.g. in one or more of the mouth, esophagus, stomach, duodenum, small intestine, duodenum, jejunum, ileum, large intestine, colon transversum, colon descendens, colon ascendens, colon sigmoidenum, cecum, and rectum. In a specific embodiment, the alkaline phosphatase is stable in the large intestine, optionally selected from one or more of colon transversum, colon descendens, colon ascendens, colon sigmoidenum and cecum. In a specific embodiment, the alkaline phosphatase is stable in the small intestine, optionally selected from one or more of duodenum, jejunum, and ileum. In some embodiments, the alkaline phosphatase is resistant to proteases in the GI tract, including for example, the small intestine. In some embodiments, the alkaline phosphatase is substantially active at a pH of about 5.0 or above. For example, the alkaline phosphatase may be substantially active at a pH about 6.0 to about 12, e.g. about 6.0, or about 6.1, or about 6.2, or about 6.3, or about 6.4, or about 6.5, or about 6.6, or about 6.7, or about 6.8, or about 6.9, or about 7.0, or about 7.1, or about 7.2, or about 7.3, or about 7.4, or about 7.5, or about 8.0, or about 8.5, or about 9.0, or about 9.5, or about 10.0, or about 10.5, or about 11.0, or about 11.5, or about 12.0 (including, for example, via formulation, as described herein). In some embodiments, stable refers to an enzyme that has a long enough half-life and maintains sufficient activity for therapeutic effectiveness.

In various embodiments, the AP-based agent of the invention is stable in chyme.

In some embodiments, the AP-based agent described herein includes derivatives that are modified, i.e., by the covalent attachment of any type of molecule to the alkaline phosphatase such that covalent attachment does not prevent the activity of the enzyme. For example, but not by way of limitation, derivatives include alkaline phosphatases that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out, including, but not limited to specific chemical cleavage, acetylation, formylation, metabolic synthesis of tunicamycin, etc. Additionally, the derivative can contain one or more non-classical amino acids. In various embodiments, the AP-based agent is glycosylated to ensure proper protein folding.

In still other embodiments, the AP-based agents of the invention may be modified to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

The AP-based agent described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methyl benzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the alkaline phosphatases having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of a pharmaceutically acceptable salt.

Further, any AP-based agent described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, cellulose, hypromellose, lactose, sucrose, malt, rice, flour, chalk, silica gel, sodium stearate, glycerol monostearate, talc, sodium chloride, dried skim milk, glycerol, propylene, glycol, povidone, crosspovidone, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the AP-based agent and/or pharmaceutical compositions (and/or additional therapeutic agents) can include a solubilizing agent. Also, the agents can be delivered with a suitable vehicle or delivery device. Compositions for administration can optionally include a local anesthetic such as, for example, lignocaine to lessen pain at the site of the injection. Combination therapies outlined herein can be co-delivered in a single delivery vehicle or delivery device.

Formulations

The present invention provides the described AP-based agent and/or pharmaceutical compositions (and/or additional therapeutic agents) in various formulations. Any AP-based agent and/or pharmaceutical composition (and/or additional therapeutic agents) described herein can take the form of tablets, pills, pellets, capsules, capsules containing liquids, capsules containing multiparticulates, powders, solutions, emulsions, drops, suppositories, emulsions, aerosols, sprays, suspensions, delayed-release formulations, sustained-release formulations, controlled-release formulations, or any other form suitable for use.

The formulations comprising the AP-based agent and/or pharmaceutical compositions (and/or additional therapeutic agents) may conveniently be presented in unit dosage forms. For example, the dosage forms may be prepared by methods which include the step of bringing the therapeutic agents into association with a carrier, which constitutes one or more accessory ingredients. For example, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by press tableting)

In one embodiment, the AP-based agent (and/or additional therapeutic agents) described herein is formulated as a composition adapted for a mode of administration described herein In various embodiments, the administration the AP-based agent and/or pharmaceutical compositions (and/or additional therapeutic agents) is any one of oral, intravenous, and parenteral. For example, routes of administration include, but are not limited to, oral, intradermal, intramuscular, intraperitoneal, intravenous, subcutaneous, intranasal, epidural, sublingual, intranasal, intracerebral, intravaginal, transdermal, rectally, by inhalation, or topically (e.g., to the ears, nose, eyes, or skin).

In one embodiment, the AP-based agent and/or pharmaceutical compositions (and/or additional therapeutic agents) described herein is formulated as a composition adapted for oral administration. Compositions for oral delivery can be in the form of tablets, lozenges, aqueous or oily suspensions, granules, powders, sprinkles, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration to provide a sustained action over an extended period of time. Selectively permeable membranes surrounding an osmotically active agent driving any alkaline phosphatase (and/or additional therapeutic agents) described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, ethacrylic acid and derivative polymers thereof, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

In various embodiments, the AP-based agent and/or pharmaceutical compositions (and/or additional therapeutic agent) are formulated as solid dosage forms such as tablets, dispersible powders, granules, and capsules. In one embodiment, the AP-based agent and/or pharmaceutical compositions (and/or additional therapeutic agent) are formulated as a capsule. In another embodiment, the AP-based agent and/or pharmaceutical compositions (and/or additional therapeutic agent) are formulated as a tablet. In yet another embodiment, the AP-based agent and/or pharmaceutical compositions (and/or additional therapeutic agent) are formulated as a soft-gel capsule. In a further embodiment, the AP-based agent and/or pharmaceutical compositions (and/or additional therapeutic agent) are formulated as a gelatin capsule.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents.

In various embodiments, the formulations of the AP-based agents may additionally comprise a pharmaceutically acceptable carrier or excipient. As one skilled in the art will recognize, the formulations can be in any suitable form appropriate for the desired use and route of administration.

In some dosage forms, the agents described herein are mixed with at least one inert, pharmaceutically acceptable excipient or carrier such as sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpyrrolidone, methylcellulose, hydroxypropyl cellulose (HPC), and hydroxymethyl cellulose etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients may have two or more functions in the oral dosage form. In the case of an oral dosage form, for example, a capsule or a tablet, the dosage form may also comprise buffering agents.

The formulation can additionally include a surface active agent. Surface active agents suitable for use in the present invention include, but are not limited to, any pharmaceutically acceptable, non-toxic surfactant. Classes of surfactants suitable for use in the compositions of the invention include, but are not limited to polyethoxylated fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-olyoxypropylene block copolymers, sorbitan fatty acid esters, lower alcohol fatty acid esters, ionic surfactants, and mixtures thereof. In some embodiments, compositions of the invention may comprise one or more surfactants including, but not limited to, sodium lauryl sulfate, polysorbate 20, polysorbate 40, polysorbate 60, polysorbate 80, and triethyl citrate.

The formulation can also contain pharmaceutically acceptable plasticizers to obtain the desired mechanical properties such as flexibility and hardness. Such plasticizers include, but are not limited to, triacetin, citric acid esters, triethyl citrate, phthalic acid esters, dibutyl sebacate, cetyl alcohol, polyethylene glycols, polysorbates or other plasticizers.

The formulation can also include one or more application solvents. Some of the more common solvents that can be used to apply, for example, a delayed-release coating composition include isopropyl alcohol, acetone, methylene chloride and the like.

The formulation can also include one or more alkaline materials. Alkaline material suitable for use in compositions of the invention include, but are not limited to, sodium, potassium, calcium, magnesium and aluminum salts of acids such as phosphoric acid, carbonic acid, citric acid and other aluminum/magnesium compounds. In addition the alkaline material may be selected from antacid materials such as aluminum hydroxides, calcium hydroxides, magnesium hydroxides and magnesium oxide.

In various embodiments, the formulation can additionally include magnesium and/or zinc. Without wishing to be bound by theory, the inclusion of magnesium and/or zinc in the formulation promotes protein folding (e.g., dimer formation) and bioactivity of the AP-based agent. In some embodiments, the formulation can include magnesium at a concentration of from about 1 µM to greater than 5 mM (e.g., from about 1 µM to more than 5 mM), inclusive of all ranges and values therebetween. In some embodiments, the formulation can include zinc at a concentration of about 1 µM to greater than 1 mM (e.g., from about 1 µM to more than 1 mM), inclusive of all ranges and values therebetween. In various embodiments, the formulation of the present invention is substantially free of metal chelators.

In various embodiments, the pH of the formulation ensures that the AP-based agent is properly folded (e.g., dimer formation) and is bioactive. In some embodiments, the formulation is maintained at a pH such that the amino acids which coordinate the binding of magnesium and/or zinc within the AP-based agent are not protonated. Protonation of such coordinating amino acids may lead to loss of metal ions and bioactivity and dimer disassociation. In various embodiments, the pH of the formulation is greater than about 6, about 6.5, about 7, about 7.5, about 8, about 8.5, about 9, about 9.5, about 10, about 10.5, about 11, about 11.5, or about 12.

Besides inert diluents, the oral compositions can also include adjuvants such as sweetening, flavoring, and perfuming agents.

In various embodiments, the AP-based agent and/or pharmaceutical compositions (and/or additional therapeutic agents) are formulated for systemic or local delivery. In an embodiment, administration is systemic. In another embodiment, it may be desirable to administer locally to the area in need of treatment.

Various methods may be used to formulate and/or deliver the agents described herein to a location of interest. For example, the alkaline phosphatase and/or pharmaceutical compositions (and/or additional therapeutic agents) described herein may be formulated for delivery to the gastrointestinal tract. The gastrointestinal tract includes organs of the digestive system such as mouth, esophagus, stomach, duodenum, small intestine, large intestine and rectum and includes all subsections thereof (e.g. the small intestine may include the duodenum, jejunum and ileum; the large intestine may include the colon transversum, colon descendens, colon ascendens, colon sigmoidenum and cecum). For example, the alkaline phosphatases and/or pharmaceutical compositions (and/or additional therapeutic agents) described herein may be formulated for delivery to one or more of the stomach, small intestine, large intestine and rectum and includes all subsections thereof (e.g. duodenum, jejunum and ileum, colon transversum, colon descendens, colon ascendens, colon sigmoidenum and cecum). In some embodiments, the compositions described herein may be formulated to deliver to the upper or lower GI tract. In an embodiment, the alkaline phosphatases and/or pharmaceutical compositions (and/or additional therapeutic agents) may be administered to a subject, by, for example, directly or indirectly contacting the mucosal tissues of the gastrointestinal tract.

In various embodiments, the administration the AP-based agent and/or pharmaceutical compositions (and/or additional therapeutic agents) is into the GI tract via, for example, oral delivery, nasogastral tube, intestinal intubation (e.g. an enteral tube or feeding tube such as, for example, a jejunal tube or gastro-jejunal tube, etc.), direct infusion (e.g., duodenal infusion), endoscopy, colonoscopy, or enema.

For example, in various embodiments, the present invention provides modified release formulations comprising at least one AP-based agent (and/or additional therapeutic agents), wherein the formulation releases a substantial amount of the AP-based agent (and/or additional therapeutic agents) into one or more regions of the GI tract. For example, the formulation may release at least about 60% of the AP-based agent after the stomach and into one or more regions of the GI tract.

In various embodiments, the modified-release formulation of the present invention releases at least 60% of the AP-based agent (or additional therapeutic agents) after the stomach into one or more regions of the intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (or additional therapeutic agents) in the intestines.

In various embodiments, the modified-release formulation of the present invention releases at least 60% of the AP-based agent (or additional therapeutic agents) in the small intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (or additional therapeutic agents) in the small intestine (e.g., one or more of duodenum, jejunum, ileum, and ileocecal junction).

In various embodiments, the modified-release formulation of the present invention releases at least 60% of the AP-based agent (or additional therapeutic agents) in the large intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (or additional therapeutic agents) in the large intestine (e.g., one or more of cecum, ascending, transverse, descending or sigmoid portions of the colon, and rectum).

In various embodiments, the modified-release formulation does not substantially release the AP-based agent (or additional therapeutic agents) in the stomach.

In certain embodiments, the modified-release formulation releases the AP-based agent (or additional therapeutic agents) at a specific pH. For example, in some embodiments, the modified-release formulation is substantially stable in an acidic environment and substantially unstable (e.g., dissolves rapidly or is physically unstable) in a near neutral to alkaline environment. In some embodiments, stability is indicative of not substantially releasing while instability is indicative of substantially releasing. For example, in some embodiments, the modified-release formulation is substantially stable at a pH of about 7.0 or less, or about 6.5 or less, or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. In some embodiments, the present formulations are stable in lower pH areas and therefore do not substantially release in, for example, the stomach. In some embodiments, modified-release formulation is substantially stable at a pH of about 1 to about 4 or lower and substantially unstable at pH values that are greater. In these embodiments, the modified-release formulation does not substantially release in the stomach. In these embodiments, the modified-release formulation substantially releases in the small intestine (e.g. one or more of the duodenum, jejunum, and ileum) and/or large intestine (e.g. one or more of the cecum, ascending colon, transverse colon, descending colon, and sigmoid colon). In some embodiments, modified-release formulation is substantially stable at a pH of about 4 to about 5 or lower and consequentially is substantially unstable at pH values that are greater and therefore is not substantially released in the stomach and/or small intestine (e.g. one or more of the duodenum, jejunum, and ileum). In these embodiments, the modified-release formulation substantially releases in the large intestine (e.g. one or more of the cecum, ascending colon, transverse colon, descending colon, and sigmoid colon). In various embodiments, the pH values recited herein may be adjusted as known in the art to account for the state of the subject, e.g. whether in a fasting or postprandial state.

In some embodiments, the modified-release formulation is substantially stable in gastric fluid and substantially unstable in intestinal fluid and, accordingly, is substantially released in the small intestine (e.g. one or more of the duodenum, jejunum, and ileum) and/or large intestine (e.g. one or more of the cecum, ascending colon, transverse colon, descending colon, and sigmoid colon).

In some embodiments, the modified-release formulation is stable in gastric fluid or stable in acidic environments. These modified-release formulations release about 30% or less by weight of the alkaline phosphatase and/or additional therapeutic agent in the modified-release formulation in gastric fluid with a pH of about 4 to about 5 or less, or simulated gastric fluid with a pH of about 4 to about 5 or less, in about 15, or about 30, or about 45, or about 60, or about 90 minutes. Modified-release formulations of the of the invention may release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of the alkaline phosphatase and/or additional therapeutic agent in the modified-release formulation in gastric fluid with a pH of 4-5, or less or simulated gastric fluid with a pH of 4-5 or less, in about 15, or about 30, or about 45, or about 60, or about 90 minutes. Modified-release formulations of the invention may release about 1%, about 2%, about 3%, about 4%, about 5%, about 6%, about 7%, about 8%, about 9%, or about 10% by weight of the total alkaline phosphatase and/or additional therapeutic agent in the modified-release formulation in gastric fluid with a pH of 5 or less, or simulated gastric fluid with a pH of 5 or less, in about 15, or about 30, or about 45, or about 60, or about 90 minutes.

In some embodiments, the modified-release formulation is unstable in intestinal fluid. These modified-release formulations release about 70% or more by weight of the alkaline phosphatase and/or additional therapeutic agent in the modified-release formulation in intestinal fluid or simulated intestinal fluid in about 15, or about 30, or about 45, or about 60, or about 90 minutes. In some embodiments, the modified-release formulation is unstable in near neutral to alkaline environments. These modified-release formulations release about 70% or more by weight of the alkaline phosphatase and/or additional therapeutic agent in the modified-release formulation in intestinal fluid with a pH of about 4-5 or greater, or simulated intestinal fluid with a pH of about 4-5 or greater, in about 15, or about 30, or about 45, or about 60, or about 90 minutes. A modified-release formulation that is unstable in near neutral or alkaline environments may release 70% or more by weight of alkaline phosphatase and/or additional therapeutic agent in the modified-release formulation in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

In various embodiments, the modified-release formulation of the invention is substantially stable in chyme. For example, there is, in some embodiments, a loss of less than about 50% or about 40%, or about 30%, or about 20%, or about 10% of AP-based agent activity in about 10, or 9, or 8, or 7, or 6, or 5, or 4, or 3, or 2, or 1 hour from administration.

In various embodiments, the modified-release formulations of the present invention are designed for immediate release (e.g. upon ingestion). In various embodiments, the modified-release formulations may have sustained-release profiles, i.e. slow release of the active ingredient(s) in the body (e.g., GI tract) over an extended period of time. In various embodiments, the modified-release formulations may have a delayed-release profile, i.e. not immediately release the active ingredient(s) upon ingestion; rather, postponement of the release of the active ingredient(s) until the composition is lower in the gastrointestinal tract; for example, for release in the small intestine (e.g., one or more of duodenum, jejunum, ileum) or the large intestine (e.g., one or more of cecum, ascending, transverse, descending or sigmoid portions of the colon, and rectum). For example, a composition can be enteric coated to delay release of the active ingredient(s) until it reaches the small intestine or large intestine.

In various embodiments, the modified-release formulation of the present invention may utilize one or more modified-release coatings such as delayed-release coatings to provide for effective, delayed yet substantial delivery of the alkaline phosphatase to the GI tract together with, optionally, additional therapeutic agents.

In various embodiments, the modified-release formulation of the present invention may utilize one or more modified-release coatings such as delayed-release coatings to provide for effective, delayed yet substantial delivery of the alkaline phosphatase to the intestines together with, optionally, other additional therapeutic agents.

In one embodiment, the delayed-release coating includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly (methacrylic acid, methylmethacrylate), hydroxypropyl methylcellulose acetate succinate, cellulose acetate trimellitate, shellac or other suitable enteric coating polymers. The EUDRAGIT®-type polymers include, for example, EUDRAGIT® FS 30D, L 30 D-55, L 100-55, L 100, L 12,5, L 12,5 P, RL 30 D, RL PO, RL 100, RL 12,5, RS 30 D, RS PO, RS 100, RS 12,5, NE 30 D, NE 40 D, NM 30 D, S 100, S 12,5, and S 12,5 P. Similar polymers include Kollicoat® MAE 30 DP and Kollicoat® MAE 100 P. In some embodiments, one or more of EUDRAGIT® FS 30D, L 30 D-55, L 100-55, L 100, L 12,5, L 12,5 P RL 30 D, RL PO, RL 100, RL 12,5, RS 30 D, RS PO, RS 100, RS 12,5, NE 30 D, NE 40 D, NM 30 D, S 100, S 12,5 S 12,5 P, Kollicoat® MAE 30 DP and Kollicoat® MAE 100 P is used. In various embodiments, the enteric agent may be a combination of the foregoing solutions or dispersions. In an embodiment, the delayed-release coating includes the enteric agent EUDRAGIT® L 30 D-55.

In certain embodiments, one or more coating system additives are used with the enteric agent. For example, one or more PlasACRYL™ additives may be used as an antitacking agent coating additive. Illustrative PlasACRYL™ additives include, but are not limited to PlasACRYL™ HTP20 and PlasACRYL™ T20. In an embodiment, PlasACRYL™ HTP20 is formulated with EUDRAGIT® L 30 D-55 coatings. In another embodiment, PlasACRYL™ T20 is formulated with EUDRAGIT® FS 30 D coatings.

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, and EUDRAGIT NE®. Insoluble polymers useful in the present invention include polyvinyl esters, polyvinyl acetals, polyacrylic acid esters, butadiene styrene copolymers, and the like. In one embodiment, colonic delivery is achieved by use of a slowly-eroding wax plug (e.g., various PEGS, including for example, PEG6000).

In a further embodiment, the delayed-release coating may be degraded by a microbial enzyme present in the gut flora. In one embodiment, the delayed-release coating may be degraded by a bacteria present in the small intestine. In another embodiment, the delayed-release coating may be degraded by a bacteria present in the large intestine.

In various embodiments, the modified release formulation is designed for release in the colon. Various colon-specific delivery approaches may be utilized. For example, the modified release formulation may be formulated using a colon-specific drug delivery system (CODES) as described for example, in Li et al, AAPS PharmSciTech (2002), 3(4): 1-9, the entire contents of which are incorporated herein by reference. Drug release in such a system is triggered by colonic microflora coupled with pH-sensitive polymer coatings. For example, the formulation may be designed as a core tablet with three layers of polymer. The first coating is an acid-soluble polymer (e.g., EUDRAGIT E), the outer coating is enteric, along with a hydroxypropyl methylcellulose barrier layer interposed in between. In another embodiment, colon delivery may be achieved by formulating the alkaline phosphatase (and/or additional therapeutic agent) with specific polymers that degrade in the colon such as, for example, pectin. The pectin may be further gelled or cross-linked with a cation such as a zinc cation. In an embodiment, the formulation is in the form of ionically crosslinked pectin beads which are further coated with a polymer (e.g., EUDRAGIT polymer). Additional colon specific formulations include, but are not limited to, pressure-controlled drug delivery systems (prepared with, for example, ethylcellulose) and osmotic controlled drug delivery systems (i.e., ORDS-CT).

Formulations for colon specific delivery of the AP-based agent (and/or additional therapeutic agents), as described herein, may be evaluated using, for example, in vitro dissolution tests. For example, parallel dissolution studies in different buffers may be undertaken to characterize the behavior of the formulations at different pH levels. Alternatively, in vitro enzymatic tests may be carried out. For example, the formulations may be incubated in fermenters containing suitable medium for bacteria, and the amount of drug released at different time intervals is determined. Drug release studies can also be done in buffer medium containing enzymes or rat or guinea pig or rabbit cecal contents and the amount of drug released in a particular time is determined. In a further embodiment, in vivo evaluations may be carried out using animal models such as dogs, guinea pigs, rats, and pigs. Further, clinical evaluation of colon specific drug delivery formulations may be evaluated by calculating drug delivery index (DDI) which considers the relative ratio of RCE (relative colonic tissue exposure to the drug) to RSC (relative amount of drug in blood i.e. that is relative systemic exposure to the drug). Higher drug DDI indicates better colon drug delivery. Absorption of drugs from the colon may be monitored by colonoscopy and intubation.

In various embodiments, the present formulation provide for substantial uniform dissolution of the AP-based agent (and/or additional therapeutic agent) in the area of release in the GI tract. In an embodiment, the present formulation minimizes patchy or heterogeneous release of the AP-based agent.

In various embodiments, the present invention provides for modified-release formulations that release multiple doses of the AP-based agent, at different locations along the intestines, at different times, and/or at different pH. In an illustrative embodiment, the modified-release formulation comprises a first dose of the AP-based agent and a second dose of the AP-based agent, wherein the first dose and the second dose are released at different locations along the intestines, at different times, and/or at different pH. For example, the first dose is released at the duodenum, and the second dose is released at the ileum. In another example, the first dose is released at the jejunum, and the second dose is released at the ileum. In other embodiments, the first dose is released at a location along the small intestine (e.g., the duodenum), while the second dose is released along the large intestine (e.g., the ascending colon). In various embodiments, the modified-release formulation may release at least one dose, at least two doses, at least three doses, at least four doses, at least five doses, at least six doses, at least seven doses, or at least eight doses of the AP-based agent at different locations along the intestines, at different times, and/or at different pH. Further the dual pulse description herein applies to modified-release formulations that release the AP-based agent and an additional therapeutic agent.

In various embodiments, the invention provides a formulation comprising: a core particle having a base coat comprising one or more AP-based agents, and a delayed-release coating disposed over the coated core particle. The delayed-release coating may be substantially stable in acidic environments and/or gastric fluid, and/or substantially unstable in near neutral to alkaline environments or intestinal fluid thereby exposing the coated core particle to intestinal fluid. The base coat comprising one or more AP-based agents may further comprise one or more additional therapeutic agents. Optionally a plurality of base coats may be applied to the core particle each of which may contain an AP-based agent and/or an additional therapeutic agent. In an embodiment, the core particle includes sucrose. In an embodiment, an AP-based agent can be sprayed onto an inert core (e.g., a sucrose core) and spray-dried with an enteric layer (e.g., EUDRAGIT L30 D-55) to form pellets or beads containing AP-based agents.

Optionally, the core particle may comprise one or more AP-based agents and/or one or more additional therapeutic agents. In one embodiment, one or more doses of the AP-based agent may be encapsulated in a core particle, for example, in the form of a microsphere or a mini-sphere. For example, the AP-based agent may be combined with a polymer (e.g., latex), and then formed into a particulate, micro-encapsulated enzyme preparation, without using a sucrose core. The microspheres or mini-spheres thus formed may be optionally covered with a delayed-release coating.

A variety of approaches for generating particulates (such as microspheres, mini-spheres, aggregates, other) may be utilized for the inclusion of enzymatic proteins. They typically involve at least two phases, one containing the protein, and one containing a polymer that forms the backbone of the particulate. Most common are coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form, for example, microspheres or mini-spheres. Alternatively, the alkaline phosphatase and stabilizing excipients (for example, trehalose, mannitol, Tween 80, polyvinyl alcohol) are combined and sprayed from aqueous solution and collected. The particles are then suspended in a dry, water immiscible organic solvent containing polymer and release modifying compounds, and the suspension sonicated to disperse the particles.

An additional approach uses aqueous phases but no organic solvent. Specifically, the enzymatic protein, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. When the release modifiers are insoluble at acidic conditions but soluble at higher pHs (such as carboxylic acid) then release from the matrix is inhibited in the gastric environment. In an embodiment, alkaline phosphatase may be initially solubilized as an emulsion, microemulsion, or suspension and then formulated into solid mini-spheres or microspheres. The formulation may then be coated with, for example, a delayed-release, sustained-release, or controlled-release coating to achieve delivery at a specific location such as, for example, the intestines.

In various embodiments, the formulation may comprise a plurality of modified-release particles or beads or pellets or microspheres. In an embodiment, the formulation is in the form of capsules comprising multiple beads. In another embodiment, the formulation is in the form of capsules comprising multiple pellets. In another embodiment, the formulation is in the form of capsules comprising multiple microspheres or mini-spheres.

In some embodiments, before applying the delayed-release coating to the coated core particle, the particle can optionally be covered with one or more separating layers comprising pharmaceutical excipients including alkaline compounds such as for instance pH-buffering compounds. The separating layer essentially separates the coated core particle from the delayed-release coating.

The separating layer can be applied to the coated core particle by coating or layering procedures typically used with coating equipment such as a coating pan, coating granulator or in a fluidized bed apparatus using water and/or organic solvents for the coating process. As an alternative the separating layer can be applied to the core material by using a powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methyl-cellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, sodium stearyl fumarate, titanium dioxide, talc and other additives can also be included in the separating layer.

In some embodiments, the coated particles with the delayed-release coating may be further covered with an overcoat layer. The overcoat layer can be applied as described for the other coating compositions. The overcoat materials are pharmaceutically acceptable compounds such as sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. The overcoat materials can prevent potential agglomeration of particles coated with the delayed-release coating, protect the delayed-release coating from cracking during the compaction process or enhance the tableting process. In various embodiments, the formulations of the present invention take the form of those as described in International Patent Application No. PCT/US15/54606, the entire contents of all of which are incorporated herein by reference.

In various embodiments, the formulations of the present invention take the form of those as described in one or more of U.S. Pat. Nos. 8,535,713 and 8,9117,77 and U.S. Patent Publication Nos. 20120141585, 20120141531, 2006/001896, 2007/0292523, 2008/0020018, 2008/0113031, 2010/0203120, 2010/0255087, 2010/0297221, 2011/0052645, 2013/0243873, 2013/0330411, 2014/0017313, and 2014/0234418, the contents of which are hereby incorporated by reference in their entirety.

In various embodiments, the formulations of the present invention take the form of those as described in International Patent Publication No. WO 2008/135090, the contents of which are hereby incorporated by reference in their entirety.

In various embodiments, the formulations of the present invention take the form of those described in one or more of U.S. Pat. Nos. 4,196,564; 4,196,565; 4,247,006; 4,250,997; 4,268,265; 5,317,849; 6,572,892; 7,712,634; 8,074,835; 8,398,912; 8,440,224; 8,557,294; 8,646,591; 8,739,812; 8,810,259; 8,852,631; and 8,911,788 and US Patent Publication Nos. 2014/0302132; 2014/0227357; 20140088202; 20130287842; 2013/0295188; 2013/0307962; and 20130184290, the contents of which are hereby incorporated by reference in their entirety.

In various embodiments, the process of formulating the AP-based agent is sufficiently gentle such that the tertiary structure of the AP-based agent (e.g., dimeric structure) is substantially intact. In various embodiments, the process of formulating the AP-based agent includes a step of refolding the AP-based agent. In such embodiments, the step of refolding the AP-based agent may include the addition of magnesium and/or cyclodextrin.

Administration and Dosages

It will be appreciated that the actual dose of the AP-based agent to be administered according to the present invention will vary according to the particular compound, the particular dosage form, and the mode of administration. Many factors that may modify the action of the AP-based agent (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

Individual doses of the AP-based agent can be administered in unit dosage forms (e.g., tablets or capsules) containing, for example, from about 0.01 mg to about 1,000 mg, about 0.01 mg to about 900 mg, about 0.01 mg to about 800 mg, about 0.01 mg to about 700 mg, about 0.01 mg to about 600 mg, about 0.01 mg to about 500 mg, about 0.01 mg to about 400 mg, about 0.01 mg to about 300 mg, about 0.01 mg to about 200 mg, from about 0.1 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg, from about 0.1 mg to about 30 mg, from about 0.1 mg to about 20 mg, from about 0.1 mg to about 10 mg, from about 0.1 mg to about 5 mg, from about 0.1 mg to about 3 mg, or from about 0.1 mg to about 1 mg active ingredient per unit dosage for. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 200 mg, about 300 mg, about 400 mg, about 500 mg, about 600 mg, about 700 mg, about 800 mg, about 900 mg, or about 1,000 mg of the AP-based agent, inclusive of all values and ranges therebetween.

In one embodiment, the AP-based agent is administered at an amount of from about 0.01 mg to about 1,000 mg daily, about 0.01 mg to about 900 mg daily, about 0.01 mg to about 800 mg daily, about 0.01 mg to about 700 mg daily, about 0.01 mg to about 600 mg daily, about 0.01 mg to about 500 mg daily, about 0.01 mg to about 400 mg daily, about 0.01 mg to about 300 mg daily, about 0.01 mg to about 200 mg daily, about 0.01 mg to about 100 mg daily, an amount of from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the AP-based agent is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 200 mg, about 300 mg, about 400 mg, about 500 mg, about 600 mg, about 700 mg, about 800 mg, about 900 mg, or about 1,000 mg, inclusive of all values and ranges therebetween.

In some embodiments, a suitable dosage of the AP-based agent is in a range of about 0.01 mg/kg to about 100 mg/kg of body weight of the subject, about 0.01 mg/kg to about 90 mg/kg of body weight of the subject, about 0.01 mg/kg to about 80 mg/kg of body weight of the subject, about 0.01 mg/kg to about 70 mg/kg of body weight of the subject, about 0.01 mg/kg to about 60 mg/kg of body weight of the subject, about 0.01 mg/kg to about 50 mg/kg of body weight of the subject, about 0.01 mg/kg to about 40 mg/kg of body weight of the subject, about 0.01 mg/kg to about 30 mg/kg of body weight of the subject, about 0.01 mg/kg to about 20 mg/kg of body weight of the subject, about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 20 mg/kg body weight, about 30 mg/kg body weight, about 40 mg/kg body weight, about 50 mg/kg body weight, about 60 mg/kg body weight, about 70 mg/kg body weight, about 80 mg/kg body weight, about 90 mg/kg body weight, or about 100 mg/kg body weight, inclusive of all values and ranges therebetween. In other embodiments, a suitable dosage of the AP-based agent is in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of about 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In accordance with certain embodiments of the invention, the AP-based agent may be administered, for example, more than once daily (e.g., about two, about three, about four, about five, about six, about seven, about eight, about nine, or about ten times per day), about once per day, about every other day, about every third day, about once a week, about once every two weeks, about once every month, about once every two months, about once every three months, about once every six months, or about once every year.

Methods of Treatment

In some aspects, the present invention provides methods for the therapeutic use of an AP-based agent. In an embodiment, the present invention provides methods for the treatment or prevention of one or more neurodevelopmental disorders.

In various embodiments, the present methods reduce or prevent an impairment of the growth and development of the brain or central nervous system (CNS).

In various embodiments, the subject is a pregnant woman. In various embodiments, the pregnant woman is afflicted with one or more of gastrointestinal dysbiosis, obesity, metabolic syndrome, gut-mediated systemic inflammation, and leaky gut. In various embodiments, the offspring of the pregnant woman is prevented from developing a neurodevelopmental disorder.

In various embodiments, the neurodevelopmental disorder is one or more of autism spectrum disorder (ASD), schizophrenia, attention deficit hyperactivity disorder (ADHD), schizoaffective disorder, and bipolar affective disorder.

In various embodiments, the neurodevelopmental disorder is ASD.

In some aspects, the present invention provides a method of treating autism spectrum disorder (ASD), comprising administering an effective amount of an AP-based agent described herein, including without limitation, orally administered IAP, to a patient in need thereof.

In various embodiments, the method provides administering an AP-based agent, including without limitation orally administered IAP, to a pregnant woman afflicted with a risk factor for ASD (e.g., without limitation, one or more of gastrointestinal dysbiosis, obesity, metabolic syndrome, gut-mediated systemic inflammation, and leaky gut), to reduce the likelihood of the subject's offspring from developing ASD (and/or reducing or eliminating one or more symptoms of ASD in the subject's offspring).

ASD are a group of diseases characterized by varying degrees of impairment in communication skills, social interactions, and restricted, repetitive and stereotyped patterns of behavior. The difference in the diseases depends on the time of onset, the rate of symptom development, the severity of symptoms, and the exact nature of the symptoms.

These disorders range from mild to severe impairment and include such diseases as autism, Asperger's syndrome, PDD-NOS, Rett's disorder, childhood disintegrative disorder, semantic communication disorder, non-verbal learning disabilities, high functioning autism, hyperlexia and some aspects of attention deficit hyperactivity disorder.

In various embodiments, the method reduces one or more symptoms of ASD as noted in the DSM-IV or other such autism-specific diagnostic methodology. According to the Autism Society of America (ASA), autism is generally characterized as one of five disorders coming under the umbrella of Pervasive Developmental Disorders (PDD), a category of neurological disorders characterized by severe and pervasive impairment in several areas of development, including social interaction and communications skills (DSM-IV-TR). The five disorders under PDD, which are treated or prevented in various embodiments of the present methods are: autistic disorder, Asperger's Disorder, childhood disintegrative disorder (CDD, or Heller's syndrome), Rett's Disorder or Rett's Syndrome, and pervasive developmental disorder-not otherwise specified (PDD-NOS, or atypical autism).

Specific or Explicit diagnostic criteria for each of these disorders can be found in the Diagnostic & Statistical Manual of Mental Disorders (DSM IV-TR) as distributed by the American Psychiatric Association (APA).

In various embodiments, the method provides treatment that is manifested in a reversal of one or more of the DSM-IV's twelve diagnostic criteria, which fall into three categories: (1) impairments in social interaction (e.g. marked impairment in the use of multiple nonverbal behaviors such as eye-to-eye gaze, facial expression, body postures, and gestures to regulate social interaction; failure to develop peer relationships appropriate to developmental level; a lack of spontaneous seeking to share enjoyment, interests, or achievement with other people (e.g., by a lack of showing, bringing, or pointing out objects of interest); and lack of social or emotional reciprocity); (2) impairments in communication (e.g., delay in, or total lack of, the development of spoken language (not accompanied by an attempt to compensate through alternative modes of communication such as gesture or mime); in individuals with adequate speech, marked impairment in the ability to initiate or sustain a conversation with others; stereotyped and repetitive use of language or idiosyncratic language; and lack of varied, spontaneous make-believe play or social imitative play appropriate to developmental level), and (3) a restricted repertoire of activities and interests (e.g., encompassing preoccupation with one or more stereotyped and restricted patterns of interest that is abnormal either in intensity or focus; apparently inflexible adherence to specific, nonfunctional routines or rituals; stereotyped and repetitive motor mannerisms (e.g., hand or finger flapping or twisting, or complex whole-body movements); and persistent preoccupation with parts of objects).

The following traits, as identified by the ASA, may also be present in persons with autism and are reduced or eliminated by the present methods in various embodiments: insistence on sameness or resistance to change; difficulty in expressing needs; (i.e. uses gestures or pointing instead of words); repeating words or phrases in place of normal, responsive language; laughing, crying, showing distress for reasons not apparent to others; prefers to be alone or aloof manner; tantrums; difficulty in mixing with others; may not want to cuddle or be cuddled; minor or no eye contact; unresponsive to normal teaching methods; sustained odd play; spins objects; inappropriate attachments to objects; apparent over-sensitivity or under-sensitivity to pain; no real fears of danger; noticeable physical over-activity or extreme under-activity; and uneven gross/fine motor skills; and/or not responsive to verbal cues (i.e. acts as if deaf although hearing tests in normal range).

In various embodiments, the present methods may be useful in treating one or more symptoms or characteristics of ASD, which include, by way of non-limiting example, stereotyped movements, social withdrawal and averted gaze including an inability to make eye contact, repetitive behaviors and obsessions, anxiety, attention deficit, hyperactivity, depression, a reclusive personality, and the inability to understand feelings. Patients afflicted with ASD may have an aversion to physical affection or contact, ignore communication from others, or if socially engaged, demonstrate a marked inability to communicate or relate to others. Communication difficulties may manifest as a monotone voice, an inability to control the volume of their voice, echolalia or an inability to talk at all. Individuals with autism spectrum disorders may also suffer from visual difficulties, comprehension difficulties, sound and light sensitivity and mental retardation.

In various embodiments, the present methods may be useful in treating one or more symptoms or characteristics of ASD, which include, by way of non-limiting example, reduced communication message skills (e.g. not speaking or very limited speech; loss of words the child was previously able to say; difficulty expressing basic wants and needs; poor vocabulary development; problems following directions or finding objects that are named; repeating what is said (echolalia); problems answering questions; and speech that sounds different (e.g., "robotic" speech or speech that is high-pitched) and or reduced social community skills (e.g. poor eye contact with people or objects, poor play skills (pretend or social play), being overly focused on a topic or objects that interest them, problems making friends, crying, becoming angry, giggling, or laughing for no known reason or at the wrong time, and disliking being touched or held); various reduced response mechanisms (e.g. rocking, hand flapping or other movements (self-stimulating movements), not paying attention to things the child sees or hears, problems dealing with changes in routine, using objects in unusual ways, unusual attachments to objects, no fear of real dangers, being either very sensitive or not sensitive enough to touch, light, or sounds (e.g., disliking loud sounds or only responding when sounds are very loud; also called a sensory integration disorder), feeding difficulties (accepting only select foods, refusing certain food textures), and sleep problems).

The effectiveness of the AP-based agents for these and related conditions can be demonstrated according to a variety of methods, including, for example, by measuring markers such as those measured in the Checklist of Autism in Toddlers (CHAT), the modified Checklist for Autism in Toddlers (M-CHAT), the Screening Tool for Autism in Two-Year-Olds (STAT), the Social Communication Questionnaire (SCQ), the Autism Spectrum Screening Questionnaire (ASSQ), the Australian Scale for Asperger's Syndrome, the Childhood Asperger Syndrome Test (CAST), the Autism Diagnosis Interview-Revised (ADI-R), the Autism Diagnostic Observation Schedule (ADOS-G), the Childhood Autism Rating Scale (CARS), audiologic hearing evaluation, Administered PTSD Scale, the Eysenck Personality Inventory, the Hamilton Anxiety Scale, or in various animal models such as the well-known Vogel (thirsty rat conflict) test, or the elevated plus maze test. Effective amounts of the present compounds and compositions (and, optionally, an additional therapeutic agent) will measurably prevent, decrease the severity of, or delay the onset or duration of, one or more of the foregoing autism spectrum disorders or related disorders of symptoms of such disorders in a patient. Further, the DSM-5, e.g. the section entitled "ASD and Social Communication Disorder," which is hereby incorporated by reference in its entirety, and the International Statistical Classification of Diseases and Related Health Problems-10th Revision (ICD-10) can be used as diagnostic classifications for ASD. In some embodiments, stereotypy is useful as a diagnostic for ASD, including in children with autism.

In some embodiments, the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish.

In various embodiments, methods of the invention are useful in treating a human subject. In some embodiments, the human is a pediatric human. In other embodiments, the human is an adult human. In other embodiments, the human is a geriatric human. In other embodiments, the human may be referred to as a patient. In some embodiments, the human is a female. In some embodiments, the human is a male.

As described elsewhere herein, in various embodiments, the human subject is a pregnant female. As described elsewhere herein, in various embodiments, the human subject is an unborn child.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

Additional Therapeutic Agents and Combination Therapy

Administration of the present compositions and formulations comprising the AP-based agent may be combined with additional therapeutic agents. Co-administration of the additional therapeutic agent and the present compositions/formulations may be simultaneous or sequential. Further, the present compositions/formulations may comprise an additional therapeutic agent (e.g. via co-formulation). For example, the additional therapeutic agent and the AP-based agent may be combined into a single formulation. Alternatively, the additional therapeutic agent and the AP-based agent may be formulated separately.

In one embodiment, the additional therapeutic agent and the AP-based agent are administered to a subject simultaneously. The term "simultaneously" as used herein, means that the additional therapeutic agent and the AP-based agent are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the AP-based agent can be by simultaneous administration of a single formulation (e.g., a formulation comprising the additional therapeutic agent and the alkaline phosphatase) or of separate formulations (e.g., a first formulation including the additional therapeutic agent and a second formulation including the AP-based agent).

In a further embodiment, the additional therapeutic agent and the AP-based agent are administered to a subject simultaneously but the release of the additional therapeutic agent and the alkaline phosphatase from their respective dosage forms (or single unit dosage form if co-formulated) may occur sequentially.

Co-administration does not require the additional therapeutic agent and the AP-based agent to be administered simultaneously, if the timing of their administration is such that the pharmacological activities of the additional therapeutic agent and the AP-based agent overlap in time. For example, the additional therapeutic agent and the AP-based agent can be administered sequentially. The term "sequentially" as used herein means that the additional therapeutic agent and the AP-based agent are administered with a time separation of more than about 60 minutes. For example, the time between the sequential administration of the additional therapeutic agent and the AP-based agent can be more than about 60 minutes, more than about 2 hours, more than about 5 hours, more than about 10 hours, more than about 1 day, more than about 2 days, more than about 3 days, or more than about 1 week apart. The optimal administration times will depend on the rates of metabolism, excretion, and/or the pharmacodynamic activity of the additional therapeutic agent and the AP-based agent being administered. Either the additional therapeutic agent or the AP-based agent may be administered first.

Co-administration also does not require the additional therapeutic agent and the AP-based agent to be administered to the subject by the same route of administration. Rather, each therapeutic agent can be administered by any appropriate route, for example, parenterally or non-parenterally.

In various embodiments, the present agents are used in conjunction with applied behavior analysis or other behavior modification techniques; dietary alteration such as a gluten or casein free diet; vitamin B6, optionally combined with magnesium; and one or more additional agents.

In various embodiments, the additional agents are neurotransmitter reuptake inhibitors (e.g. fluoxetine), tricyclic antidepressants (e.g. imipramine), anticonvulsants (e.g. lamotrigine), atypical antipsychotics (e.g. clozapine), acetylcholinesterase inhibitors (e.g. rivastigmine).

In various embodiments, the additional agent is an anti-anxiety and/or anti-depression agent such as fluoxetine, fluvoxamine, sertraline and clomipramine. In various embodiments, the additional agent is an antipsychotic medication such as chlorpromazine, thioridazine, and haloperidol. In various embodiments, the additional agent is an anticonvulsant agent such as arbamazepine, lamotrigine, topiramate, and valproic acid.

EXAMPLES

Example 1. Stability of AP-Based Agent in Chyme

The stability of various AP-based agents in chyme is assessed. Chyme specimens (5 individual and 1 mixed) are first evaluated for background alkaline phosphatase activity prior to use in analysis, and chyme specimens with the lowest amount of background activity are used for the stability study. Three separate AP proteins, hiAP, biAP, and a hiAP-FC fusion are incubated at 37° C. in a HEPES buffer containing 5% clarified human chyme. Two aliquots from each sample are removed at 0, 30, 60, 120, 180, and 240 minutes of incubation. One aliquot is immediately mixed with Laemli sample buffer for SDS-PAGE analysis and the other is immediately mixed with a protease inhibitor cocktail and stored frozen for analysis of AP activity. The samples are also incubated in HEPES buffer alone and aliquots removed at 0 and 240 minutes as controls. Collected samples are subjected to SDS-PAGE and the products of incubation examined by Coomassie blue staining.

Alkaline phosphatase activity before and after incubation in chyme is examined using a commercial kit (Abcam). It is expected that all AP-based agents remain stable in chyme for the entire duration of the experiment. Additionally, there is no reduction in AP activity after chyme incubation, which confirms that the AP-based agents are not degraded in chyme under the tested conditions.

Example 2. Engineering Bacterial AP-based Agent to Increase Catalytic Activity by Specific Amino Acids Changes There are some functional differences between the bacterial and mammalian APs. By and large, the mammalian enzymes exhibit 20-30- fold higher catalytic activity as well as a shift in the pH of optimal activity towards higher pH. Some mammalian alkaline phosphatases also require magnesium in order to achieve maximal activity. In addition, it is not known whether bacterial AP maintains the same de-phosphorylation pattern as the mammalian APs. By nucleotide comparison with mammalian AP, the bacterial *Escherichia coli* AP has been successfully engineered to achieve activity similar to the mammalian AP. Several residues have been mutagenized and AP activity assessed. Previous work indicated that the D101S mutant in *Escherichia coli* AP, which contains an Asp/Ser replacement within the -Asp101- Ser102-Ala103- region of the active center, showed a 10-fold higher activity over the wild-type AP ((Zhang, F. Appl. Biochem. Biotechnol. 2002; 101:197-210). Double mutants such as D153H/K328H resulted in enhanced activity and properties of *E. coli* AP similar to the mammalian alkaline phosphatases, and the D153H/K328H mutant enzyme is 5.6-fold more active than the wild-type enzyme. Furthermore, the double mutant D153G/D330N is as active as the mammalian AP, with 40- to 50-fold higher activity than that of the wild-type bacterial enzyme (Le Du M-H., 2002; Murphy, J E., 1994; Muller, B H., 2001).

To engineer the BSAP IV, the BSAP IV sequence disclosed herein (e.g., SEQ ID NO:17) is synthesized de novo with single, double, triple or quadruple mutations at positions D101A, W328H, A330N and G374C. The BSAP variants are tested in various in vitro and in vivo assays for their therapeutic potentials.

Example 3: Engineering Bacterial AP-Based Agent to Increase Catalytic Activity by Directed Evolution Error-prone PCR (Leung, D. Technique, 1989; 1:11-15) and DNA shuffling are utilized to identify mutations in the mammalian and bacterial AP gene that can confer an increased activity.

For example, for the error-prone PCR, specific primers are used to amplify regions of the BSAP IV gene. Primers are designed to amplify specific regions of the BSAP IV coding sequence that do not affect mutation already known to increase BSAP IV activity. The PCR parameters are as follow: 1 mM dCTP, 1 mM dTTP, 0.2 mM dATP, 0.2 mM dGTP, 7 mM $Mg^{2+}$, 0.05 mM $Mn^{2+}$, 50 ng of each primer, 1×Taq DNA polymerase buffer, 10 ng of DNA template and 2.5 units of Taq DNA polymerase in 50 ml final volume. The reaction is subjected to 25 cycles as follows: 1 minute at 94° C., 1 minute at 56° C., and 1.5 minutes at 72° C. to generate an error frequency of approximately 1 to 2 substitutions per 1000 bases. The amplified products are digested appropriate restriction endonucleases, followed by the ligation with the same digested template vector. The *E. coli* SL21 (DE3) containing sequences from the error prone PCR is then transformed with the ligation mixture to create the mutant library (Moore, J C. Nat. Biotechnol. 1996; 14:458-467).

DNA shuffling is performed as described by Stemmer (Proc. Natl. Acad. Sci. USA, 1994; 91:10747-10751) and Lorimer and Pastan (Nucleic Acids Res. 1995; 23:3067-3068) with some modifications (Xu, H F. et al 2003). A total quantity of 5 mg BSAP IV fragments is randomly fragmented using DNase I for 15 minutes. The digested DNA fragments are visualized as a small smear on a 2% low melting temperature agarose gel. The fragments in specified molecular size ranges are subjected to gel extraction and then eluted with 30 ml elution buffer (10 mM Tris, 1 mM EDTA, pH 8.0). Reassembly of the DNA fragments was conducted by PCR without primers, using the following conditions: 94° C. for 4 minute, then 40 cycles of 94° C. for 50 seconds, 56° C. for 50 seconds, 72° C. for 50 seconds+5 seconds/cycle, followed by a final extension step at 72° C. for 7 minutes. The reassembled DNA is amplified by the following procedure with two flanking primers, and the final PCR products are ligated into pET vector and then transformed into *E. coli* SL21 (DE3).

The screening of mutant libraries is carried out by assessing activity of cell-free medium. The members of the mutant libraries are allowed to grow for 16-18 hours on LB plates with ampicillin and indicator substrate 5-bromo-4-chloro-3-indolyl phosphate, which can be de-phosphorylated by AP resulted in blue colonies. Each active (i.e. blue) colony is then picked and suspended in a unique well of a 96-well plate containing 200 ml of media. The cells are then treated for growth conditions and activity assay. Clones with improved activity are then sequenced.

Example 4: In Vivo Disease Models to Assess Efficacy of AP-Based Agent in Autism Spectrum Disorders An in vivo model was established in order to perform behavioral testing on offspring.

C57BL/6J female mice were divided into treatment groups (Treatment A, B, or C) and fed either regular chow or high fat chow for 8 weeks to induce obesity in the high fat fed group (Table 1). The high fat chow was provided for 8 weeks before breeding, and throughout gestation and nursing.

TABLE 1

Summary of Treatment Groups

| Group | Feed | Treatment |
|---|---|---|
| A | Normal diet | vehicle |
| B | High fat diet | vehicle |
| C | High fat diet | IAP |

From the time of high fat chow feeding, mice in the experimental group received the test article Bovine Intestinal Alkaline Phosphatase II ("SYN BIAPII") at 800 U/ml, administered in the drinking water. Control mice received vehicle water. SYN BIAPII or vehicle administration continued during breeding, throughout gestation, and until weaning.

After 8 weeks of high fat chow feeding, females were mated with normal C57BL/6J mice and impregnated. The diets and compound regimens remained the same until weaning. Within 48 hours of parturition, litters were assessed and offspring gender was determined. Litters were then left undisturbed except for normal husbandry procedures until weaning. Weaning occurred 21 days after parturition.

Figure 5:
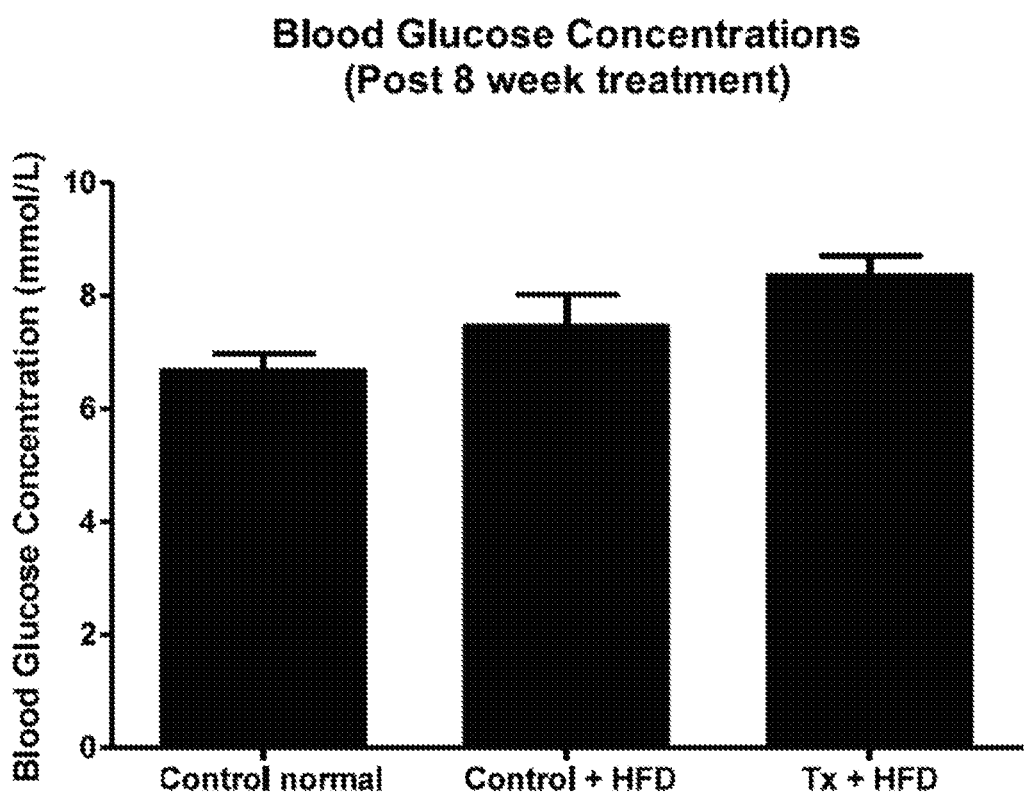
FIG. 5 depicts the blood glucose concentrations as assayed from the various treatment groups after 8 weeks of feeding.

Preliminary results are shown in Table 2. Four dams in the control group (regular chow; Treatment Group A) gave birth to twenty-five pups, total, equally distributed by gender. Six dams that received high fat chow and vehicle (Treatment Group B) gave birth to a total of fifteen newborn pups. Interestingly, as shown in the table, fourteen of these offspring are male and only one is female. In contrast, administration of IAP to six dams fed with the high fat chow (Treatment Group C) resulted in 8 newborn pups, equally distributed by gender, suggesting that IAP administration may play a role in restoring a gender distribution imbalance when subjects ingested a high fat diet.

hours and blood was drawn to assess metabolic syndrome onset and to record blood glucose levels in order to determine whether the presence or absence of treatment had an effect on blood glucose levels. FIG. 5 depicts the results of the blood glucose testing, and as can be seen from the results, there was no statistically significant effect seen in blood glucose concentrations after 8 weeks of feeding, although mice receiving a high fat diet tended to have higher blood glucoses concentrations than mice receiving normal chow. Then the female mice were paired with male C57BL/6J mice (n=6) to breed.

Once mating was confirmed, dams were single housed. Pregnant mice were left undisturbed and remained on the same diet as before until pup assessment post-parturition.

TABLE 2

Preliminary result of offspring from mice fed with a high fat diet

| Purpose | Feed | Treatment | Litter ID | Status of 1st litter | Status of 2nd Litter | Status of 3rd Litter | Notes | ♀ | ♂ |
|---|---|---|---|---|---|---|---|---|---|
| Normal Control | Lab Diets 5001 (Normal diet) | vehicle | 1 | 3 pups (3♀), weaned | 7 Pups (3♀/4♂) | — | | 13 | 12 |
| | | | 2 | 8 pups (3♀/4♂), weaned | Stopped breeding, have reached 12 males | — | | | |
| | | | 3 | 3 pups (2♀/1♂), weaned | Bred again, due week of Dec 18 | — | | | |
| | | | 4 | First litter lost from PND 19-21 (had 2♀/1♂), | 5 Pups (2♀/3♂) | — | | | |
| High fat control | Res Diet D12492 (High fat) | vehicle | 5 | First litter lost | 3 pups (3♂), weaned | — | | 1 | 14 |
| | | | 6 | First litter lost | Second litter lost | — | | | |
| | | | 7 | First litter lost | 1 pup (1♂), weaned | — | | | |
| | | | 8 | First litter lost | 3 pups (3♂) | — | | | |
| | | | 9 | 1 pup (1♂), weaned | 4 Pups (1♀/3♂) | — | | | |
| | | | 10 | First litter lost | 3 pups (3♂), weaned | — | | | |
| High fat + treatment | Res Diet D12492 (High fat) | IAP | 11 | First litter lost | Second litter lost | Re-breeding | | 4 | 4 |
| | | | 12 | First litter lost | 1 pup (1♂), weaned | Re-breeding | | | |
| | | | 13 | First litter lost | Second litter lost | Re- breeding | | | |
| | | | 14 | First litter lost | Second litter lost | Bred again, due week of Jan 8 | | | |
| | | | 15 | 4 pups (2♀/2♂), weaned | 3 Pups (2♀/1♂) | | | | |
| | | | 16 | First litter lost | Re-breeding | | Breeding was confirmed but no litter was born. Re-breeding | | |

Example 5: Studies Assessing Efficacy of AP-Based Agent in Autism Spectrum Disorders The purpose of this example is to assess the efficacy of SYN BIAPII for alleviating maternal diet-induced behavioral deficits in offspring.

An in vivo model was utilized to verify the therapeutic potential of AP-based agents in a maternal autism-like model.

Mice were bred as described in Example 4.

Figure 2:
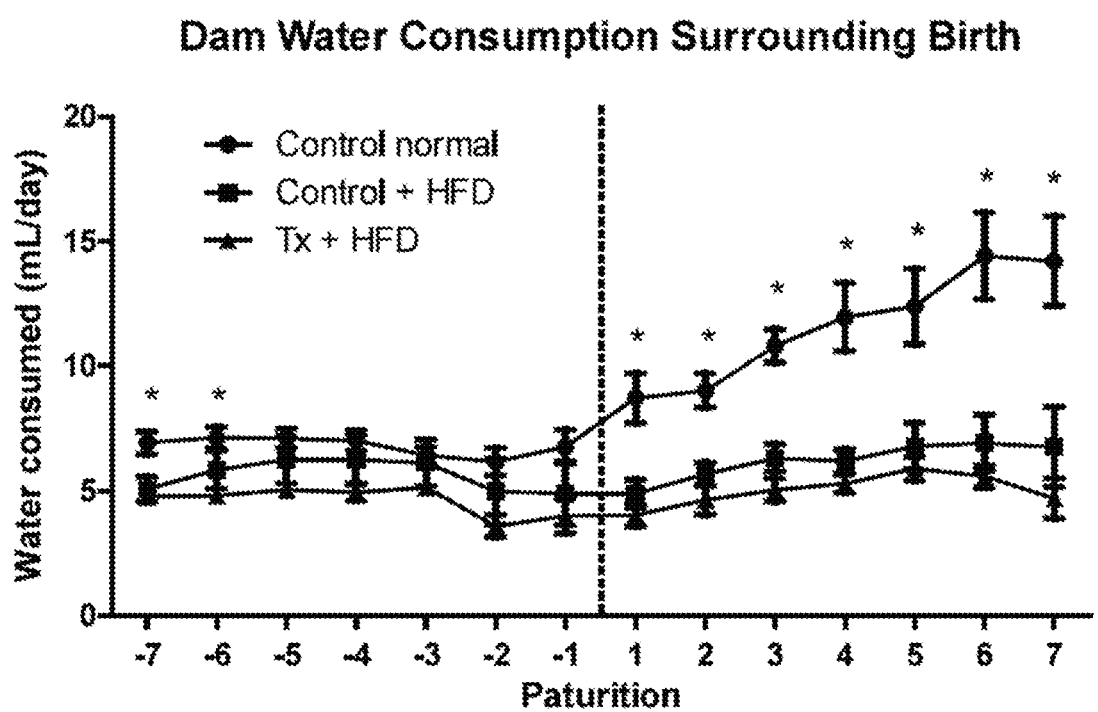
FIG. 2 depicts the water consumption for the 14 days surrounding parturition.
Figure 3:
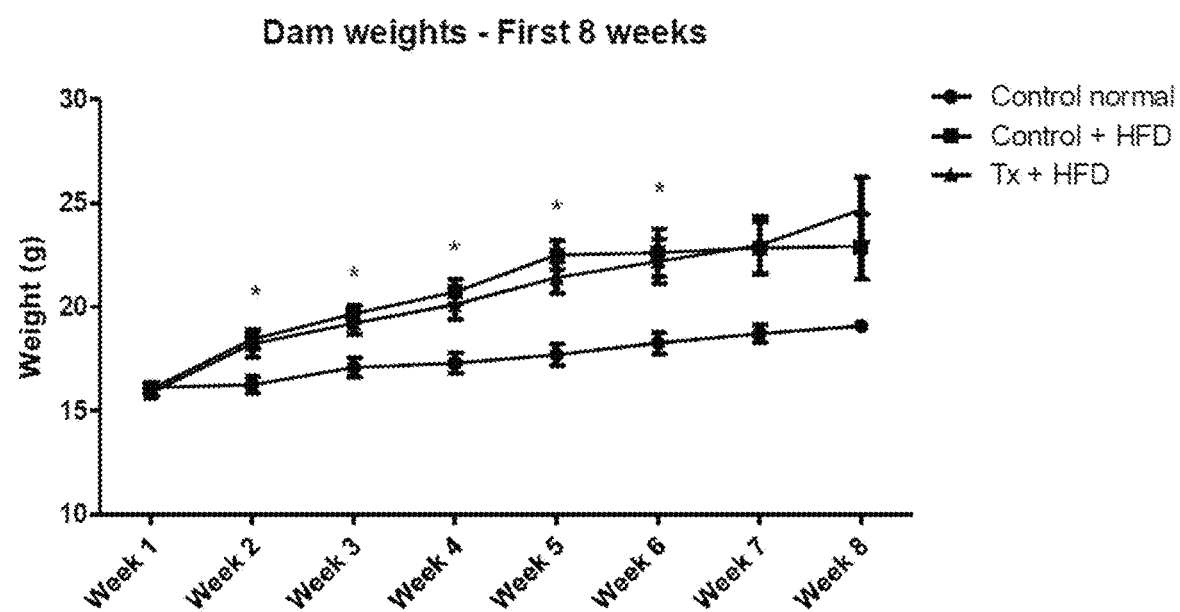
FIG. 3 shows dam weights over the course of the first 8 weeks.
Figure 4:
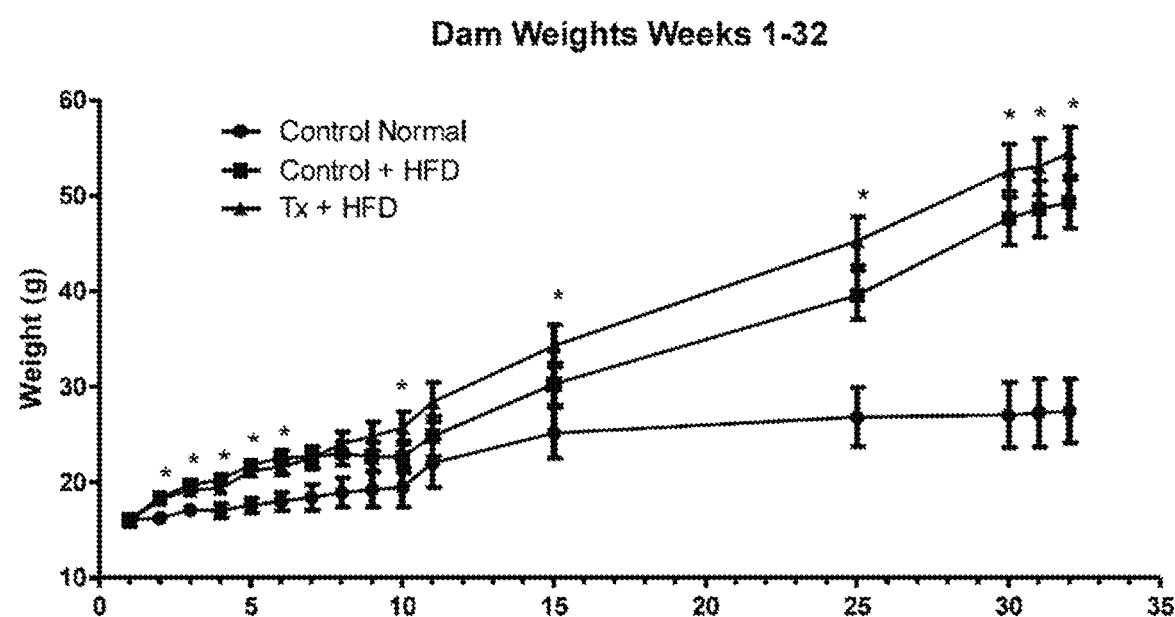
FIG. 4 shows dam weights over the course of 32 weeks.

Sixteen female C57BL/6J mice were assigned to one of three treatment groups: (1) regular diet with regular water (n=4); (2) high fat diet (HFD) with regular water (n=6); and (3) high fat diet with water dosed with 800 U/mL SYN BIAPII (n=6). Water consumption was measured daily, and the mean water consumption over the first 8 weeks is depicted in FIG. 1. The water consumption for the 14 days surrounding parturition is displayed in FIG. 2. Females were weighed 24 hours after arrival, and then once per week thereafter until parturition. FIG. 3 depicts dam weights over the course of the first 8 weeks, and FIG. 4 shows dam weights over the course of 32 weeks. After a minimum of 8 weeks on a diet, the female mice were fasted for about 4

Figure 6:
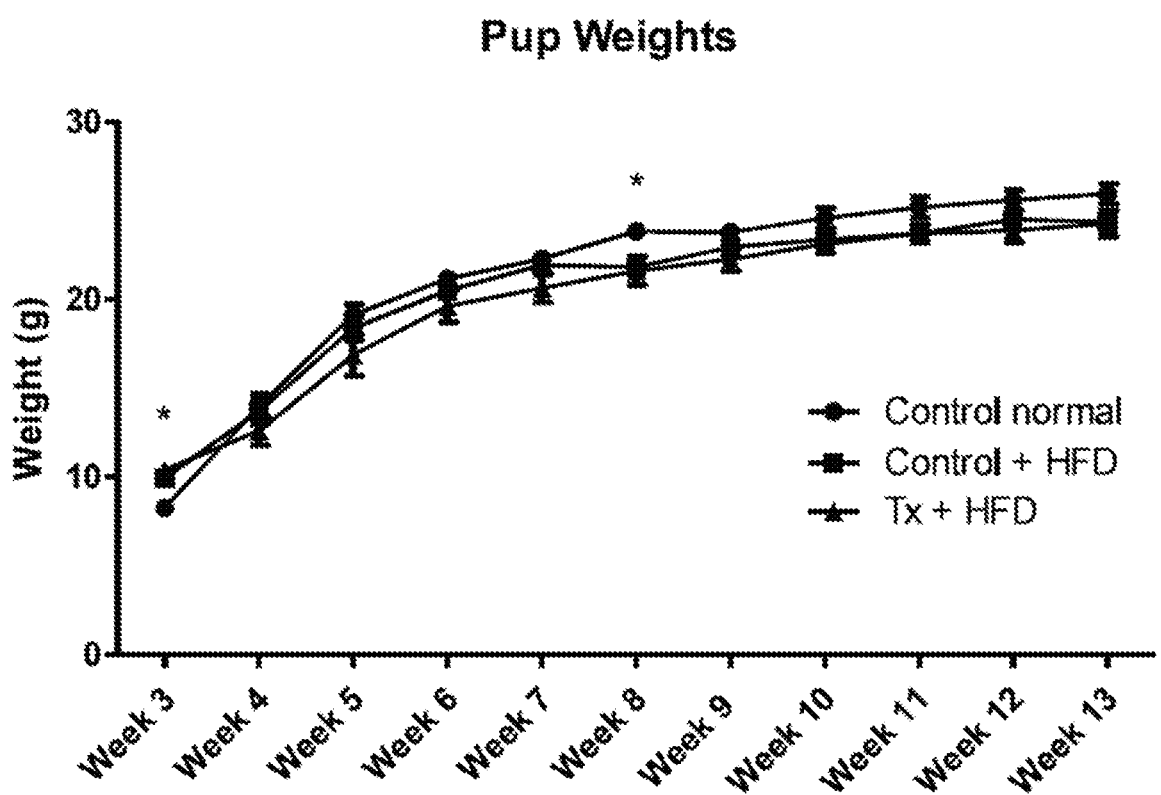
FIG. 6 depicts the weekly weights of mouse pups from each of the various treatment groups after having been weaned between post-natal day 20-22.

Within 3-5 days of parturition, all litters were assessed, and the number of males and females was determined. The pups were weaned between post-natal day 20-22, at which time they were weighed weekly (results depicted in FIG. 6), sorted into new cages by sex and treatment group, and ear notched for tracking purposes. All pups were provided standard rodent chow and had access to regular water.

Male offspring from the aforementioned litters of C57BL/6J mice were utilized for these studies. There was a maximum of 12 mice per treatment for behavioral testing. Behavioral testing was performed on weaned male offspring at between postnatal 7-12 weeks of age. Up to twelve offspring per treatment underwent a series of behavioral tests to determine if behavioral differences exist between treatment groups. Behavioral testing was undertaken by evaluating one or more of reciprocal social interaction test, three-chamber paradigm test (e.g. Crawley's sociability and preference for social novelty protocol), marble burying assay, and activity in an open field (e.g. locomotion). All offspring underwent the tests in the same order and within the same postnatal week of age.

Three-Chamber Social Interaction Test

The purpose of the three-chamber social interaction test, among other things, is to assess sociability and preference for novelty. Phase 1 of the Three-Chamber Social Interaction Test allows for baseline evaluation to determine if a bias for chamber preference is pre-existing. Phase 2 presentation provides an indication of "sociability" as a normal mouse will tend to spend more time in the same room and interacting with the novel rodent rather than the novel inanimate object. Phase 3 presentation is indicative of social novelty seeking behaviors; normal rodents will typically prefer to spend more time in the same room as and interacting with the novel rodent. Preference for social novelty also contains components of social recognition and social memory, so is useful for investigation of these types of measures as well.

The Three-Chamber test was administered during postnatal weeks 8-10. This test arena consisted of three equally sized rooms (20×45 cm each), divided by clear Plexiglas, and with an access door between each compartment. The test occurred in three distinct stages; (1) Acclimatization phase (baseline): The test animal was placed in the center compartment (zone) and allowed to freely explore the entire (empty) maze for 10 minutes; (2) Sociability phase (novel mouse vs novel object vs center): A "stranger" (an unfamiliar male mouse) was contained within a wire mesh container in an outer chamber of the maze and an identical container (clean and empty) was placed in the chamber at the opposite side of the arena (position of "stranger" and "novel object" was counterbalanced between trials); and (3) Social novelty phase (familiar mouse vs novel mouse vs center): A new unknown "stranger" was placed into the "novel object" compartment, thus providing the test animal with a choice between spending time with a now familiar animal, or a new (novel) animal. The test mouse was returned to its holding cage between each test phase (intertrial interval; 2 minutes). Phase 1 was used as a baseline to ensure there was no potential confound from initial preference for one chamber over the other. Measurements during Phase 2 and 3 included number of entries and time spent in each chamber as well as number and time spent directly interacting with each mouse (familiar or stranger) or the object.

Figure 7:
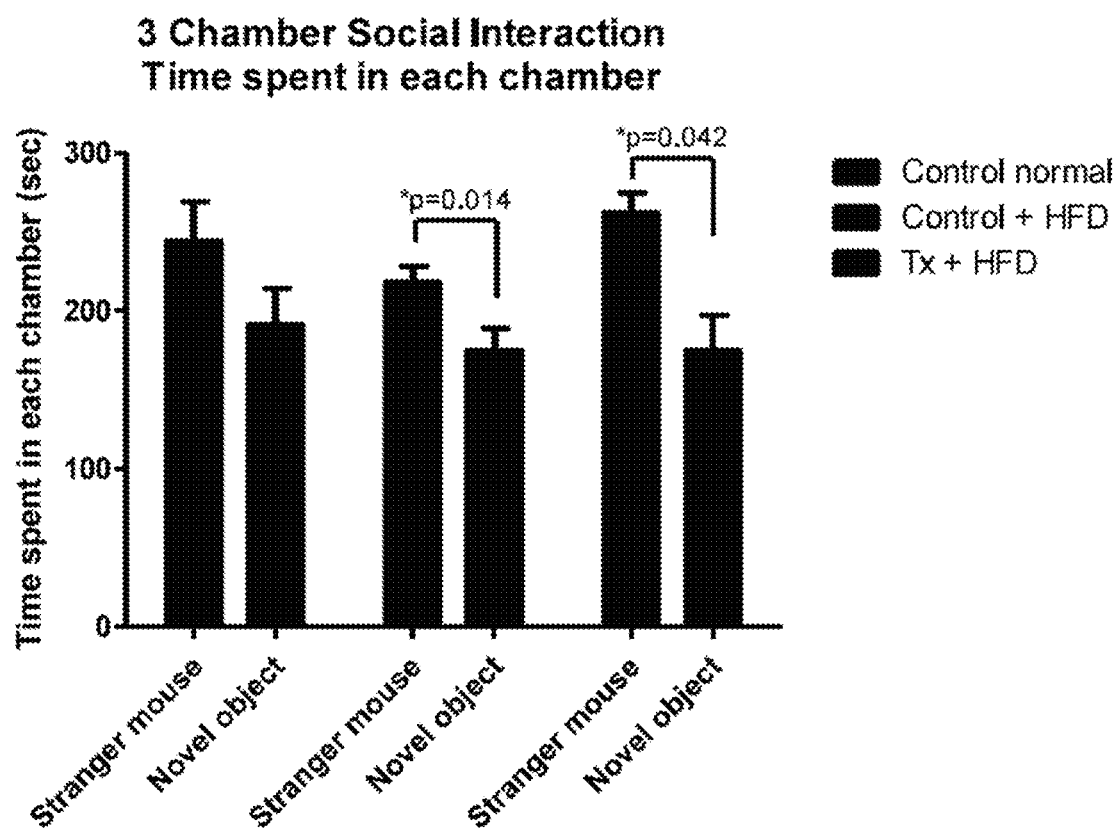
FIG. 7 depicts time (in seconds) that each of the various treatment groups spent in each chamber containing either a stranger mouse or a novel object during the three-chamber social interaction test. The control normal group was fed normal chow with vehicle water; the control+HFD group was fed a high fat diet (HFD) with vehicle water; and the Tx+HFD group was fed a high fat diet with water containing SYN BIAPII. The histogram shows the control normal group in the leftmost two bars, the control+HFD group in the middle two bars, and the Tx+HFD group in the rightmost two bars.
Figure 8:
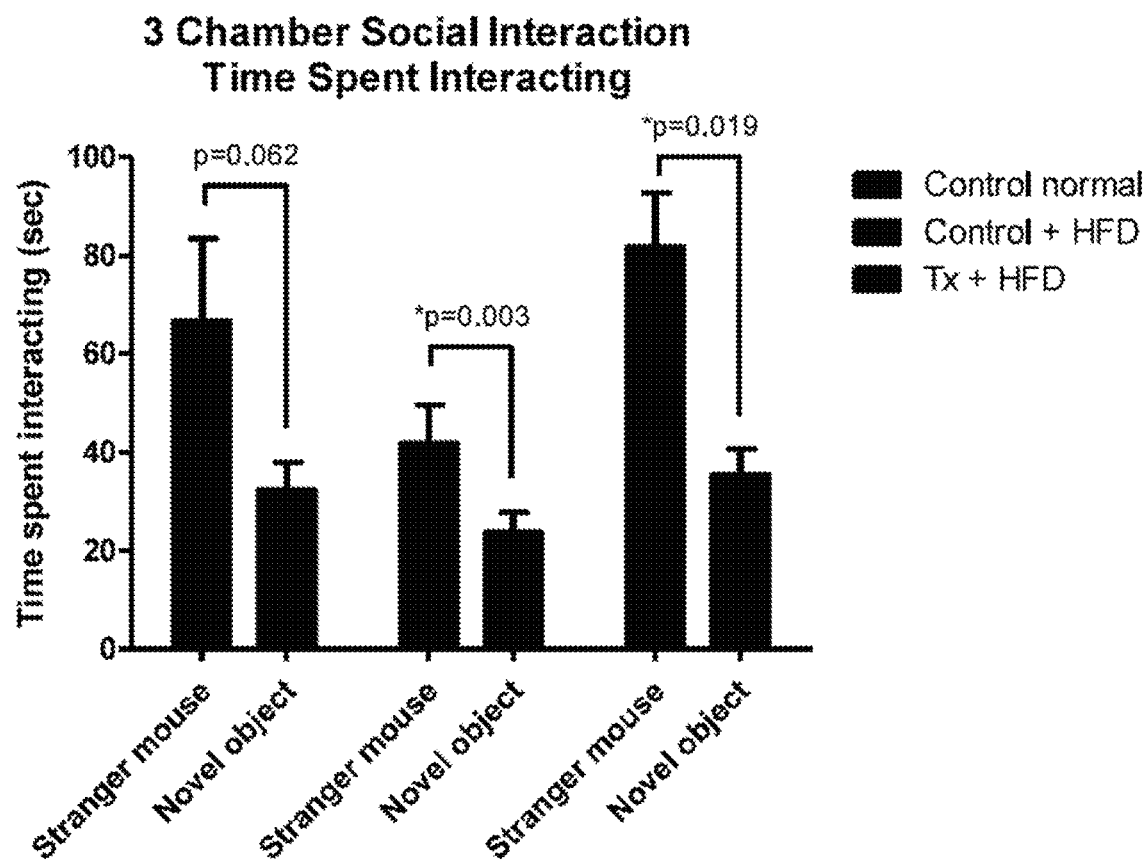
FIG. 8 depicts time (in seconds) that each of the various treatment groups spent interacting with the stranger mouse or novel object in each chamber during the three-chamber social interaction test. The control normal group was fed normal chow with vehicle water; the control+HFD group was fed a high fat diet (HFD) with vehicle water; and the Tx +HFD group was fed a high fat diet with water containing SYN BIAPII. The histogram shows the control normal group in the leftmost two bars, the control+HFD group in the middle two bars, and the Tx+HFD group in the rightmost two bars.
Figure 9:
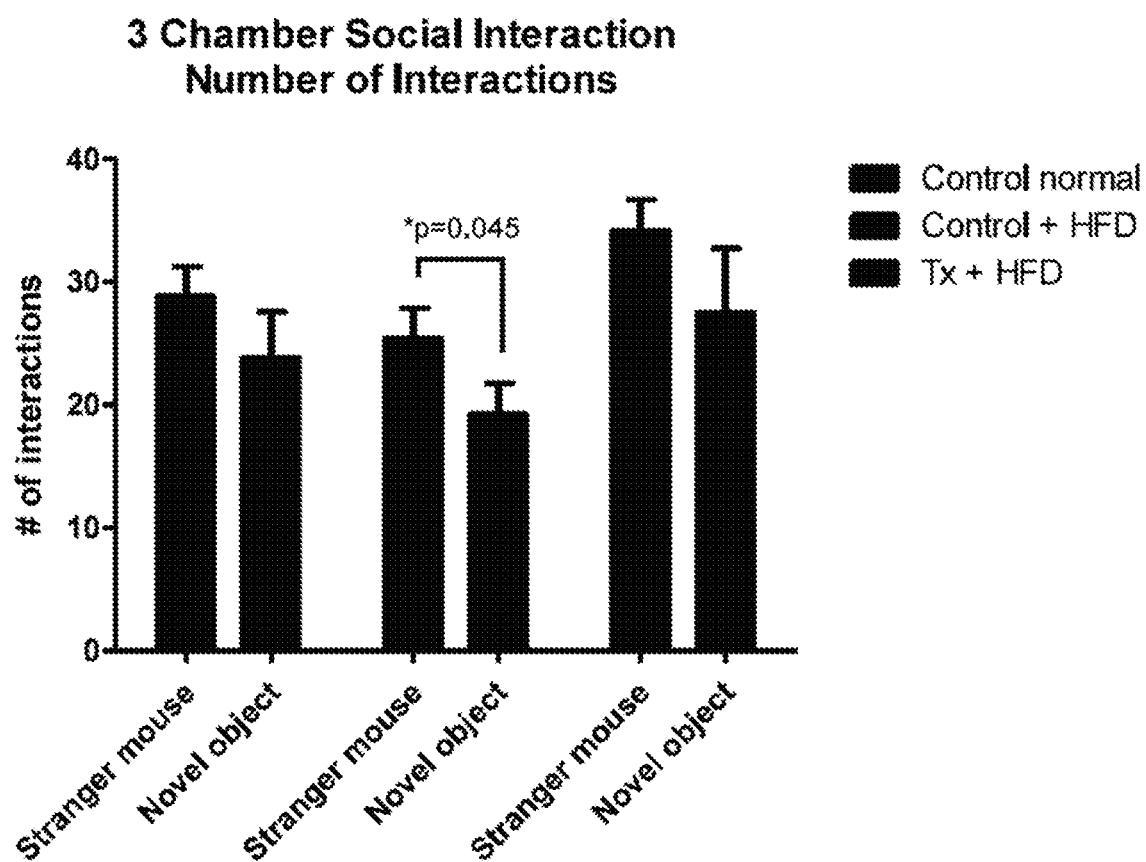
FIG. 9 depicts the number of interactions that each of the various treatment groups had with either the stranger mouse or novel object in each chamber during the three-chamber social interaction test. The control normal group was fed normal chow with vehicle water; the control+HFD group was fed a high fat diet (HFD) with vehicle water; and the Tx+HFD group was fed a high fat diet with water containing SYN BIAPII. The histogram shows the control normal group in the leftmost two bars, the control+HFD group in the middle two bars, and the Tx+HFD group in the rightmost two bars.

The results of the three-chamber interaction test showed that an evaluation of baseline exploration revealed no bias for left or right chambers within any treatment groups. During the sociability phase, there were no between-group differences in time spent or number of entries into any of the 3 chambers (stranger mouse, novel object, or center; p>0.05). However, all groups did show a preference for interacting with the stranger mouse as compared to the novel object across a number of measures. In this study, Tx refers to the test article SYN BIAPII. Control+HFD mice (p=0.014, paired samples t-test) and Tx+HFD mice (p=0.042, paired samples t-test) spent significantly more time in the chamber containing the stranger mouse vs the chamber containing the novel object (FIG. 7). In addition, the Control+HFD group (p=0.003, paired samples t-test) and the Tx+HFD group (p=0.019, paired samples t-test) spent significantly more time interacting with the stranger mouse vs the novel object (FIG. 8), and Control+HFD mice also showed an increased number of interactions with the stranger mouse as compared to the novel object (p=0.045, paired samples t-test) (FIG. 9).

Figure 10:
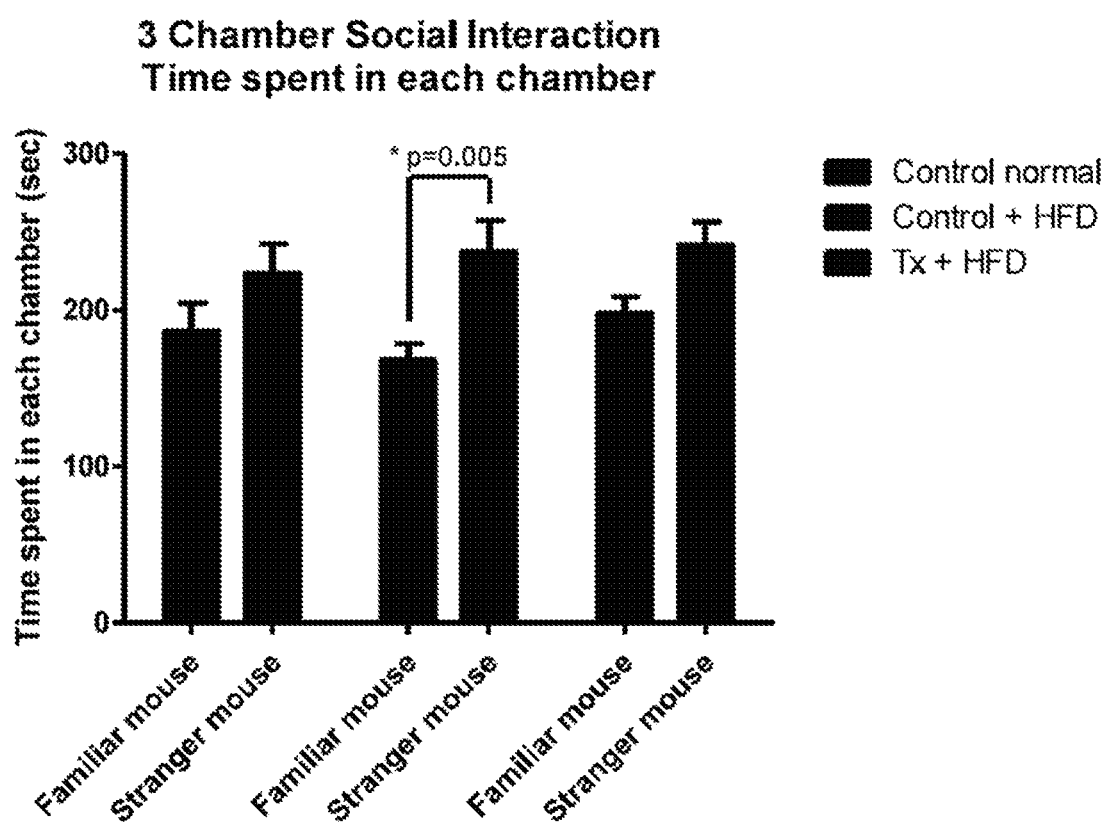
FIG. 10 depicts time (in seconds) that each of the various treatment groups spent in each chamber containing either a familiar mouse or a stranger mouse during the three-chamber social interaction test. The control normal group was fed normal chow with vehicle water; the control+HFD group was fed a high fat diet (HFD) with vehicle water; and the Tx+HFD group was fed a high fat diet with water containing SYN BIAPII. The histogram shows the control normal group in the leftmost two bars, the control+HFD group in the middle two bars, and the Tx+HFD group in the rightmost two bars.
Figure 11:
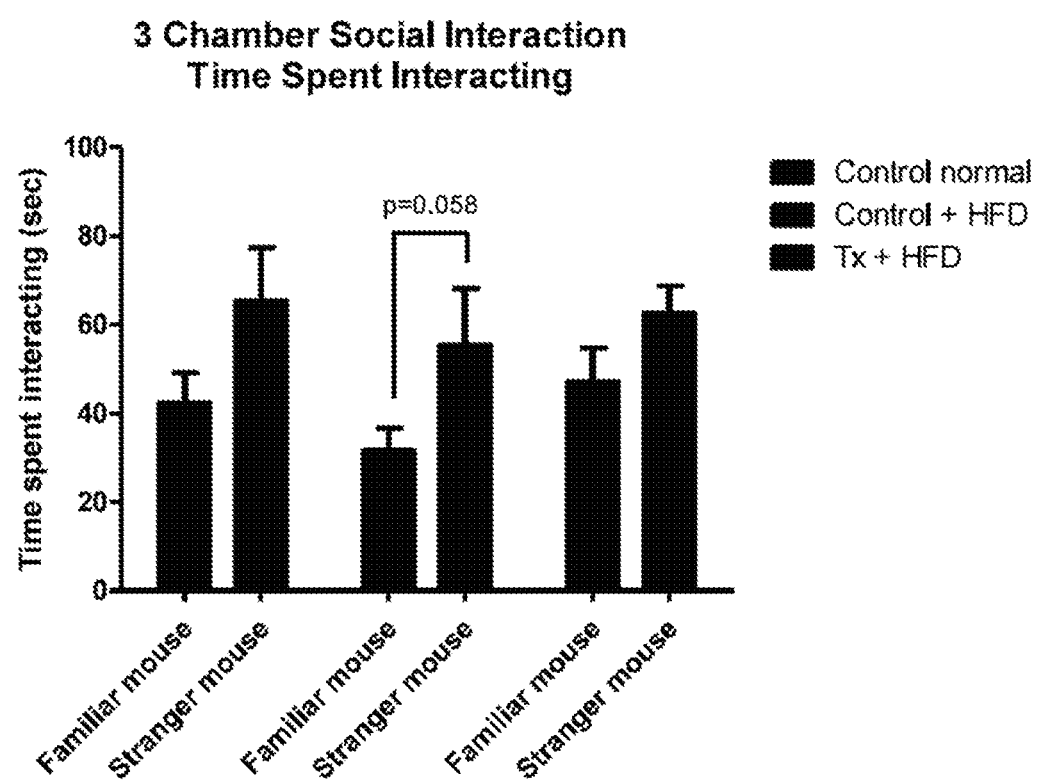
FIG. 11 depicts time (in seconds) that each of the various treatment groups spent interacting with the familiar mouse or stranger mouse in each chamber during the three-chamber social interaction test. The control normal group was fed normal chow with vehicle water; the control+HFD group was fed a high fat diet (HFD) with vehicle water; and the Tx+HFD group was fed a high fat diet with water containing SYN BIAPII. The histogram shows the control normal group in the leftmost two bars, the control+HFD group in the middle two bars, and the Tx+HFD group in the rightmost two bars.
Figure 12:
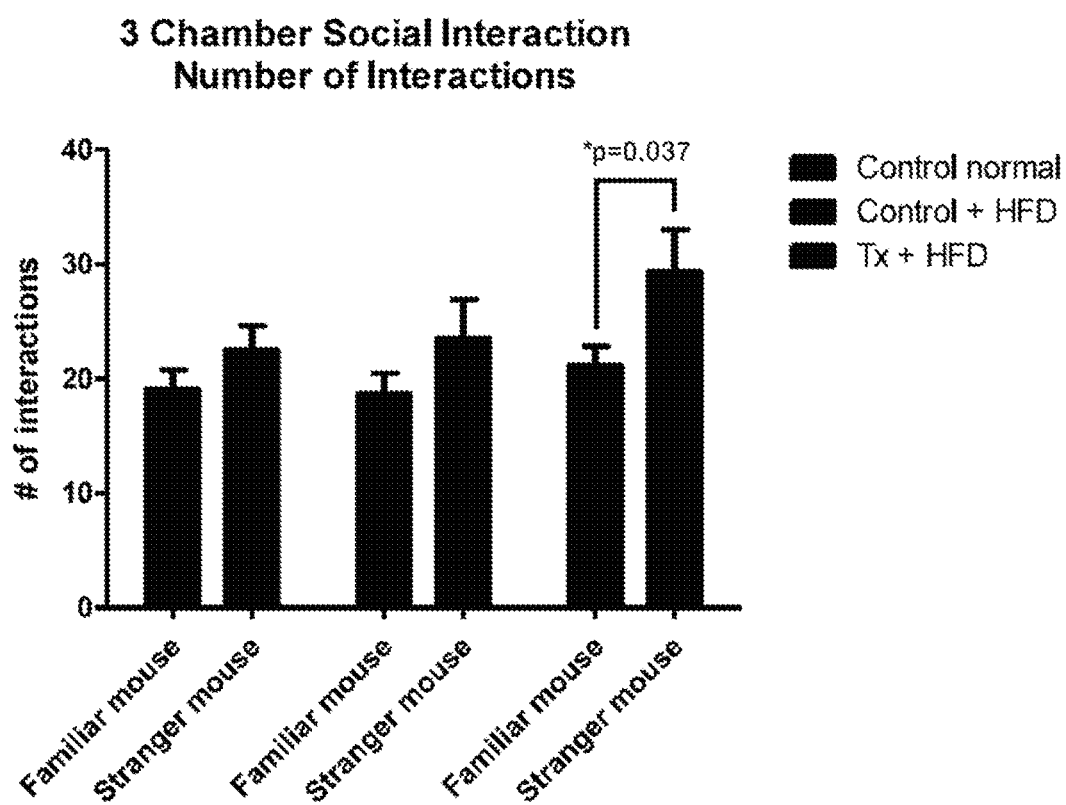
FIG. 12 depicts the number of interactions that each of the various treatment groups had with either the familiar mouse or the stranger mouse in each chamber during the three-chamber social interaction test. The control normal group was fed normal chow with vehicle water; the control+HFD group was fed a high fat diet (HFD) with vehicle water; and the Tx+HFD group was fed a high fat diet with water containing SYN BIAPII. The histogram shows the control normal group in the leftmost two bars, the control+HFD group in the middle two bars, and the Tx+HFD group in the rightmost two bars.
Figure 13:
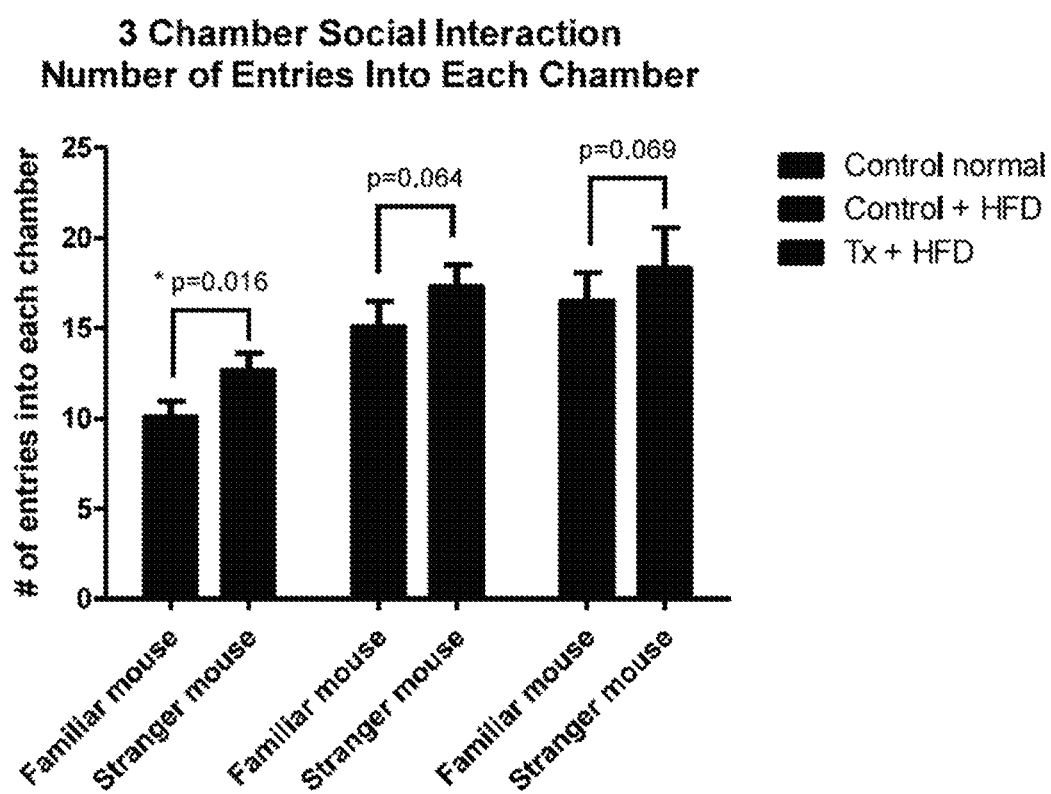
FIG. 13 depicts the number of entries into each chamber containing either the familiar mouse or the stranger mouse of each of the various treatment groups during the three-chamber social interaction test. The control normal group was fed normal chow with vehicle water; the control+HFD group was fed a high fat diet (HFD) with vehicle water; and the Tx+HFD group was fed a high fat diet with water containing SYN BIAPII. The histogram shows the control normal group in the leftmost two bars, the control+HFD group in the middle two bars, and the Tx+HFD group in the rightmost two bars.

In the social novelty phase, the Control+HFD group spent significantly more time in the chamber containing the new stranger mouse compared to the chamber containing the familiar mouse (p=0.005, paired samples t-test; FIG. 10), and tended toward a greater time spent interacting with the new stranger mouse compared to the familiar mouse (p=0.058, paired samples t-test; FIG. 11). As in the sociability phase, Tx+HFD mice appeared to perform more similarly to controls for these measures, with the exception of the number of interactions, where Tx+HFD group displayed a significantly increased number of interactions with the stranger mouse compared to the familiar mouse (p=0.037, paired samples t-test; FIG. 12). All mice showed a trend toward more entries into the chamber containing the stranger mouse; this was statistically significant in the Normal Control group (p=0.016, paired samples t-test; FIG. 13).

Figure 14:
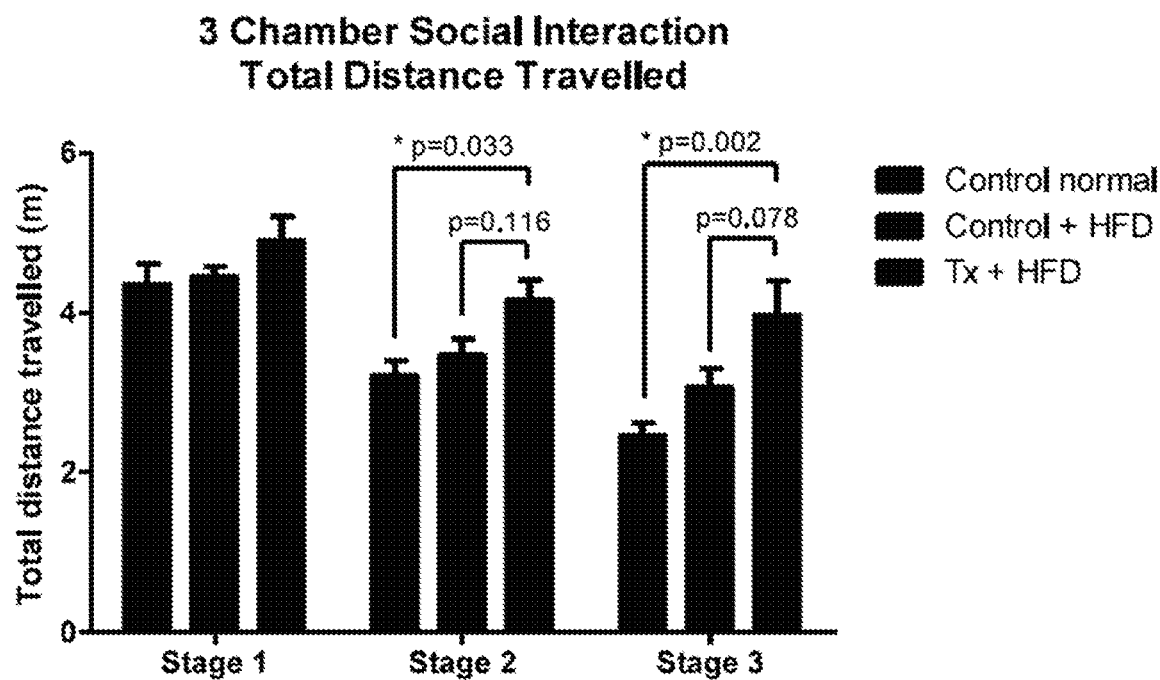
FIG. 14 depicts the total distance travelled throughout testing of each of the various treatment groups during stages 1-3 of the three-chamber social interaction test. The control normal group was fed normal chow with vehicle water; the control+HFD group was fed a high fat diet (HFD) with vehicle water; and the Tx+HFD group was fed a high fat diet with water containing SYN BIAPII. Each set of histograms (according to Stage 1, Stage 2, or Stage 3) shows the control normal group in the leftmost bar, the control+HFD group in the middle bar, and the Tx+HFD group in the rightmost bar.

An analysis of total distance travelled throughout testing was conducted (FIG. 14). There were no significant differences between groups in distance travelled during baseline testing (Stage 1) while the arena was empty. However, during sociability testing (Stage 2), there was a statistically significant main effect (p=0.040, one way ANOVA), with the Tx+HFD group moving more than Normal Controls (p=0.033, Tukey's post hoc). In addition, a trend was also seen for this measure between Tx+HFD and Control+HFD groups (p=0.116, Tukey's post hoc). This same effect was noted during social novelty testing (Stage 3) as well, where a main affect was also found (p=0.004, one-way ANOVA). The Tx+HFD group moved a statistically significantly greater distance as compared to the Normal Controls (p=0.002, Tukey's post hoc) and showed a tendency toward moving a greater distance than the Control+HFD group (p=0.078).

Overall, the results showed that the HFD-derived offspring seemed to interact less with other mice, while the IAP-derived offspring behaved similarly to controls, which suggests that administration of IAP reduces the social deficits compared to no treatment.

Reciprocal Social Interaction

The purpose of the reciprocal social interaction test is to assess overall sociability and complex social measures.

Dyadic testing was performed during postnatal weeks 10-12. Mice were simultaneously placed in an open, unfamiliar arena (25×25 cm) with either a familiar cage-mate, or an unfamiliar partner (with the order of testing counterbalanced across all groups). In all cases, pairs were from the same treatment group. Mice were allowed to interact freely for 5 minutes. Latency to first interaction, number of and time spent in bidirectional interactions (e.g. nose-to-nose sniffing), and total time spent interacting was quantified. Interaction was defined as any of the following: bidirectional encounters, close following, touching partner, allogrooming, nose-to-anus sniffing, and crawling over/under.

Figure 15:
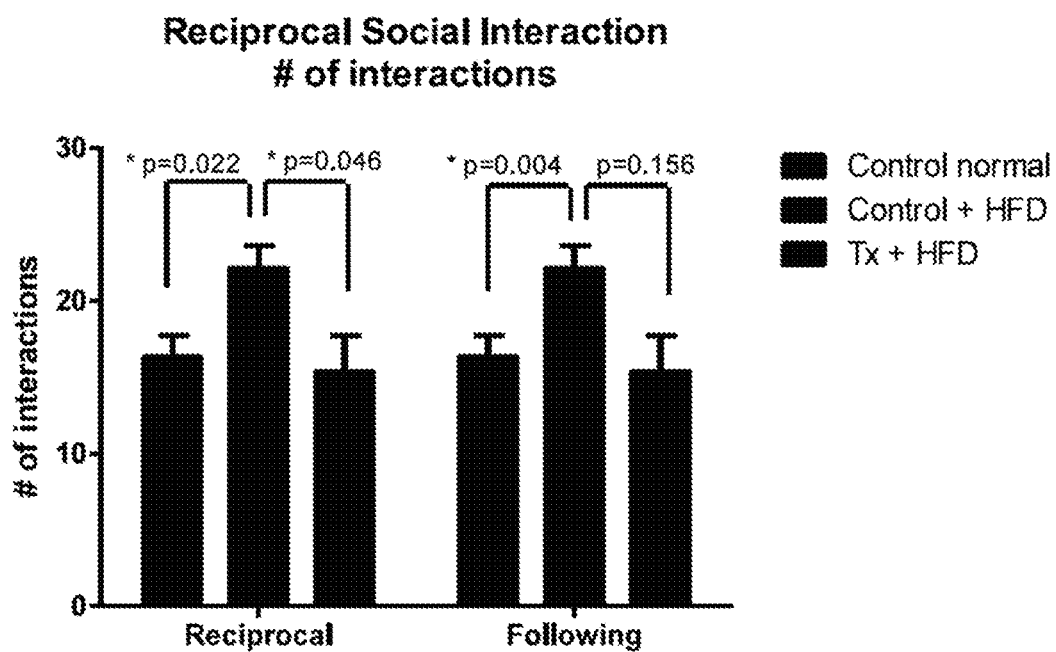
FIG. 15 depicts the number of interactions, either reciprocal or following, during a reciprocal social interaction test for each of the various treatment groups. The control normal group was fed normal chow with vehicle water; the control+HFD group was fed a high fat diet (HFD) with vehicle water; and the Tx+HFD group was fed a high fat diet with water containing SYN BIAPII. Each set of histograms (according to Reciprocal or Following) shows the control normal group in the leftmost bar, the control+HFD group in the middle bar, and the Tx+HFD group in the rightmost bar.

As depicted by FIG. 15, an analysis of the number of reciprocal social interactions (head-to-head interacting) revealed a significant main effect for treatment group (p=0.011, one-way ANOVA), with post-hoc testing showing the Control+HFD group animal performing a greater number of these interactions as compared to both the Normal Control group (p=0.022, Tukey's post hoc) and Tx+HFD group (p=0.046, Tukey's post hoc). Similarly, the number of following interactions (nose-to-tail interacting) was also increased in this group (main effect p=0.005, one-way ANOVA) with post-hoc testing showing a difference between the Control+HFD group and Normal Controls (p=0.004, Tukey's post hoc), but not from Tx+HFD mice (p=0.156, Tukey's post hoc).

Figure 16:
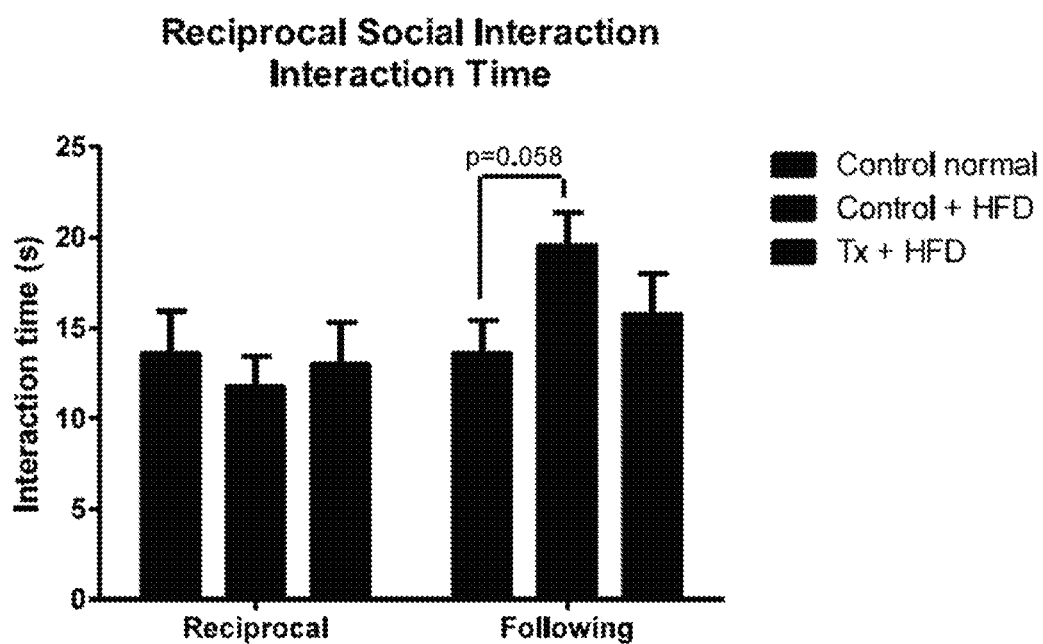
FIG. 16 depicts the time (in seconds) of the interactions, either reciprocal or following, during a reciprocal social interaction test for each of the various treatment groups. The control normal group was fed normal chow with vehicle water; the control+HFD group was fed a high fat diet (HFD) with vehicle water; and the Tx+HFD group was fed a high fat diet with water containing SYN BIAPII. Each set of histograms (according to Reciprocal or Following) shows the control normal group in the leftmost bar, the control+HFD group in the middle bar, and the Tx+HFD group in the rightmost bar.

An analysis of total time spent interacting in reciprocal behavior (head-to-head interacting) showed no between-group differences, although following behavior (nose-to-tail interacting) did reveal a trend toward an increase in following for the Control+HFD group compared to Normal Controls (p=0.058, Tukey's post hoc; FIG. 16).

Figure 17:
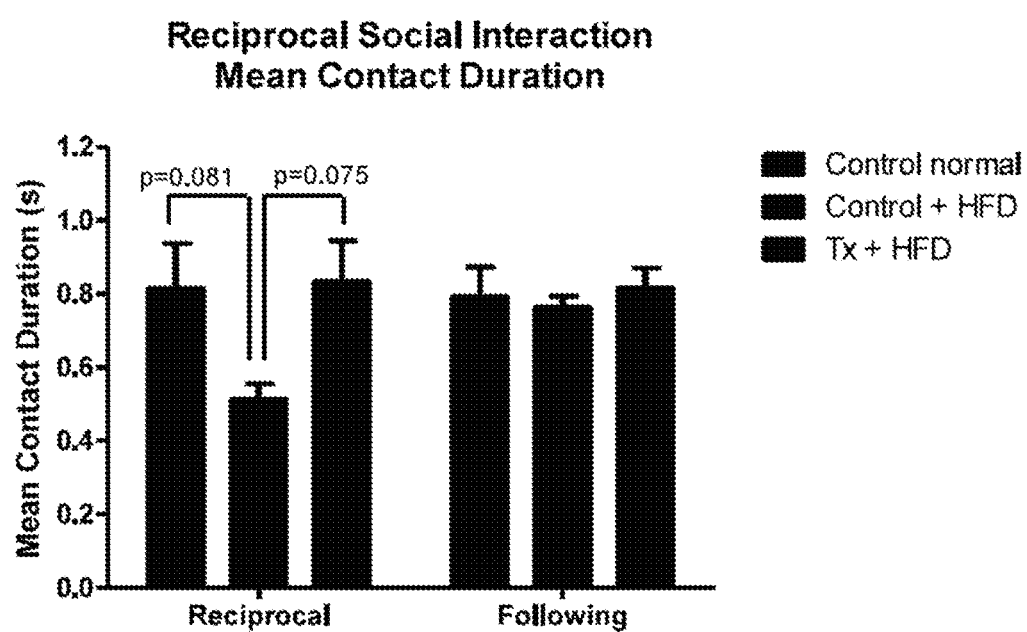
FIG. 17 depicts the mean contact duration time (in seconds) of the interactions, either reciprocal or following, during a reciprocal social interaction test for each of the various treatment groups. The control normal group was fed normal chow with vehicle water; the control+HFD group was fed a high fat diet (HFD) with vehicle water; and the Tx+HFD group was fed a high fat diet with water containing SYN BIAPII. Each set of histograms (according to Reciprocal or Following) shows the control normal group in the leftmost bar, the control+HFD group in the middle bar, and the Tx+HFD group in the rightmost bar.

As shown in FIG. 17, an analysis of the mean duration of each reciprocal (head-to-head) interaction revealed a statistically significant main effect for treatment group (p=0.022, one-way ANOVA, Welch correction). While post hoc analyses did not show any statistically significant differences between groups, there was a trend towards a decreased contact duration for Control+HFD mice compared to both the Normal Control group (p=0.081, Games-Howell post hoc) and Tx+HFD group (p=0.075, Games-Howell post hoc). No differences were observed between groups for mean contact duration for following (head-to-tail). Overall, the results suggest that IAP-derived mice behave more like the control group than HFD-derived mice, which exhibited a lack of interaction.

Figure 18:
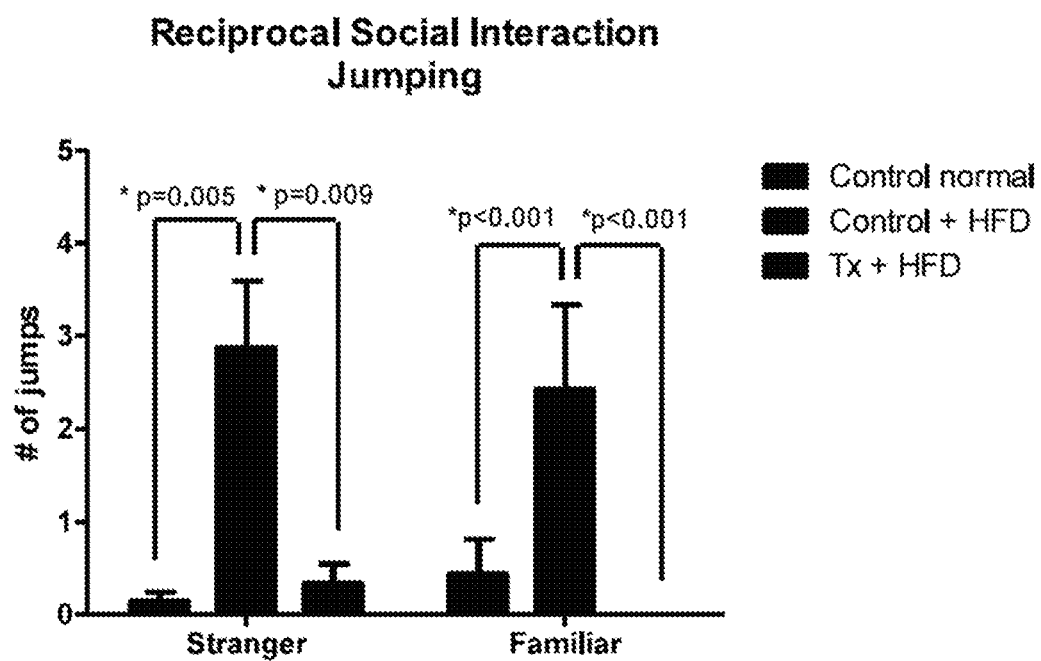
FIG. 18 depicts the number of jumps exhibited by subjects during dyadic testing in each of the various treatment groups. The control normal group was fed normal chow with vehicle water; the control+HFD group was fed a high fat diet (HFD) with vehicle water; and the Tx+HFD group was fed a high fat diet with water containing SYN BIAPII. Each set of histograms (according to Stranger or Familiar) shows the control normal group in the leftmost bar, the control+HFD group in the middle bar, and the Tx+HFD group in the rightmost bar.

In addition to social measures during reciprocal social interaction testing, jumping behaviors were also quantified when it was noted that some mice were repeatedly and persistently jumping in the test arena. As shown in FIG. 18, a main effect for treatment group was found for total number of jumps during testing with a stranger mouse (p=0.009, one-way ANOVA, Welch correction), with the Control+HFD group jumping more than both the Normal Control group (p=0.005, Games-Howell post-hoc) and the Tx+HFD group (p=0.009, Games-Howell post hoc). This effect was also observed when these mice were tested with a familiar cage mate. However, as no Tx+HFD mice jumped during this testing phase, analysis using ANOVA was not possible. Instead, t-tests were run to look for group differences, and revealed that the Control+HFD group jumped more than both the Normal Control group (p<0.001, independent samples t-test) and Tx+HFD group (p<0.001, independent samples t-test).

Overall conclusions from these behavioral studies show that offspring from high fat diet (HFD) SYN BIAPII litters performed more similarly to normal controls in reciprocal interaction testing and three-chamber tests. This suggests that treatment with SYN BIAPII appears to ameliorate some of the social deficits noted in offspring as a consequence of maternal high fat diet.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50%" covers the range of 45% to 55%.

An "effective amount," when used in connection with medical uses is an amount that is effective for providing a measurable treatment, prevention, or reduction in the rate of pathogenesis of a disorder of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents (e.g., additional therapeutic agents described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (a g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures, tissue samples, tissue homogenates or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays or measurements or methane production in stool samples. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

REFERENCES

Alam, S N, Yammine, H, Moaven, O, Ahmed, R., Moss, A K, Biswas, B, Muhammad, N, Biswas, R, Raychowdhury, A, Kaliannan, K, Ghosh, S, Ray, M, Hamarneh, S, Barua, S, Malo, N S, Bhan, A K, Malo, MS<Hodin, R A. (2014). Intestinal alkaline phosphatase prevents ahntbiotic-induced susceptibility to enteric pathogens. Ann Surg. 259:715-722.

Aldag, I, Bockau, U, Rossdorf, J, Laarmann, S, Raaben, W, Hermann, L, Weide, T, Hartman M W W. (2011). Expression, secretion and surface display of a human alkaline phosphatase by the ciliate *Tetrahymena thermophilia*. BMC Biotechnology 11:11.

Barreera, D J, Rosenberg, J N, Chiu, J G, Chang, Y-N, Debatis, M, Ngoi, S-M, Chang, J T, Shoemaker, C B, Oyler, G A, Mayfield, S P. (2014). Algal chloroplast produced camelid VhH antitoxins are capable of neutralizing botulinum neurotoxin. Plant Biotechnology J. doi:10.1111/pbi.12244.

Becerra-Arteaga, A, Mason, H S<Shuler, M L. (2006). Production, secretion, and stability of human secreted alkaline phosphatase in tobacco NT1 cell suspension cultures. Biotechnol. Prog. 22:1643-1649.

Beck, R, Burtscher, H. (1994). Expression of human placental alkaline phosphatase in *Escherichia coli*. Protein Expr. Purif. 5:192-197.

Berger, J, Howard, A D, Gerger, L, Cullen, B R, Udenfriend, S. (1987). Expression of active, membrane-bound human placental alkaline phosphatase by transfected simian cells. Proc. Natl. Acad. Sci USA 84:4885-4889.

Bretthauer, R K, Castellino, F J. (1999). Glycosylation of *Pichia pastoris*-derived proteins. Biotechnol. Appl. Biochem. 30:193-200.

Broz, A, Huang, N, Unruh, G. (2013). Plant-based protein biomanufacturing. www.genengnews.com/gen-articles/plant-based-protein-biomanufacturing/4734/

Buffington S A, Di Prisco G V, Auchtung T A, Ajami N J, Petrosino J F, Costa-Mattioli M. Microbial Reconstitution Reverses Maternal Diet-Induced Social and Synaptic Deficits in Offspring. Cell, 2016; 165(7): 1762-75.

Chen, K T., Malo, M S., Moss, A K., Zeller, S., Johnson, P., Ebrahimi, F., Mostafa, G., Alam, S N., Ramasamy, S., Warren, H S., Hohmann, E L., Hodin, R A. (2010) Identification of specific targets for the gut mucosal defense factor intestinal alkaline phosphatase. Am J Physiol Gastrointest Liver Physiol 299, G467-G475.

Edwards-Ingram, L, Gitsham, P, Burton, N, Warhurst, g, Clarke, I, Hoyle, D, Oliver, S G, Stateva, L. (2007). Genotypic and physiological characterization of Saccharomyces boulardii, the probiotic strain of Saccharomyces cerevisiae. Appl. Environ. Microbiol. 73:2458.

Flagfeldt, D B, Siewers, V, Huang, L, Nielsen, J. (2009). Characterization of chromosomal integration sites for heterologous gene expression in Saccharomyces cerevisiae. Yeast 26:545.

Gomord, V Faye, L. (2004). Posttranslational modification of therapeutic proteins in plants. Curr. Opin. Plant Biol. 7:171-181

Gould T D, Dao D T, Kovacsics C E. The open field test: Mood and anxiety-related behaviours in mice. Neuromethods, 2009; Humana Press: 1-20.

Graff, S, Chaumeil, J-C, Boy, P, Lai-Kuen, R, Charrueau, C. (2008). Influence of pH conditions on the viability of Saccharomyces boulardii yeast. J. Gen. Appl. Microbiol. 54:221-227.

Gregory, J A, Topol, A B, Doerner, D Z, Mayfield, S. (2013). Alga-produced cholera toxin-Pfs25 fusion proteins as oral vaccines. Appl. Environ. Microbiol. 79:3917-3925.

Hatoum R, Labrie, St, Fliss, I. (2012). Antimicrobial and probiotic properties of yeasts: from fundamental to novel applications. Frontiers in Microbiology 3: 421-421.

Heimo, H K, Palmu, K, Suominen, I. (1998). Human placental alkaline phosphatase: expression in *Pichia pastoris*, purification and characterization of the enzyme. Protein Expr. Purif. 12:85-92.

Kaliannana, K., Hamarneha, S R., Economopoulosa, K P., Alama, S N., Moavena, 0., Patela, P., Maloa, N S., Raya, M., Abtahia, S M., Muhammada, N., Raychowdhurya, A., Teshagera, A., Mohameda, M M R., Mossa, A K., Ahmeda, R., Hakimiana, S., Narisawab, S., Milián, J L., Hohmannc, E., Warrenc, H S., Bhand, A K., Maloa, M S., Hodina, R A. (2013) Intestinal alkaline phosphatase prevents metabolic syndrome in mice. PNAS 7003-7008.

Klein, S M, Elmer, G W, McFarland, L V, Surawicz, C M, Levy, R H. (1993). Recovery and elimination of the biotehrapeutic agent, Saccharomyces boulardii, in healthy human volunteers. Pharm Res. 10:1615-1619.

Komarnytsky, S., Borisjuk, N V, Borisjuk, L G., Alam, M Z, Raskin, I. (2000). Production of recombinant proteins in tobacco guttation fluid. Plant Physiol. 124:927-933.

Le Du, M-H., Lamoure, C., Muller, B-H., Bulgakov, O V., Lajeunesse, E., Menez, A., Boulain, J-C. Artificial evolution of an enzyme active site: structural studies of three highly active mutants of *Escherichia coli* alkaline phosphatase (2002). J. Mol. Biol. 316, 941-953.

Leung, D., Chen, E., Goeddel, D., A method for random mutagenesis of a defined DNA segment using a modified polymerase chain reaction (1989). Technique 1, 11-15.

Lorimer, I A, Pastan, I. (1995). Random recombination of antibody single change Fv sequences after fragmentation with DNaseI in the presence of Mn2+. Nucleic Acids. Res. 23:3067-3068.

Lin-Cereghino, J, Wong, WW, Xiong, S, Giang, W, Luong, L T, Vu, J, Johnson, S D, Lin-Cereghino, G P. (2005). Condensed protocol for competent cell preparation and tansformation of the methylotrophic yeast *Pichia pastoris*. Biotechniques, 38, 44, 46, 48.

Malo, M S, Alam, S N, Mostafa, G, Zeller, S J, Johnson, P V, Mohammad, N, Chen, K T, Moss, A K, Ramasamy, S, Faruqui, A, Hodin, S, Malo, P S, Ebrahimi, F, Biswas, B, Narisawa, S, Millan, J L, Warren, H S, Kaplan, J B, Kitts, C L, Hohmann, El, Hodin, R A. (2010). Intestinal alkaline phosphatase preserves the normal homeostasis of gut microbiota. Gut, 59:1476-1484.

Manes, T, Hoylaerts, M F, Muller, R, Lottspeich, F, Hoke, Millan, J L. (1998). Genetic complexity, structure, and characterization of highly active bovine intestinal alkaline phosphatases. J. Biol. Chem., 273:23353-23360.

Manuell, A L, Beligni, M V<Elder, J H, Siefker, D T, Tran, M, Weber, A, McDonald, T L, Mayfield, S P (2007). Robust expression of a bioactive mammalian protein in Chlamydomonas chloroplast. Plant Biotechnol. J. 5:402-412.

McCoullough, M J, Clemons, K V, McCusker, J H, Stevens, D A. (1998). Species indentification and virulence attributes of Saccharomyces boulardii. J. Clin. Microbiol. 36:2613.

Mellitzer, A, Ruth, C, Gustaffson, C, Welch, M, Girner-Brunberger, R, Weis, R, Purkarthofer, T, Glieder, A. (2014). Synergistic modular promoter and gene optimization to push cellulose secretion by *Pichia pastoris* beyond existing benchmarks. J. Biotechnology 191:187-95.

Millan, J L. Mammalian alkaline Phosphatases. Wiley-VCH Verlag GmbH & Co. 2006.

Moore, J C, Arnold, F H. (1996). Directed evolution of a para-nitrobenzyl esterase for aqueous-organic solvents. Nat. Biotechnol. 14:458-467

Muller, B H., Lamoure, C., Le Du, M-H., Cattolico, L., Lajeunesse, E., Lemaitre, F., Pearson, A., Ducancel, F., Menez, A., Boulain, J-C. Improving *Escherichia coli* alkaline phosphatase efficacy by additional mutations inside and outside the catalytic pocket (2001). Chembiochem. 2, 517-523.

Murphy, J E., Kantrowitz, E R. Why are mammalian alkaline phosphatases much more active than bacterial alkaline phosphatases? (1994) Molecular Microbiology. 12, 351-357.

Musiychuk, K, Stephenson, N, Bi, H, Farrance, C E, Orozovic, G, Brodelius, M, Brodelius, P, Horsey, A, Ugulava, N, Shamloul, A-M, Mett, V, Rabindran, S., Streatfield, S J, Yusibov, V. (2007). A launch vector for the production of vaccine antigens in plants. Influenza and Other Respiratory Viruses, 1:19-25.

Nehrenberg D L, Rodriguiz R M, Cyr M, Zhang X, Lauder J M, Gariépy J L, Wetsel W C. An anxiety-like phenotype in mice selectively bred for aggression. Behav Brain Res, 2009; 201(1): 179-91.

Oda, K, Amaya, Y, Fukushi-Irie, M, Kinameri, Y, Ohsuye, K, Kubota, I, Fujimura, S, Kobayashi, J. (1999). A general method for rapid purification of soluble versions of glycosylphosphatidylinositol-anchored proteins expressed in insect cells: an application for human tissue-nonspecific alkaline phosphatase. J. Biochem. 126:694-699.

Orlean, P, Menon, A K. (2007). GPI anchoring of protein in yeast and mammalian cells, or: how we learned to stop worrying and love glycophospholipids. J. Lipid Res. 48:993-1011.

Pfitzner, U M, Goodman, H M. (1987). Isolation and characterization of cDNA clones encoding pathogenesis-related proteins from tobacco mosaic virus infected tobacco plants. Nucleic Acids Res. 15:4449-4465.

Rasals, B S, Muto, M, Lee, PA, Jager, M, Cardoso, R M F, Behnke, C A, Kirk, P, Hokanson, C A, Crea, R, Mendez, M, Mayfield, S P (2010). Production of therapeutic proteins in algae, analysis of expression of seven human proteins in the chloroplast of *Chlamydomonas reinhardtii*. Plant Biotechnol. J. 8:719-733.

Schneider T, Roman A, Basta-Kaim A, Kubera M, Budziszewska B, Schneider K, Przewlocki R. Gender-specific behavioral and immunological alterations in an animal model of autism induced by prenatal exposure to valproic acid. Psychoneuroendocrinology, 2008; 33(6): 728-40.

Shaaltiel, Y, Bartfeld, D, Hasmueli, S, Baum, G, Brill-Almon, E, Galili, G, Dym, O, Boldin-Ada, sky. S A. Silman, I, Sussman, J L, Futerman, A H, Aviezer, D. (2007). Production of glucocerebrosidase with terminal mannos glycans for enzyme replacement therapy of Gaucher's disease using a plant cell system. Plant Biotechnol. J. , 5:579-590.

Shamloul, M, Trusa, J, Mett, V, Yusibov, V. (2014). Optimization and utilization of Agrobacterium-mediated transient protein production in Nicotiana. J. of Visualized Experiments, doi.10.3791/51204.

Specht, E, Miyake-Stoner, S, Mayfield, S. (2010). Microalgae come of age as a platform for recombinant protein production. Biotechnol. Lett. 32:1373-1383.

Stemmer, W. P. C. (1994a) "DNA Shuffling by random fragmentation and reassembly: In vitro recombination for molecular evolution", Proc. Natl. Acad. Sci. USA 91, 10747/10751.

Thomas A, Burant A, Bui N, Graham D, Yuva-Paylor L A, Paylor R. Marble burying reflects a repetitive and perseverative behavior more than novelty-induced anxiety. Psychopharmacology (Berl), 2009; 204(2): 361-73.

Tran, M, Van, C, Barrera, D J, Pettersson, P L, Peinado, C D, Bui, J. Mayfield, S P. (2013). Production of unique immunotoxin cancer therapeutics in algal chloroplasts. Proc. Natl. Acad. Sci. USA 110:E15-E22.

Wandelt, C I, Khan, M R, Craig, S, Schroeder, H E, Spencer, D, Higgins, T J. (1992). Vicilin with carboxy-termina KDEL is retained in the endoplasmic reticulum and accumulates to high levels in the leaves of transgenic plants. Plant J. 2:181-192.

Xu, H F., Zhang, X E., Zhang, Z P., Zhang, Y M., Cass, A E G (2003). Directed Evolution of E. coli Alkaline Phosphatase Towards Higher Catalytic Activity. Biocatalysis and Biotransformation. 21, 41-47.

Yang M, Silverman J L, Crawley J N. Automated three-chambered social approach task for mice. Curr Protoc Neurosci, 2011; Chapter 8: Unit 8.26.

Zhang, D, Nandi, S, Bryan, P, Pettit, S, Nguyen, D, Santos, M A, Huang, N. (2010). Expression, purification, and characterization of recombinant human transferrin from rice (Oryza sativa L.). Protein Expr. Purif. 74:69-79.

Zhang, F., Murhammer, D S, Linhardt, R J. (2002). Enzyme kinetics and glycan structural characterization of secreted alkaline phosphatase prepared using to baculovirus expression vector system. Appl. Biochem. Biotechnol. 101: 197-210.

Zhang, Y X, Zhu, Y, Xi, H W, Liu, Y L, Zhou, H M. (2002). Refolding and reactivation of calf intestinal alkaline phosphatase with excess magnesium ions. Int. J. Biochem. Cell. Biol. 34:1241-1247.

The invention claimed is:

1. A method of treating or preventing a neurodevelopmental disorder in a subject in need thereof comprising, administering to the subject an effective amount of a bovine intestinal alkaline phosphatase (bIAP) agent, wherein the neurodevelopmental disorder selected from autism spectrum disorder (ASD), schizophrenia, attention deficit hyperactivity disorder (ADHD), schizoaffective disorder, and bipolar affective disorder, and wherein the subject is an unborn child.

2. The method of claim 1, wherein the neurodevelopmental disorder is ASD.

3. The method of claim 2, wherein the treatment or prevention of ASD comprises reduction or elimination of one or more of social withdrawal, averted gaze, inability to make eye contact, repetitive behaviors, obsessions, anxiety, stereotyped movements, attention deficit, hyperactivity, depression, a reclusive personality, and the inability to understand feelings.

4. The method of claim 1, wherein the bIAP agent is administered to the pregnant mother of the unborn born child.

5. The method of claim 4, wherein the pregnant mother is afflicted with one or more of gastrointestinal dysbiosis, obesity, metabolic syndrome, gut-mediated systemic inflammation, and leaky gut.

6. The method of claim 4, wherein the bovine IAP is administered orally.

7. The method of claim 1, wherein the bovine IAP comprises an amino acid sequence having at least 95% sequence identity with any one of SEQ ID NOs: 2, 3, and 5-11.

8. The method of claim 1, wherein the bovine IAP is a bIAP II.

9. The method of claim 8, wherein the bovine IAP comprises an amino sequence having at least 95% sequence identity with SEQ ID NO: 2 (bIAP II).

10. The method of claim 9, wherein the bovine IAP comprises the amino sequence of SEQ ID NO: 2 (bIAP II).

11. The method of claim 1, wherein the bovine IAP is a bIAP IV.

12. The method of claim 11, wherein the bovine IAP comprises an amino sequence having at least 95% sequence identity with SEQ ID NO: 3 (bIAP IV).

13. The method of claim 12, wherein the bovine IAP comprises the amino sequence of SEQ ID NO: 3 (bIAP IV).

14. The method of claim 1, wherein the bovine IAP comprises a specific activity of at least about 100 U/mg to about 20,000 U/mg.

15. The method of claim 1, wherein the bovine IAP is stable and/or active in the GI tract, in one or more of the mouth, esophagus, stomach, duodenum, small intestine, jejunum, ileum, large intestine, colon, cecum, and rectum.

16. The method of claim 1, wherein the bovine IAP is substantially active at a pH of about 6.0 to about 12.

17. The method of claim 1, wherein the bovine IAP is stable in chyme.

18. A method of treating or preventing autism spectrum disorder (ASD) in an unborn child in need thereof comprising, administering to the mother of said unborn child an effective amount of a bovine intestinal alkaline phosphatase (bIAP),
wherein the mother is afflicted with one or more of gastrointestinal dysbiosis, obesity, metabolic syndrome, gut-mediated systemic inflammation, and leaky gut, and
wherein the bovine IAP comprises an amino acid sequence having at least 97% sequence identity with SEQ ID NO: 2 or SEQ ID NO: 3.

* * * * *